United States Patent
Kloos et al.

(10) Patent No.: US 7,089,247 B2
(45) Date of Patent: Aug. 8, 2006

(54) SYSTEM AND METHOD FOR RESOLVING A DISCREPANCY IN A CLINICAL DATA MANAGEMENT SYSTEM

(75) Inventors: Siegbert R. Kloos, Loerrach (DE); Anja Bornhausen, Loerrach (DE); John W. Egar, Boulder Creek, CA (US); Richard Sayer, Sunnyvale, CA (US); Peter J. O'Connor, Santa Clara, CA (US); Hugo De Schepper, Basel (CH)

(73) Assignee: Roche Palo Alto LLC, Palo Alto, CA (US)

( * ) Notice: Subject to any disclaimer, the term of this patent is extended or adjusted under 35 U.S.C. 154(b) by 732 days.

(21) Appl. No.: 10/161,103

(22) Filed: May 30, 2002

(65) Prior Publication Data

US 2003/0163488 A1 Aug. 28, 2003

Related U.S. Application Data

(63) Continuation-in-part of application No. 09/876,928, filed on Jun. 8, 2001, now Pat. No. 6,556,999.

(51) Int. Cl.
*G06F 17/30* (2006.01)

(52) U.S. Cl. .................. 707/10; 707/6; 707/104.1; 709/203; 705/2

(58) Field of Classification Search .............. 707/1, 707/6, 10, 201, 203; 705/2, 3; 709/203, 219
See application file for complete search history.

(56) References Cited

U.S. PATENT DOCUMENTS

| 5,924,074 A | 7/1999 | Evans | 705/3 |
|---|---|---|---|
| 5,950,192 A | 9/1999 | Moore et al. | 707/3 |
| 6,134,695 A | 10/2000 | Sasaki et al. | 714/752 |
| 6,151,581 A * | 11/2000 | Kraftson et al. | 705/3 |
| 6,665,647 B1 * | 12/2003 | Haudenschild | 705/2 |
| 6,735,551 B1 * | 5/2004 | Voegeli et al. | 702/183 |

FOREIGN PATENT DOCUMENTS

| WO | WO 99/63473 | 12/1999 |
|---|---|---|
| WO | PCT/US02/17799 | 6/2002 |
| WO | PCT/US02/17799 | 9/2003 |

OTHER PUBLICATIONS

Clintrial Bridge Abstract, Drug Information Association Montreal—Jun. 1997.

"CSC and Domain Pharma Announce Alliance to Support Life Sciences Industry" Jul. 28, 1998 Press Release, web site www.csc.com/newsandevents/news/1001.shtml, last accessed Sep. 10, 2003.

"Dendrite and Presidio Join Forces to Provide Automated Clinical Trial Solutions" Feb. 10, 1997 Press Release, web site www.dendrite.com/news/press/pr1997/021097a.html, last accessed Sep. 10, 2003.

(Continued)

*Primary Examiner*—Greta Robinson
*Assistant Examiner*—Cheryl Lewis
(74) *Attorney, Agent, or Firm*—Jones Day; Brett Lovejoy

(57) ABSTRACT

A method for electronically resolving a discrepancy arising in a clinical data management system is provided. The discrepancy is converted, using a conversion map, from a back-end format, used to store a clinical value corresponding to the discrepancy, into a front-end format that is compatible with a front-end study definition. The discrepancy is then transferred, while in the front-end format, to a front-end site where the clinical value associated with the discrepancy was first entered. A discrepancy response is received from the front-end site. When the discrepancy response resolves the discrepancy, the discrepancy response is stored in the clinical data management system, thereby resolving the discrepancy.

31 Claims, 15 Drawing Sheets

OTHER PUBLICATIONS cdisc.org—CDISC Proof-of-concept clinical data connectathon http://www.cdisc.org/news 01_07_10DIAConnectathon1.html pp 1–3: Accessed on Jun. 25, 2002.

cdisc.org—CDISC Proof-of-concept clinical data connectathon http://www.cdisc.org/pdf/WhosWho-Paris.PDF pp 1–2: Accessed Jun. 25, 2002.

csscomp.com—Data loading and conversion tool http://www.csscomp.com pp 1–2: Accessed on Jun. 25, 2002.

metatrial.com Company press release http://www.metatrial.com/Media/Releases.asp?vSeeAllPressReleases=false&PR=76 pp 1–3 Accessed on Jun. 25, 2002.

xml.coverpages.com—CDISC publishes CDISC operational data model (ODM) http://xml.coverpages.org/ni2002-05-09-a.html pp 1–2: Accessed on Jun. 25, 2002.

araccel.com—Company Home Page; http://www.araccel.com pp 1 : Accessed on Aug. 10, 2001.

araccel.com—Products; http://www.araccel.com/info.cfm?whichpage=11&whichcat=1 pp 1 : Accessed on Aug. 10, 2001.

araccel.com—Products; http://www.araccel.com/info.cfm?whichpage=11&whichcat=3 pp 1 : Accessed on Aug. 9, 2001.

araccel.com—Products; http://www.araccel.com/info.cfm?whichpage=11 & whichcat=4 pp 1 : Accessed on Aug. 9, 2001.

araccel.com—Products; http://www.araccel.com/info.cfm?whichpage=11&whichcat=5 pp 1–2 : Accessed on Aug. 9, 2001.

araccel.com—Enabling Technologies; http://www.araccel.com/info.cfm?whichpage=11&whichcat=13 pp 1–2 : Accessed on Aug. 9, 2001.

cbtech.com—Company Home Page; http://www.cbtech.com/ pp 1 : Accessed on Aug. 9, 2001.

cbtech.com—Meta Trial: electronic data capture software; http://www.cbtech.com/internal.asp?p=About pp 1 : Accessed on Aug. 9, 2001.

cbtech.com—MetaTrial: electronic data capture software; http://www.cbtech.com/internal.asp?p=MTEDC pp 1–2 : Accessed on Aug. 8, 2001.

cbtech.com—MetaTrial: electronic data capture software; http://www.cbtech.com/Internal.asp?p=MTEDC&sub=hybrid pp 1–2 : Accessed on Aug. 8, 2001.

cbtech.com—MetaTrial: electronic data capture software; http://www.cbtech.com/Internal.asp?p=MTEDC&sub=lite pp 1–2 : Accessed on Aug. 8, 2001.

cbtech.com—MetaTrial: electronic data capture software; http://www.cbtech.com/Internal.asp?p=MTEDC&sub=study pp 1–2 : Accessed on Aug. 8, 2001.

cbtech.com—MetaTrial: electronic data capture software; http://www.cbtech.com/Internal.asp?p=MTEDC&sub=portal pp 1–2 : Accessed on Aug. 8, 2001.

cbtech.com—MetaTrial: electronic data capture software; http://www.cbtech.com/Internal.asp?p=MTCompliance pp 1–2 : Accessed on Aug. 8, 2001.

clinsoft.net—Company Info and Service Documentation; http://www.clinsoft.net. pp. 1–4 : Accessed on Aug. 8, 2001.

clinsoft.net—Company Info; http://www.clinsoft.net/rc.nsf/about?OpenPage, pp 1 : Accessed on Aug. 8, 2001.

clinsoft.net—Clintrial 4 Release 4.3; http://www.clinsoft.net/dom5/products/clintrial/default.htm pp. 1–2 : Accessed on Aug. 9, 2001.

clinsoft.net—Clintrial 4 Release 4.3; http://www.clinsoft.net/dom5/products/clintrace/default.htm pp. 1–2 : Accessed on Aug. 9, 2001.

datatraknet.com—Company Home Page; http://www.datatraknet.com/master.cfm?pagename=Home&site_id=770 pp 1 : Accessed on Aug. 8, 200.

datatraknet.com—Products and Services Overview; http://www.datatraknet.com/master.cfm?site_id=227 pp 1 : Accessed on Aug. 9, 2001.

datatraknet.com—Datatrak Design; http://www.datatraknet.com/master.cfm?site_id=200 pp 1 : Accessed on Aug. 9, 2001.

datatraknet.com—Datatrak Entry; http://www.datatraknet.com/master.cfm?site_id=194 pp 1 : Accessed on Aug. 9, 2001.

datatraknet.com—Datatrak Review; http://www.datatraknet.com/master.cfm?site_id=772 pp 1 : Accessed on Aug. 9, 2001.

datatraknet.com—Datatrak Report; http://www.datatraknet.com/master.cfm?site_id=771 pp 1 : Accessed on Aug. 9, 2001.

datatraknet.com—Datatrak Export; http://www.datatraknet.com/master.cfm?site_id=774 pp 1 : Accessed on Aug. 9, 2001.

datatraknet.com—The EDC Value Proposition to the Pharmaceutical Industry PDF http://www.datatraknet.com/master.cfm?pagename=Home&site_id=890 pp 1–19 : Accessed on Aug. 9, 2001.

Infermed.com—Company Home Page; http://www/infermed.com/fr_r_home.htm. pp1 : Accessed on Aug. 9, 2001.

Infermed.com—Overview of Macro: Infermed's electronic data collection system; http://www.infermed.co.uk/ct_desc.htm pp. 1 : Accessed on Aug. 9, 2001.

Infermed.com—Features of Macro: System architecture; http://www.infermed.co.uk/ct_platforms.htm pp 1–: : Accessed on Aug. 9, 2001.

oracle.com—Oracle Clinical Remote Data Capture V4i PDF.Doc, http://www.oracle.com/industries/pharmaceuticals/index.html?solutions.html pp 1–4 : Accessed on Aug. 8, 2001.

oracle.com—Remote Data Capture in Clinical Trials: An Oracle White Paper PDF. Doc.; http://www.oracle.com/industries/pharmaceuticals/solutions.html pp 1–13: Accessed on Aug. 8, 2001.

phaseforward.com—Company Home Page; http://www.phaseforward.com pp1 : Accessed on Aug. 8, 2001.

phaseforward.com—Products Overview; http://www.phaseforward.com/Products/products.html pp 1 : Accessed on Aug. 8, 2001.

phaseforward.com—Infusion: Clinical Trials Management http://www.phaseforward.com/Products/Infusion.html pp 1–3 : Accessed on Aug. 8, 2001.

phaseforward.com—Inform:Clinical Data Management Solution http://www.phaseforward.com/Products/Inform.html pp 1–2 : Accessed on Aug. 8, 2001.

phaseforward.com—Inform Unplugged http://www.phaseforward.com/Products/inform%20unplugged.html pp 1–2 : Accessed on Aug. 8, 2001.

teamworks.de—Company Home Page; http://www.teamworks.de pp 1 : Accessed on Aug. 9, 2001.

teamworks.de—General Info; http://www.teamworks.de/About_us.html pp 1–2 : Accessed on Aug. 9, 2001.

teamworks.de—Services; http://www.teamworks.de/Services/services.html pp 1–2 : Accessed on Aug. 9, 2001.

* cited by examiner

| tmMapKey | ocMapKey | clin_plan_eve_id | clin_plan_event_name | visit_number | VisitId |
|---|---|---|---|---|---|
| 365 | 17036 | 17036 | SCREENING | 1 | 365 |
| 366 | 17136 | 17136 | WEEK -2 | 2 | 366 |
| 367 | 17236 | 17236 | WEEK -1 | 3 | 367 |
| 368 | 17336 | 17336 | WEEK 1 | 4 | 368 |

FIG. 7A

| tmMapKey | ocMapKey | dci_id | name | DciSeqNum | VisitId | CRFPageId |
|---|---|---|---|---|---|---|
| 316.365 | 35736.1 | 35736 | VS ANTR7 | 1 | 365 | 316 |
| 317.365 | 35636.1 | 35636 | CENTRAL LAB6 | 1 | 365 | 317 |
| 361.365 | 53936.1 | 53936 | ELECT_CHEM520 | 1 | 365 | 361 |

FIG. 7B

| TmMapKey | 317.null | 320.null |
|---|---|---|
| OcMapKey | 32936.1.1.35636 | 39136.1.1.35236 |
| dcm_id | 32936 | 39136 |
| dcm_subset_sn | 1 | 1 |
| dcm_layout_sn | 1 | 1 |
| dci_id | 35636 | 35236 |
| Name | CENTRAL LAB:32936.1.1 | ELIGIBILITY:39136.1.1 |
| subset_name | CLAB | ELIG |
| qual_question_id | 55106 | 55106 |
| clin_plan_eve_id | 17036 | 17036 |
| ContainedQuestions | null | null |
| QualifierFormula | (rowVal DataItemResponseHistory.CRFPageCycleNumber) | (rowVal DataItemResponseHistory.CRFPageCycleNumber) |
| VisitId | 365 | 365 |
| CRFPageId | 317 | 320 |
| VisitCycleNumber | null | null |
| CRFPageCycleNumber | null | null |

FIG. 7C

| | | |
|---|---|---|
| tmMapKey | 5 | 6 |
| ocMapKey | 32936.1.1.265236.1 | 32936.1.1.265636.1 |
| dcm_question_id | 265236 | 265636 |
| dcm_name | CENTRAL LAB | CENTRAL LAB |
| dcm_subset_name | CLAB | CLAB |
| dcm_que_dcm_subset_sn | 1 | 1 |
| dcm_que_dcm_layout_sn | 1 | 1 |
| dcm_id | 32936 | 32936 |
| dcm_question_group_id | 32536 | 32536 |
| dqg_name | CLAB | CLAB |
| qualifying_value | NULL | NULL |
| discrete_val_grp_id | NULL | NULL |
| question_name | SMPL_DATE | LAB_COM |
| occurrence_sn | 0 | 1 |
| discrete_val_grp_subset_nm | NULL | NULL |
| repeat_sn | 1 | 1 |
| formula | (formatDate dd/MM/yyyy (toUpper (responseTo 5))) | (toUpper (responseTo 6)) |
| DataItemTriggers | NULL | NULL |
| DataItemId | 5 | 6 |
| Description | [SMPL_DATE=SMPL_DATE:5] | [LAB_COM=LAB_COM:6] |

FIG. 8A

| tmMapKey | ocMapKey | DataItemId | DataItemName | Derivation |
|---|---|---|---|---|
| null | null | 10045 | Derived_Gender | SCREENING: DEMOGRAPHY:SEX |
| null | null | 10050 | Derived_visitd | 'This is a hidden question' |

FIG. 8B

| tmMapKey | ocMapKey | site_id | site | name | tmTrialSite | tmPersonId |
|---|---|---|---|---|---|---|
| rpl01621.1 | 1000009 | 1000009 | XDUMMY 1 | X DUMMY SITE 1 | rpl01621 | 1 |
| rpl01621.2 | 1000009 | 1000009 | XDUMMY 1 | X DUMMY SITE 1 | rpl01621 | 2 |
| rpl01621.3 | 1000009 | 1000009 | XDUMMY 1 | X DUMMY SITE 1 | rpl01621 | 3 |

FIG. 8C

| tmMapKey | ocMapKey | investigator_id | investigator | tmTrialSite | tmPersonId |
|---|---|---|---|---|---|
| rpl01621.1 | 1000009 | 1000009 | XDUMMY1 | rpl01621 | 1 |
| rpl01621.2 | 1000009 | 1000009 | XDUMMY1 | rpl01621 | 2 |
| rpl01621.3 | 1000009 | 1000009 | XDUMMY1 | rpl01621 | 3 |

FIG. 9A

| tmMapKey | ocMapKey | patient_position_id | patient | tmTrialSite | tmPersonId |
|---|---|---|---|---|---|
| rpl01621.1 | 37011 | 37011 | X1 | rpl01621 | 1 |
| rpl01621.2 | 37311 | 37311 | X4 | rpl01621 | 2 |
| rpl01621.3 | 37411 | 37411 | X5 | rpl01621 | 3 |

FIG. 9B

| tmMapKey | ocMapKey | tmFieldName | tmValue | ocFieldName | ocValue |
|---|---|---|---|---|---|
| DataItemId.12 | dcm_question_id.sub.lay.rpt.268036.1.1.2 | DataItemId | 12 | dcm_question_id.sub.lay.rpt | 268036.1.1.2 |
| DataItemId.59 | dcm_question_id.sub.lay.rpt.268036.2.1.2 | DataItemId | 59 | dcm_question_id.sub.lay.rpt | 268036.2.1.2 |
| ValueCode.YES | discrete_value_value.YES | ValueCode | YES | discrete_value_value | YES |
| ValueCode.YES2 | discrete_value_value.YES | ValueCode | YES2 | discrete_value_value | YES |
| CRFPageId.352 | dcm_id_sub_lay.38836.1.1 | CRFPageId | 352 | dcm_id_sub_lay | 38836.1.1 |
| VisitId.378 | clin_plan_eve_id.23036 | VisitId | 378 | clin_plan_eve_id | 23036 |
| CRFPageId.379 | dci_id.0 | CRFPageId | 379 | dci_id | 0 |

FIG. 9C

| variableName | Value |
|---|---|
| EnrollmentVisitId | 380 |
| InvestigatorDataItemId | 381 |
| SiteDataItemId | 382 |
| PatientDataItemId | 383 |

SYSTEM AND METHOD FOR RESOLVING A DISCREPANCY IN A CLINICAL DATA MANAGEMENT SYSTEM

1. CROSS REFERENCE TO RELATED APPLICATION

Under 35 U.S.C. § 120, this application is a continuation-in-part of prior United States Application entitled "System and Method for Bridging a Clinical Remote Data Entry Product to a Back-End Clinical Data Management System," Ser. No. 09/876,928, filed Jun. 8, 2001 now U.S. Pat. No. 6,556,999 B1.

2. COMPUTER PROGRAM LISTING APPENDIX

One compact disc that includes a Computer Program Listing Appendix has been submitted in duplicate in the present application. The size of the files contained in the Computer Program Listing Appendix, their date of creation, their time of creation, and their name are found in Table 1 below. In Table 1, each row represents a file or directory. If the row represents a directory, the designation "<DIR>" is provided in column one. If the row represents a file, the size of the file in bytes is provided in column one. Columns two and three respectively represent the date and time of file or directory creation while the fourth column represents the name of the file or directory.

TABLE 1

Contents of the Computer Program Listing Appendix

| | | | |
|---|---|---|---|
| Directory of \GGB_1.2.1 | | | |
| 5,740 | 05-03-02 | 4:23p | Changes_1_2_1.txt |
| 2,666 | 05-03-02 | 4:23p | Changes_1_1_37.txt |
| 3,725 | 05-03-02 | 4:23p | Changes_1_1_38.txt |
| 3,204 | 05-03-02 | 4:23p | Changes_1_1_51.txt |
| 1,775 | 05-03-02 | 4:23p | Changes_1_1_52.txt |
| <DIR> | 05-13-02 | 5:14p | clients |
| <DIR> | 05-13-02 | 5:09p | com |
| <DIR> | 05-03-02 | 4:23p | data |
| <DIR> | 05-03-02 | 4:23p | lib |
| Directory of D:\GGB_1.2.1\bin | | | |
| 31 | 05-03-02 | 4:23p | apitester.bat |
| 39 | 05-03-02 | 4:23p | auditortester.bat |
| 33 | 05-03-02 | 4:23p | datatester.bat |
| 38 | 05-03-02 | 4:23p | datetester.bat |
| 29 | 05-03-02 | 4:23p | dbtester.bat |
| 47 | 05-03-02 | 4:23p | exec.bat |
| 58 | 05-03-02 | 4:23p | execcli.bat |
| 27 | 05-03-02 | 4:23p | exectester.bat |
| 14 | 05-03-02 | 4:23p | ggb.bat |
| 66 | 05-03-02 | 4:23p | ggbconsole.bat |
| 151 | 05-03-02 | 4:23p | mapper.bat |
| 31 | 05-03-02 | 4:23p | maptester.bat |
| 37 | 05-03-02 | 4:23p | ocdatatester.bat |
| 3,153 | 05-03-02 | 4:23p | oldStartServer.bat |
| 33 | 05-03-02 | 4:23p | peertester.bat |
| 89 | 05-03-02 | 4:23p | rde.bat |
| 30 | 05-03-02 | 4:23p | rdesimulator.bat |
| 58 | 05-03-02 | 4:23p | rdetester.bat |
| 37 | 05-03-02 | 4:23p | reconcile.bat |
| 39 | 05-03-02 | 4:23p | rmipeertester.bat |
| 57 | 05-03-02 | 4:23p | run.bat |
| 402 | 05-03-02 | 4:23p | runnopause.bat |
| 2,557 | 05-03-02 | 4:23p | setup.bat |
| 2,351 | 05-03-02 | 4:23p | startServer.bat |
| 688 | 05-03-02 | 4:23p | stopServer.bat |
| 39 | 05-03-02 | 4:23p | storagetester.bat |
| 43 | 05-03-02 | 4:23p | studysitetester.bat |
| 35 | 05-03-02 | 4:23p | transtester.bat |
| 27 | 05-03-02 | 4:23p | wiptester.bat |
| Directory of D:\GGB_1.2.1\clients | | | |
| 368,100 | 05-03-02 | 4:28p | console.jar |
| 1,644 | 05-03-02 | 4:23p | console.html |
| <DIR> | 05-13-02 | 5:14p | CVS |
| 755 | 05-03-02 | 4:23p | index.html |
| 252,484 | 05-03-02 | 4:23p | ldap.jar |
| 547,976 | 05-03-02 | 4:28p | map.jar |
| 1,904 | 05-03-02 | 4:23p | map.html |
| Directory of D:\GGB_1.2.1\clients\CVS | | | |
| 180 | 05-03-02 | 4:23p | Entries |
| 48 | 05-03-02 | 4:23p | Repository |
| 53 | 05-03-02 | 4:23p | Root |
| Directory of D:\GGB_1.2.1\com | | | |
| <DIR> | 05-13-02 | 5:09p | roche |
| Directory of D:\GGB_1.2.1\com\roche | | | |
| <DIR> | 05-13-02 | 5:09p | rde |
| Directory of D:\GGB_1.2.1\com\roche\rde | | | |
| <DIR> | 05-13-02 | 5:16p | wip |
| Directory of D:\GGB_1.2.1\com\roche\rde\wip | | | |
| <DIR> | 05-13-02 | 5:14p | api |

TABLE 1-continued

Contents of the Computer Program Listing Appendix

| | | | |
|---|---|---|---|
| <DIR> | 05-13-02 | 5:14p | auditor |
| 13,290 | 07-17-01 | 10:49a | cg_logo.gif |
| <DIR> | 05-13-02 | 5:11p | console |
| <DIR> | 05-13-02 | 5:14p | CVS |
| <DIR> | 05-13-02 | 5:14p | dbconnect |
| <DIR> | 05-13-02 | 5:15p | doc-files |
| <DIR> | 05-03-02 | 4:26p | exec |
| 10,521 | 10-17-01 | 2:28a | GetEnv.java |
| <DIR> | 05-03-02 | 4:26p | graphics |
| <DIR> | 05-03-02 | 4:25p | install |
| 1,337 | 01-08-01 | 9:39a | issues.html |
| 4,548 | 04-03-02 | 4:09a | Makefile |
| <DIR> | 05-03-02 | 4:26p | metamapper |
| <DIR> | 05-03-02 | 4:27p | ocdata |
| <DIR> | 05-03-02 | 4:27p | ocmeta |
| 1,933 | 03-26-01 | 2:02a | overview.html |
| 4,564 | 02-20-01 | 4:57a | package.html |
| <DIR> | 05-03-02 | 4:25p | peer |
| <DIR> | 05-03-02 | 4:26p | rdesim |
| <DIR> | 05-03-02 | 4:27p | rdesvr |
| 534 | 06-26-01 | 6:38a | rlogomlt.gif |
| 20 | 04-11-00 | 3:30p | rmi.bat |
| <DIR> | 05-03-02 | 4:27p | service |
| <DIR> | 05-03-02 | 4:27p | storage |
| <DIR> | 05-03-02 | 4:26p | studysite |
| <DIR> | 05-03-02 | 4:24p | testdata |
| <DIR> | 05-03-02 | 4:26p | tester |
| <DIR> | 05-03-02 | 4:26p | tmdata |
| <DIR> | 05-03-02 | 4:26p | tmmeta |
| <DIR> | 05-03-02 | 4:28p | translator |
| 431 | 07-24-01 | 4:29a | users.dat |
| <DIR> | 05-03-02 | 4:28p | util |
| 12,885 | 04-10-02 | 1:22p | WipJUnitTest.java |
| 4,892 | 05-03-02 | 4:28a | WipJUnit.properties |
| 2,197 | 02-05-01 | 8:32a | WipProperties.java |
| 16,890 | 07-23-01 | 10:21a | Wip.java |
| 2,650 | 05-03-02 | 4:28p | Wip.properties |
| <DIR> | 05-03-02 | 4:24p | xml |

Directory of D:\GGB_1.2.1\com\roche\rde\wip\api

| | | | |
|---|---|---|---|
| 1,525 | 10-03-99 | 9:22p | ACDataMgr.java |
| 13,673 | 04-26-01 | 8:56a | ACDbFieldDefn.java |
| 9,241 | 08-23-00 | 1:09p | ACDbRow.java |
| 5,398 | 08-07-00 | 6:58p | ACDbTableDefn.java |
| 2,948 | 02-06-00 | 12:25p | ACMetaMgr.java |
| 8,099 | 04-09-02 | 4:00a | ACMetaMgrTest.java |
| 27,297 | 07-23-01 | 7:49a | ACPacket.java |
| 24,128 | 09-07-00 | 10:12p | ACPacketMgr.java |
| 6,354 | 07-23-01 | 7:51a | ApiUtil.java |
| 11,877 | 04-09-02 | 4:20a | ApiUtilTest.java |
| <DIR> | 05-13-02 | 5:14p | CVS |
| <DIR> | 05-13-02 | 5:14p | doc-files |
| 3,424 | 07-23-01 | 7:51a | FieldIsLesser.java |
| 4,533 | 07-23-01 | 7:51a | FieldsAreLesser.java |
| 1,470 | 09-02-99 | 9:11a | IWriteable.java |
| <DIR> | 05-13-02 | 5:14p | oc |
| 3,027 | 01-10-01 | 11:19a | package.html |
| <DIR> | 05-13-02 | 5:14p | ps |
| 8,532 | 06-07-00 | 1:32p | TableComparison.java |
| <DIR> | 05-13-02 | 5:10p | tl |
| <DIR> | 05-13-02 | 5:14p | tm |

Directory of D:\GGB_1.2.1\com\roche\rde\wip\api\CVS

| | | | |
|---|---|---|---|
| 756 | 05-03-02 | 4:23p | Entries |
| 67 | 05-03-02 | 4:23p | Entries.Log |
| 54 | 05-03-02 | 4:23p | Repository |
| 53 | 05-03-02 | 4:23p | Root |

Directory of D:\GGB_1.2.1\com\roche\rde\wip\api\doc-files

| | | | |
|---|---|---|---|
| 10,566 | 01-10-01 | 11:19a | api.gif |
| <DIR> | 05-13-02 | 5:14p | CVS |

Directory of D:\GGB_1.2.1\com\roche\rde\wip\api\doc-files\CVS

| | | | |
|---|---|---|---|
| 47 | 05-03-02 | 4:23p | Entries |
| 64 | 05-03-02 | 4:23p | Repository |
| 53 | 05-03-02 | 4:23p | Root |

Directory of D:\GGB_1.2.1\com\roche\rde\wip\api\oc

| | | | |
|---|---|---|---|
| 2,986 | 06-12-00 | 6:29p | ACOCPacket.java |
| <DIR> | 05-13-02 | 5:14p | CVS |
| 16,552 | 03-05-99 | 10:06a | ocglib.dtd |
| 12,040 | 09-27-99 | 7:11p | ocml.dtd |

TABLE 1-continued

Contents of the Computer Program Listing Appendix

| | | | |
|---|---|---|---|
| 14,091 | 05-26-99 | 6:04p | ocmlb.dtd |
| 28,981 | 03-09-99 | 1:03p | ocml_full.dtd |
| 4,126 | 03-16-99 | 4:27p | ocsimpl.dtd |
| 16,807 | 02-24-99 | 12:48p | OC_tbls.txt |
| 362 | 02-20-01 | 5:13a | package.html |
| Directory of D:\GGB_1.2.1\com\roche\rde\wip\api\oc\CVS | | | |
| 366 | 05-03-02 | 4:23p | Entries |
| 57 | 05-03-02 | 4:23p | Repository |
| 53 | 05-03-02 | 4:23p | Root |
| Directory of D:\GGB_1.2.1\com\roche\rde\wip\api\ps | | | |
| <DIR> | 05-13-02 | 5:14p | CVS |
| 16,395 | 04-16-99 | 5:52p | psml.dtd |
| Directory of D:\GGB_1.2.1\com\roche\rde\wip\api\ps\CVS | | | |
| | 05-03-02 | 4:23p | Entries |
| | 05-03-02 | 4:23p | Repository |
| 53 | 05-03-02 | 4:23p | Root |
| Directory of D:\GGB_1.2.1\com\roche\rde\wip\api\tl | | | |
| <DIR> | 05-13-02 | 5:14p | CVS |
| Directory of D:\GGB_1.2.1\com\roche\rde\wip\api\tl\CVS | | | |
| 3 | 05-03-02 | 4:23p | Entries |
| 57 | 05-03-02 | 4:23p | Repository |
| 53 | 05-03-02 | 4:23p | Root |
| Directory of D:\GGB_1.2.1\com\roche\rde\wip\api\tm | | | |
| 22,243 | 04-02-02 | 10:21a | ACEdiFileReader.java |
| 11,549 | 05-01-02 | 11:56a | ACTMPacket.java |
| <DIR> | 05-13-02 | 5:14p | CVS |
| 1,153 | 04-25-00 | 4:10p | EdiFile.properties |
| 361 | 02-20-01 | 5:13a | package.html |
| 5,202 | 09-09-99 | 8:56a | tmml.dtd |
| Directory of D:\GGB_1.2.1\com\roche\rde\wip\api\tm\CVS | | | |
| 248 | 05-03-02 | 4:23p | Entries |
| 57 | 05-03-02 | 4:23p | Repository |
| 53 | 05-03-02 | 4:23p | Root |
| Directory of D:\GGB_1.2.1\com\roche\rde\wip\auditor | | | |
| 14,657 | 09-28-00 | 6:47p | AuditorMgr.java |
| 3,935 | 12-18-00 | 8:25a | AuditorUtil.java |
| <DIR> | 05-13-02 | 5:14p | CVS |
| 6,587 | 12-19-00 | 5:40a | Differ.java |
| <DIR> | 05-13-02 | 5:14p | doc-files |
| 457 | 09-19-00 | 11:54a | IMatcher.java |
| 6,562 | 09-19-00 | 11:54a | OCDbField.java |
| 1,134 | 12-19-00 | 5:41a | OCDbRow.java |
| 1,183 | 09-19-00 | 11:54a | OCDbTable.java |
| 3,066 | 12-18-00 | 8:41a | OCPatientDataMgr.java |
| 5,977 | 12-18-00 | 8:40a | OCPatientDataPacket.java |
| 3,445 | 09-19-00 | 11:54a | OCTablesInfoReader.java |
| 2,613 | 12-18-00 | 8:27a | OCTables.properties |
| 1,762 | 01-15-01 | 9:55a | package.html |
| 16,923 | 12-18-00 | 8:37a | PatientAuditor.java |
| 5,516 | 12-19-00 | 5:42a | PatientAuditTester.java |
| 534 | 09-19-00 | 11:54a | RepeatingQMatcher.java |
| 2,806 | 12-19-00 | 5:43a | StringMatcher.java |
| 5,127 | 12-27-00 | 10:32p | StudyAudit.java |
| 2,463 | 09-28-00 | 3:57p | StudyAuditEvent.java |
| 65,613 | 02-04-02 | 1:04p | StudyAuditor.java |
| 549 | 09-19-00 | 11:54a | TranslatedValueMatcher.java |
| Directory of D:\GGB_1.2.1\com\roche\rde\wip\auditor\CVS | | | |
| 1,041 | 05-03-02 | 4:23p | Entries |
| 19 | 05-03-02 | 4:23p | Entries.Log |
| 58 | 05-03-02 | 4:23p | Repository |
| 53 | 05-03-02 | 4:23p | Root |
| Directory of D:\GGB_1.2.1\com\roche\rde\wip\auditor\doc-files | | | |
| 13,609 | 01-10-01 | 12:16p | auditor.gif |
| <DIR> | 05-13-02 | 5:14p | CVS |
| Directory of D:\GGB_1.2.1\com\roche\rde\wip\auditor\doc-files\CVS | | | |
| 51 | 05-03-02 | 4:23p | Entries |
| 68 | 05-03-02 | 4:23p | Repository |
| 53 | 05-03-02 | 4:23p | Root |
| Directory of D:\GGB_1.2.1\com\roche\rde\wip\console | | | |
| <DIR> | 05-13-02 | 5:14p | CVS |
| Directory of D:\GGB_1.2.1\com\roche\rde\wip\console\CVS | | | |
| 3 | 05-03-02 | 4:23p | Entries |
| 58 | 05-03-02 | 4:23p | Repository |
| 53 | 05-03-02 | 4:23p | Root |
| Directory of D:\GGB_1.2.1\com\roche\rde\wip\CVS | | | |
| 661 | 05-03-02 | 4:23p | Entries |
| 398 | 05-03-02 | 4:24p | Entries.Log |

TABLE 1-continued

Contents of the Computer Program Listing Appendix

| | | | |
|---|---|---|---|
| 50 | 05-03-02 | 4:23p | Repository |
| 53 | 05-03-02 | 4:23p | Root |

Directory of D:\GGB_1.2.1\com\roche\rde\wip\dbconnect

| | | | |
|---|---|---|---|
| 17,150 | 07-30-01 | 4:45a | ConnectionSet.java |
| <DIR> | 05-13-02 | 5:14p | CVS |
| 4,158 | 04-02-02 | 10:08a | DB.properties |
| 34,559 | 05-04-01 | 2:56a | DBConnectMgr.java |
| 14,955 | 04-10-02 | 3:29a | DBConnectMgrTest.java |
| <DIR> | 05-13-02 | 5:14p | doc-files |
| 825 | 01-10-01 | 11:20a | package.html |

Directory of D:\GGB_1.2.1\com\roche\rde\wip\dbconnect\CVS

| | | | |
|---|---|---|---|
| 257 | 05-03-02 | 4:23p | Entries |
| 19 | 05-03-02 | 4:23p | Entries.Log |
| 60 | 05-03-02 | 4:23p | Repository |
| 53 | 05-03-02 | 4:23p | Root |

Directory of D:\GGB_1.2.1\com\roche\rde\wip\dbconnect\doc-files

| | | | |
|---|---|---|---|
| <DIR> | 05-13-02 | 5:14p | CVS |
| 1,814 | 01-10-01 | 12:16p | dbconnect.gif |

Directory of D:\GGB_1.2.1\com\roche\rde\wip\dbconnect\doc-files\CVS

| | | | |
|---|---|---|---|
| 53 | 05-03-02 | 4:23p | Entries |
| 70 | 05-03-02 | 4:23p | Repository |
| 53 | 05-03-02 | 4:23p | Root |

Directory of D:\GGB_1.2.1\com\roche\rde\wip\doc-files

| | | | |
|---|---|---|---|
| 5,709 | 01-15-01 | 10:06a | applet_security.gif |
| 99,880 | 02-12-01 | 7:44a | AuditorMgr_readStudyAuditFromFile( ).gif |
| 47,112 | 02-12-01 | 7:44a | AuditorMgr_main( ).gif |
| 12,645 | 02-12-01 | 7:44a | AuditorMgr_getAuditEvents( ).gif |
| 44,488 | 02-12-01 | 7:44a | AuditorMgr_writeStudyAuditToFile( ).gif |
| 29,485 | 02-12-01 | 7:44a | AuditorMgr_writeAllPatientAuditsToFile( ).gif |
| 2,130 | 02-12-01 | 7:44a | AuditorMgr_update( ).gif |
| 8,008 | 02-12-01 | 7:44a | AuditorMgr_the( ).gif |
| 4,286 | 02-12-01 | 7:44a | AuditorMgr_includesNewDerivedItems( ).gif |
| 53,217 | 02-12-01 | 7:44a | AuditorMgr_writeAuditDiffToFile( ).gif |
| 13,609 | 02-12-01 | 7:44a | auditor.gif |
| 37,820 | 02-12-01 | 7:44a | AuditorMgr_addNewDerivedItemsToMap( ).gif |
| 6,267 | 02-12-01 | 7:44a | AuditorMgr_AuditorMgr( ).gif |
| 150,344 | 02-12-01 | 7:44a | AuditorMgr_conductStudyAudit( ).gif |
| 4,211 | 02-12-01 | 7:44a | AuditorMgr_countNewDerivedItems( ).gif |
| 142,462 | 03-01-01 | 6:37a | ConsoleApi.resetLoadStatus.gif |
| 50,019 | 03-01-01 | 6:37a | ConsoleApi.getRDEMachineStatus.gif |
| 9,213 | 01-04-01 | 5:54p | console_exec_class.gif |
| 75,124 | 03-01-01 | 6:37a | ConsoleApi.getPropertiesCount.gif |
| 86,916 | 03-01-01 | 6:37a | ConsoleApi.resetOCSystem.gif |
| 81,611 | 04-11-01 | 1:49a | ConsoleApi.setProperty.gif |
| 13,116 | 03-01-01 | 6:37a | ConsoleApi.getProperty.gif |
| 23,070 | 03-01-01 | 6:37a | ConsoleApi.getOCPatientCount.gif |
| 50,102 | 03-01-01 | 6:37a | ConsoleApi.getServerStatus.gif |
| 26,533 | 03-01-01 | 6:37a | ConsoleApi.getStudyList.gif |
| 6,262 | 03-01-01 | 6:37a | ConsoleApi.getOCPatientMap.gif |
| 38,314 | 03-01-01 | 6:37a | ConsoleApi.getChildren.gif |
| 36,452 | 03-01-01 | 6:37a | ConsoleApi.getServerState(1).gif |
| 36,570 | 03-01-01 | 6:37a | ConsoleApi.getGraphActivity.gif |
| 4,723 | 03-01-01 | 6:37a | ConsoleApi.getLogEventCount.gif |
| 35,821 | 03-01-01 | 6:37a | ConsoleApi.isSiteLoading.gif |
| 57,977 | 03-01-01 | 6:37a | ConsoleApi.resetTMSystem.gif |
| 34,613 | 03-01-01 | 6:37a | ConsoleApi.isStudyLoading.gif |
| 38,866 | 03-01-01 | 6:37a | ConsoleApi.getRDEMachineList.gif |
| 14,904 | 03-01-01 | 6:37a | ConsoleApi.getServerState.gif |
| 12,563 | 03-01-01 | 6:37a | ConsoleApi.getLogEvent.gif |
| 4,885 | 03-01-01 | 6:37a | ConsoleApi.getRootNode.gif |
| 178,754 | 03-01-01 | 6:37a | Configurator.start.gif |
| 6,089 | 01-15-01 | 10:06a | configure_panel_design.gif |
| 32,722 | 03-01-01 | 6:37a | ConsoleApi.doAuthorization.gif |
| 34,401 | 01-15-01 | 12:05p | console_exec.html |
| 10,747 | 03-01-01 | 6:37a | ConsoleApi.doProcessNow.gif |
| 25,723 | 03-01-01 | 6:37a | ConsoleApi.doRestartExec.gif |
| 26,027 | 03-01-01 | 6:37a | ConsoleApi.doShutdown.gif |
| <DIR> | 05-03-02 | 4:24p | CVS |
| 1,857 | 01-17-01 | 6:08p | databases.html |
| 7,110 | 03-26-01 | 1:55a | DBUtil_rollback( ).gif |
| 9,898 | 03-26-01 | 1:55a | DBUtil_isSequencePresent( ).gif |
| 17,128 | 03-26-01 | 1:55a | DBUtil_retrieveColumnProperties( ).gif |
| 31,668 | 03-26-01 | 1:55a | DBUtil_retrieveRows(1).gif |
| 43,791 | 03-26-01 | 1:55a | DBUtil_readCurrentSequenceMax( ).gif |
| 7,716 | 03-26-01 | 1:55a | DBUtil_getSimplifiedDatatype( ).gif |
| 8,809 | 03-26-01 | 1:55a | DBUtil_concatSQLList( ).gif |
| 14,535 | 03-26-01 | 1:55a | DBUtil_getSelectionAsString( ).gif |

TABLE 1-continued

Contents of the Computer Program Listing Appendix

| | | | |
|---:|---|---|---|
| 9,580 | 03-26-01 | 1:55a | DBUtil__retrieveRows(0).gif |
| 69,598 | 03-26-01 | 1:55a | DBUtil__updateACDbRow( ).gif |
| 61,209 | 03-26-01 | 1:55a | DBUtil__insertACDbRow( ).gif |
| 100,466 | 03-26-01 | 1:55a | DBUtil__retrieveColumns( ).gif |
| 80,353 | 03-26-01 | 1:55a | DBUtil__retrieveNamedColumn( ).gif |
| 15,827 | 03-26-01 | 1:55a | DBUtil__retrieveFieldAsACField( ).gif |
| 5,420 | 03-26-01 | 1:55a | DBUtil__isTableNonEmpty( ).gif |
| 29,418 | 03-26-01 | 1:55a | DBUtil__retrieveFieldAsString( ).gif |
| 3,729 | 03-26-01 | 1:55a | DBUtil__executeQueryOnPrepStmt( ).gif |
| 15,475 | 03-26-01 | 1:55a | DBUtil__retrieveFieldAsObject( ).gif |
| 5,559 | 03-26-01 | 1:55a | DBUtil__vectorToRows( ).gif |
| 67,996 | 03-26-01 | 1:55a | DBUtil__retrieveColumn( ).gif |
| 9,851 | 03-26-01 | 1:55a | DBUtil__isViewPresent( ).gif |
| 9,594 | 03-26-01 | 1:55a | DBUtil__isUserPresent( ).gif |
| 33,568 | 03-26-01 | 1:55a | DBUtil__readSequenceNextVal( ).gif |
| 57,420 | 03-26-01 | 1:55a | DBUtil__rowCount( ).gif |
| 3,994 | 03-26-01 | 1:55a | DBUtil__retrieveDBMetaData( ).gif |
| 53,186 | 03-26-01 | 1:55a | DBUtil__convertResultSet( ).gif |
| 9,818 | 03-26-01 | 1:55a | DBUtil__isTablePresent( ).gif |
| 9,059 | 03-26-01 | 1:55a | DBUtil__executeDCnt( ).gif |
| 91,546 | 03-26-01 | 1:55a | DBUtil__retrieveRowsAs(0).gif |
| 97,546 | 03-26-01 | 1:55a | DBUtil__retrieveRowsAs(1).gif |
| 18,748 | 03-26-01 | 1:55a | DBUtil__executePrepStmt( ).gif |
| 9,678 | 03-26-01 | 1:55a | DBUtil__isTablespacePresent( ).gif |
| 15,108 | 03-26-01 | 1:55a | DBUtil__getMinValue( ).gif |
| 19,591 | 03-26-01 | 1:55a | DBUtil__convertResultsToStringArrays( ).gif |
| 15,199 | 03-26-01 | 1:55a | DBUtil__getMaxValue( ).gif |
| 18,927 | 03-26-01 | 1:55a | DBUtil__incrementSequence( ).gif |
| 7,886 | 03-26-01 | 1:55a | DBUtil__executeDQL( ).gif |
| 5,632 | 03-26-01 | 1:55a | DBUtil__executeDDL( ).gif |
| 12,976 | 03-26-01 | 1:55a | DBUtil__mapNamesEqValues( ).gif |
| 31,674 | 03-26-01 | 1:55a | DBUtil__retrieveRowProps( ).gif |
| 15,625 | 03-26-01 | 1:55a | DBUtil__getACDbRows( ).gif |
| 19,844 | 03-26-01 | 1:55a | DBUtil__createWhereClause( ).gif |
| 7,106 | 03-26-01 | 1:55a | DBUtil__commit( ).gif |
| 505,423 | 03-26-01 | 1:55a | DBUtil__concatNamesAndValuesSql( ).gif |
| 21,526 | 03-26-01 | 1:55a | DBUtil__createPreparedStmt(0).gif |
| 8,062 | 03-26-01 | 1:55a | DBUtil__listValuesTyped( ).gif |
| 46,018 | 03-26-01 | 1:55a | DBUtil__createPreparedStmt(1).gif |
| 2,206 | 03-26-01 | 1:55a | DBUtil__convertDatatypeToStringName( ).gif |
| 106,142 | 03-26-01 | 1:55a | DBUtil__getRow( ).gif |
| 31,219 | 03-26-01 | 1:55a | DBUtil__assertCnxn( ).gif |
| 31,973 | 03-26-01 | 1:55a | DBUtil__assertCnxnAndAccount( ).gif |
| 4,924 | 03-26-01 | 1:55a | DBUtil__closeStatementSet( ).gif |
| 406,312 | 03-26-01 | 1:55a | DBUtil__codeValInSqlString( ).gif |
| 5,709 | 02-23-01 | 1:37p | dig__cert__approv__dlg.gif |
| 14,691 | 01-22-01 | 11:49a | distrib__arch.html |
| 26,079 | 03-01-01 | 6:37a | ExecCli.doShutdown.gif |
| 27,414 | 03-01-01 | 6:37a | ExecCli.cliShutdown.gif |
| 40,344 | 03-01-01 | 6:37a | ExecCli.cliDisableStudySite.gif |
| 19,504 | 03-01-01 | 6:37a | ExecCli.cliShowVersion.gif |
| 38,742 | 03-01-01 | 6:37a | ExecCli.cliDisableTM.gif |
| 33,885 | 03-01-01 | 6:37a | ExecCli.cliEnableStudy.gif |
| 8,914 | 03-01-01 | 6:37a | ExecCli.cliPause.gif |
| 3,482 | 03-01-01 | 6:37a | ExecCli.cliShowSac.gif |
| 33,900 | 03-01-01 | 6:37a | ExecCli.cliDisableStudy.gif |
| 12,806 | 03-01-01 | 6:37a | ExecCli.cliSendMail.gif |
| 9,308 | 03-01-01 | 6:37a | ExecCli.cliResume.gif |
| 5,090 | 03-01-01 | 6:37a | ExecCli.cliSetWip.gif |
| 39,810 | 03-01-01 | 6:37a | ExecCli.cliUpdate.gif |
| 190,607 | 03-01-01 | 6:37a | ExecCli.cliReset.gif |
| 26,052 | 03-01-01 | 6:37a | ExecCli.doRestartExec.gif |
| 32,843 | 03-01-01 | 6:37a | ExecCli.cliEnableOcTest.gif |
| 21,281 | 03-01-01 | 6:37a | ExecCli.doProcessNow.gif |
| 23,110 | 03-01-01 | 6:37a | ExecCli.cliProcess.gif |
| 33,598 | 03-01-01 | 6:37a | ExecCli.cliDisableOcTest.gif |
| 55,269 | 03-01-01 | 6:37a | ExecCli.cliReloadStudySite.gif |
| 38,536 | 03-01-01 | 6:37a | ExecCli.cliEnableOC.gif |
| 20,973 | 03-01-01 | 6:37a | ExecCli.cliShowConfig.gif |
| 2,531 | 03-01-01 | 6:37a | ExecCli.cliShowPaused.gif |
| 4,824 | 03-01-01 | 6:37a | ExecCli.cliShowTimers.gif |
| 38,652 | 03-01-01 | 6:37a | ExecCli.cliEnableTM.gif |
| 2,848 | 03-01-01 | 6:37a | ExecCli.cliShowUptime.gif |
| 40,172 | 03-01-01 | 6:37a | ExecCli.cliEnableStudySite.gif |
| 52,684 | 03-01-01 | 6:37a | ExecCli.cliAddStudy.gif |
| 6,460 | 03-01-01 | 6:37a | ExecCli.cliAudit.gif |
| 4,810 | 03-01-01 | 6:37a | ExecCli.cliConnect(1).gif |

TABLE 1-continued

Contents of the Computer Program Listing Appendix

| | | | |
|---|---|---|---|
| 38,642 | 03-01-01 | 6:37a | ExecCli.cliDisableOC.gif |
| 67,468 | 04-11-01 | 3:34a | ExecMgr.start.gif |
| 11,812 | 03-01-01 | 5:42a | exec_server.html |
| 5,143 | 03-01-01 | 6:37a | ExecCli.cliSetProfiler.gif |
| 4,425 | 01-22-01 | 11:48a | ggb_console_architecture.gif |
| 4,603 | 01-22-01 | 11:48a | ggb_mapper_architecture.gif |
| 167,145 | 03-01-01 | 6:37a | Installer.start.gif |
| 7,684 | 02-20-01 | 1:00a | installation.html |
| 4,247 | 01-04-01 | 5:54p | jtable_class.gif |
| 6,218 | 01-04-01 | 5:54p | jtree_class.gif |
| 3,528 | 01-15-01 | 10:07a | launch_map_application.gif |
| 5,047 | 01-04-01 | 5:54p | launch_applet.gif |
| 3,762 | 01-04-01 | 5:54p | launch_application.gif |
| 18,959 | 01-04-01 | 5:54p | launch_console_class.gif |
| 5,101 | 01-15-01 | 10:07a | launch_map_applet.gif |
| 21,472 | 01-04-01 | 5:54p | logon_detail.gif |
| 2,771 | 02-23-01 | 1:37p | logon_panel.gif |
| 35,823 | 02-12-01 | 7:48a | MapMgr_getCurrentStudyId( ).gif |
| 92,735 | 02-12-01 | 7:48a | MapMgr_setOCMetaPacket( ).gif |
| 2,162 | 02-12-01 | 7:48a | MapMgr_getOCMetaPacket( ).gif |
| 164,952 | 02-12-01 | 7:48a | MapMgr_updateMapWithTMMeta( ).gif |
| 2,155 | 02-12-01 | 7:48a | MapMgr_getTmClinicalTrial( ).gif |
| 57,123 | 03-06-01 | 5:55a | MapExecApi.startSession.gif |
| 10,458 | 02-12-01 | 7:48a | MapMgr_writeStudyMapToTabularFile( ).gif |
| 122,456 | 02-12-01 | 7:48a | MapMgr_getRDEPagesWithVisitId( ).gif |
| 2,133 | 02-12-01 | 7:48a | MapMgr_getCurrentStudyMap( ).gif |
| 2,174 | 02-12-01 | 7:48a | MapMgr_setCurrentStudyMap( ).gif |
| 34,624 | 02-12-01 | 7:48a | MapMgr_getRDEQuestionsWithVisitId(0).gif |
| 44,137 | 02-12-01 | 7:48a | MapMgr_update( ).gif |
| 159,273 | 02-12-01 | 7:48a | MapMgr_getRDEQuestionsWithVisitId(1).gif |
| 1,978 | 02-12-01 | 7:48a | MapMgr_getProperties( ).gif |
| 2,228 | 02-12-01 | 7:48a | MapMgr_setTMMetaPacket( ).gif |
| 2,173 | 02-12-01 | 7:48a | MapMgr_getTMMetaPacket( ).gif |
| 8,143 | 02-12-01 | 7:48a | MapMgr_getTmCRFPageForId( ).gif |
| 4,891 | 02-12-01 | 7:48a | MapMgr_setCurrentACPacket( ).gif |
| 78,326 | 03-06-01 | 5:55a | MapExecApi.writeProperty.gif |
| 7,539 | 02-12-01 | 7:48a | MapMgr_readStudyMapTabularFile( ).gif |
| 6,590 | 02-12-01 | 7:48a | MapMgr_getHighestRepeatNumber( ).gif |
| 164,656 | 02-12-01 | 7:48a | MapMgr_getMetaElementForId( ).gif |
| 13,477 | 02-12-01 | 7:48a | MapMgr_readStudyMapFile( ).gif |
| 166,197 | 02-12-01 | 7:48a | MapMgr_improveTmPrompts( ).gif |
| 3,255 | 02-12-01 | 7:48a | MapMgr_getTMMetaManager( ).gif |
| 5,652 | 02-12-01 | 7:48a | MapMgr_isRequiringPatientCode( ).gif |
| 2,092 | 02-12-01 | 7:48a | MapMgr_setTMMetaManager( ).gif |
| 5,937 | 02-12-01 | 7:48a | MapMgr_isUsingTestMapAndMetaFiles( ).gif |
| 53,510 | 02-12-01 | 7:48a | MapMgr_getMetaElements( ).gif |
| 10,064 | 02-12-01 | 7:48a | MapMgr_getCurrentOcCpes( ).gif |
| 12,145 | 02-12-01 | 7:48a | MapMgr_writeStudyMapToFile( ).gif |
| 3,704 | 02-12-01 | 7:48a | MapMgr_getMappingEvents( ).gif |
| 6,276 | 02-12-01 | 7:48a | MapMgr_isDeletedDcmQuestion( ).gif |
| 6,563 | 02-12-01 | 7:48a | MapMgr_getLowestRepeatNumber( ).gif |
| 153,603 | 02-12-01 | 7:48a | MapMgr_getRDEQuestionsWithPageId( ).gif |
| 22,626 | 01-22-01 | 11:50a | macro_api.html |
| 45,237 | 02-12-01 | 7:48a | MapMgr_getCurrentStudyName( ).gif |
| 3,400 | 02-12-01 | 7:48a | MapMgr_the( ).gif |
| 7,828 | 02-12-01 | 7:48a | MapMgr_isRepeatingCRF( ).gif |
| 32,366 | 03-06-01 | 5:55a | MapExecApi.doAuthorization.gif |
| 38,263 | 03-06-01 | 5:55a | MapExecApi.isStudyReleased.gif |
| 12,354 | 03-06-01 | 5:55a | MapExecApi.readProperties.gif |
| 125,635 | 03-06-01 | 5:55a | MapExecApi.setStudyReleased.gif |
| 52,367 | 02-12-01 | 7:48a | MapMgr_addGroupRepeats( ).gif |
| 162,595 | 02-12-01 | 7:48a | MapMgr_buildTMMapForOCStudy( ).gif |
| 2,665 | 02-12-01 | 7:48a | MapMgr_getCurrentACPacket( ).gif |
| 2,285 | 02-12-01 | 7:48a | MagMgr_getCurrentOcClinicalStudy( ).gif |
| 5,374 | 01-08-01 | 4:05p | mapper_server_arch.gif |
| 22,550 | 01-15-01 | 10:09a | mapper_client.html |
| 63,858 | 01-08-01 | 4:05p | mapper_server.html |
| 1,292 | 02-21-01 | 7:39a | mapper_study.html |
| 3,524 | 01-15-01 | 10:07a | map_client_server.gif |
| 10,536 | 02-12-01 | 7:50a | metadata_tmmeta.html |
| 14,923 | 02-12-01 | 7:50a | metadata_overview.html |
| 2,219 | 01-17-01 | 6:08p | metadata.html |
| 5,818 | 02-12-01 | 7:50a | metadata_auditor.html |
| 16,217 | 02-12-01 | 7:50a | metadata_metamapper.html |
| 12,957 | 02-12-01 | 7:50a | metadata_ocmeta.html |
| 98,656 | 02-12-01 | 7:51a | metamapper.gif |
| 2,475 | 02-12-01 | 7:48a | meta_process1.gif |

TABLE 1-continued

Contents of the Computer Program Listing Appendix

| | | | |
|---|---|---|---|
| 2,446 | 02-12-01 | 7:48a | meta_process2.gif |
| 3,967 | 02-12-01 | 7:48a | meta_process3.gif |
| 11,911 | 02-27-01 | 4:48a | OCDataMgr_writeOCDataPacketToFile( ).gif |
| 2,104 | 02-12-01 | 7:49a | OCMetaMgr_getStudyPropertyCols( ).gif |
| 46,804 | 02-27-01 | 4:48a | OCDataMgr_update( ).gif |
| 4,931 | 02-12-01 | 7:49a | OCMetaMgr_the( ).gif |
| 2,027 | 02-12-01 | 7:49a | OCDataMgr_getProperties( ).gif |
| 2,044 | 02-27-01 | 4:48a | OCDataMgr_getProperties( ).gif |
| 21,622 | 02-12-01 | 7:49a | OCDataMgr_getElementNameForTable( ).gif |
| 16,752 | 02-12-01 | 7:49a | OCMetaMgr_getProperty( ).gif |
| 2,886 | 02-27-01 | 4:48a | OCDataMgr_setCurrentACPacket( ).gif |
| 184,771 | 02-27-01 | 4:48a | OCDataMgr_main( ).gif |
| 94,263 | 02-12-01 | 7:49a | OCDataMgr_getStudyProperties(0).gif |
| 61,295 | 02-12-01 | 7:49a | OCDataMgr_getStudyProperties(1).gif |
| 18,135 | 02-27-01 | 4:48a | OCDataMgr_readTabularOCDataPacket( ).gif |
| 2,041 | 02-27-01 | 4:48a | OCDataMgr_setOCHostUrl( ).gif |
| 19,302 | 02-12-01 | 7:49a | OCMetaMgr_getTableNameForElement( ).gif |
| 48,936 | 02-12-01 | 7:49a | OCMetaMgr_update( ).gif |
| 129,298 | 02-27-01 | 4:48a | OCDataMgr_loadOCDataToORCL( ).gif |
| 9,607 | 02-12-01 | 7:49a | OCMetaMgr_writeOCMetaTablesToFile( ).gif |
| 12,176 | 02-12-01 | 7:49a | OCMetaMgr_getStudyNames( ).gif |
| 2,206 | 02-12-01 | 7:49a | OCMetaMgr_getSelectedStudyProps( ).gif |
| 2,207 | 02-27-01 | 4:48a | OCMetaMgr_setIsUsingTestMode( ).gif |
| 63,664 | 02-12-01 | 7:49a | OCMetaMgr_getCurrentStudyName( ).gif |
| 2,270 | 02-12-01 | 7:49a | OCMetaMgr_setSelectedStudyProps( ).gif |
| 6,337 | 02-27-01 | 4:48a | OCDataMgr_the( ).gif |
| 11,939 | 02-12-01 | 7:49a | OCMetaMgr_writeOCMetaPacketToFile( ).gif |
| 2,004 | 02-12-01 | 7:49a | OCMetaMgr_getOCHostUrl( ).gif |
| 3,708 | 02-27-01 | 4:48a | OCDataMgr_getOCDataEvents( ).gif |
| 27,485 | 02-27-01 | 4:48a | OCDataMgr_getOCHostUrl( ).gif |
| 2,229 | 02-12-01 | 7:49a | OCMetaMgr_setCurrentMetaPacket(0).gif |
| 2,340 | 02-12-01 | 7:49a | OCMetaMgr_setCurrentMetaPacket(1).gif |
| 18,692 | 02-12-01 | 7:49a | OCMetaMgr_readTabularOCMetaPacket( ).gif |
| 9,904 | 02-12-01 | 7:49a | OCMetaMgr_setCurrentACPacket( ).gif |
| 34,600 | 02-12-01 | 7:49a | OCMetaMgr_getCurrentStudyId( ).gif |
| 2,064 | 02-27-01 | 4:48a | OCDataMgr_isUsingTestMode( ).gif |
| 2,272 | 02-12-01 | 7:49a | OCMetaMgr_getGlobalLibraryTableNames( ).gif |
| 2,272 | 02-12-01 | 7:49a | OCMetaMgr_getCurrentMetaPacket( ).gif |
| 3,156 | 02-12-01 | 7:49a | OCMetaMgr_getOcSystemVersion( ).gif |
| 85,235 | 02-12-01 | 7:49a | OCMetaMgr_retrieveOCMetaPacket( ).gif |
| 11,499 | 02-27-01 | 4:48a | ocdata.gif |
| 37,098 | 02-27-01 | 4:48a | OCDataMgr_connectAndDisconnect( ).gif |
| 39,149 | 02-27-01 | 4:48a | OCDataMgr_connectOCL( ).gif |
| 11,509 | 02-27-01 | 4:48a | OCDataMgr_disconnectOCL( ).gif |
| 2,780 | 02-27-01 | 4:48a | OCDataMgr_getCurrentACPacket( ).gif |
| 12,832 | 02-27-01 | 4:48a | OCDataMgr_readOCDataPacketFile( ).gif |
| 19,328 | 02-12-01 | 7:49a | OCMetaMgr_readOCMetaPacketFile( ).gif |
| 2,259 | 02-27-01 | 4:48a | OCDataMgr_getCurrentDataPacket( ).gif |
| 4,731 | 02-12-01 | 7:49a | OCMetaMgr_isTable( ).gif |
| 29,545 | 02-12-01 | 7:49a | OCMetaMgr_retrieveDciBookStatusCode( ).gif |
| 9,625 | 02-27-01 | 4:48a | OCDataMgr_writeOCDataTablesToFile( ).gif |
| 2,239 | 02-27-01 | 4:48a | OCDataMgr_setCurrentDataPacket( ).gif |
| 4,777 | 02-12-01 | 7:49a | ocmeta.gif |
| 24,220 | 02-12-01 | 7:49a | OCMetaMgr_announceNewMetadata( ).gif |
| 3,268 | 02-12-01 | 7:49a | OCMetaMgr_getAllMetadataTables( ).gif |
| 200,134 | 02-12-01 | 7:49a | OCMetaMgr_getConnection( ).gif |
| 2,792 | 02-12-01 | 7:49a | OCMetaMgr_getCurrentACPacket( ).gif |
| 2,199 | 02-21-01 | 7:43a | patient_data.html |
| 3,592 | 02-27-01 | 4:51a | patientdata_translator.html |
| 3,366 | 02-27-01 | 4:50a | patientdata_1.gif |
| 8,709 | 02-27-01 | 4:51a | patientdata_ocdata.html |
| 1,947 | 02-27-01 | 4:50a | patientdata_2.gif |
| 9,146 | 02-27-01 | 4:51a | patientdata_overview.html |
| 2,503 | 02-27-01 | 4:50a | patientdata_3.gif |
| 12,135 | 02-27-01 | 4:51a | patientdata_studysite.html |
| 2,577 | 02-27-01 | 4:50a | patientdata_4.gif |
| 7,896 | 02-27-01 | 4:51a | patientdata_tmdata.html |
| 235,862 | 04-11-01 | 3:39a | Process.runCycle.gif |
| 8,884 | 01-04-01 | 5:54p | properties_ui_class.gif |
| 10,082 | 01-15-01 | 12:08p | property_ui_class.gif |
| 25,000 | 01-22-01 | 11:49a | RDE_server_class.gif |
| 11,476 | 01-22-01 | 11:49a | RDE_Server_component.gif |
| 4,549 | 02-23-01 | 1:36p | security.html |
| 2,081 | 02-27-01 | 4:52a | StudySiteMgr_getStudyMap( ).gif |
| 2,287 | 02-27-01 | 4:52a | StudySiteMgr_getCurrentDataPacket( ).gif |
| 9,526 | 02-27-01 | 4:52a | StudySiteMgr_writeDciQualifierToFile( ).gif |
| 2,067 | 02-27-01 | 4:52a | StudySiteMgr_getCurrentStudyId( ).gif |

TABLE 1-continued

Contents of the Computer Program Listing Appendix

| | | | |
|---|---|---|---|
| 7,771 | 02-27-01 | 4:52a | StudySiteMgr__readTabularStudySiteDataPac.gif |
| 16,078 | 02-27-01 | 4:52a | StudySiteMgr__getOcInvestigators(0).gif |
| 10,983 | 02-27-01 | 4:52a | StudySiteMgr__getOcInvestigators(1).gif |
| 60,024 | 02-27-01 | 4:52a | StudySiteMgr__retrieveOcPhaseForStudy( ).gif |
| 7,500 | 02-27-01 | 4:52a | StudySiteMgr__readDciQualifierFile( ).gif |
| 8,573 | 02-27-01 | 4:52a | StudySiteMgr__the( ).gif |
| 18,794 | 02-27-01 | 4:52a | StudySiteMgr__getOcSites( ).gif |
| 19,207 | 02-27-01 | 4:52a | StudySiteMgr__getOcPatients( ).gif |
| 3,036 | 02-27-01 | 4:52a | StudySiteMgr__setCurrentACPacket( ).gif |
| 9,705 | 02-27-01 | 4:52a | StudySiteMgr__writeStudySiteDataTablesToF.gif |
| 21,151 | 02-27-01 | 4:52a | StudySiteMgr__retrieveTmPhaseForStudy( ).gif |
| 40,379 | 02-27-01 | 4:52a | StudySiteMgr__update( ).gif |
| 12,025 | 02-27-01 | 4:52a | StudySiteMgr__writeStudySiteDataPacketToF.gif |
| 28,642 | 02-27-01 | 4:52a | StudySiteMgr__retrieveDciQualifier( ).gif |
| 3,797 | 02-27-01 | 4:52a | StudySiteMgr__getStudySiteEvents( ).gif |
| 2,062 | 02-27-01 | 4:52a | StudySiteMgr__getProperties( ).gif |
| 13,074 | 02-27-01 | 4:52a | StudySiteMgr__readStudySiteDataPacketFile.gif |
| 2,077 | 02-27-01 | 4:52a | StudySiteMgr__getCurrentPatientTypes( ).gif |
| 234,887 | 02-27-01 | 4:52a | StudySiteMgr__main( ).gif |
| 179,732 | 02-27-01 | 4:52a | StudySiteMgr__updatePatientMapFromData( ).gif |
| 2,081 | 02-27-01 | 4:52a | StudySiteMgr__getCurrentStudyName( ).gif |
| 31,188 | 03-26-01 | 1:57a | storage_overview.html |
| 13,129 | 02-27-01 | 4:52a | studysite.gif |
| 93,556 | 02-27-01 | 4:52a | StudySiteMgr__createStudySitePacket( ).gif |
| 8,085 | 02-27-01 | 4:52a | StudySiteMgr__createValueData( ).gif |
| 2,815 | 02-27-01 | 4:52a | StudySiteMgr__getCurrentACPacket( ).gif |
| 7,759 | 01-15-01 | 10:07a | study_chooser_design.gif |
| 9,715 | 01-15-01 | 10:07a | study_panel_design.gif |
| 13,806 | 01-15-01 | 12:06p | study_status_ui_class.gif |
| 7,612 | 01-04-01 | 5:54p | study_status_ui_detail.gif |
| 5,010 | 01-15-01 | 12:06p | system_status_ui_detail.gif |
| 10,463 | 01-15-01 | 12:06p | system_events_ui_class.gif |
| 6,722 | 01-04-01 | 5:54p | system_events_ui_detail.gif |
| 8,112 | 01-15-01 | 12:08p | system_messages_ui_class.gif |
| 11,012 | 01-15-01 | 12:06p | system_status_ui_class.gif |
| 11,965 | 02-12-01 | 7:49a | TMMetaMgr__writeTMMetaPacketToFile( ).gif |
| 26,561 | 02-27-01 | 4:53a | TMDataMgr__writePacketToTabularFile( ).gif |
| 19,700 | 02-12-01 | 7:49a | TMMetaMgr__getCurrentStudyId( ).gif |
| 9,899 | 02-12-01 | 7:49a | TMMetaMgr__setCurrentACPacket( ).gif |
| 46,633 | 02-27-01 | 4:53a | TMDataMgr__update( ).gif |
| 22,916 | 02-12-01 | 7:49a | TMMetaMgr__getCurrentStudyName( ).gif |
| 8,329 | 02-12-01 | 7:49a | TMMetaMgr__readEdiMetadataFile( ).gif |
| 16,921 | 02-27-01 | 4:53a | TMDataMgr__writePacketToPRDFile( ).gif |
| 3,183 | 02-12-01 | 7:49a | TMMetaMgr__getDefaultTmVersion( ).gif |
| 14,141 | 02-12-01 | 7:49a | TMMetaMgr__readTabularTMMetaPacket( ).gif |
| 45,635 | 02-12-01 | 7:49a | TMMetaMgr__writeMetadataToEdiFile(1).gif |
| 13,804 | 02-12-01 | 7:49a | TMMetaMgr__writeMetadataToEdiFile(0).gif |
| 14,081 | 02-27-01 | 4:53a | TMDataMgr__readPacketTabularFile( ).gif |
| 4,951 | 02-12-01 | 7:49a | TMMetaMgr__the( ).gif |
| 2,272 | 02-12-01 | 7:49a | TMMetaMgr__setSelectedStudyProps( ).gif |
| 2,199 | 02-12-01 | 7:49a | TMMetaMgr__getSelectedStudyProps( ).gif |
| 2,047 | 02-27-01 | 4:53a | TMDataMgr__getCurrentTmVersion( ).gif |
| 9,964 | 02-12-01 | 7:49a | TMMetaMgr__isFieldTextType( ).gif |
| 29,920 | 02-12-01 | 7:49a | TMMetaMgr__readEdiMetadataFile(1).gif |
| 2,144 | 02-27-01 | 4:53a | TMDataMgr__setCurrentTmVersion( ).gif |
| 9,739 | 02-27-01 | 4:53a | TMDataMgr__getCurrentStudyName( ).gif |
| 27,642 | 02-12-01 | 7:49a | TMMetaMgr__getStudyProperties( ).gif |
| 30,830 | 02-12-01 | 7:49a | TMMetaMgr__update( ).gif |
| 39,792 | 02-27-01 | 4:53a | TMDataMgr__main( ).gif |
| 5,141 | 02-12-01 | 7:49a | TMMetaMgr__getSegmentFieldNames( ).gif |
| 2,247 | 02-12-01 | 7:49a | TMMetaMgr__getCurrentMetaPacket( ).gif |
| 2,173 | 02-27-01 | 4:53a | TMDataMgr__readPacketFile( ).gif |
| 2,230 | 02-12-01 | 7:49a | TMMetaMgr__setCurrentMetaPacket( ).gif |
| 2,897 | 02-27-01 | 4:53a | TMDataMgr__setCurrentACPacket( ).gif |
| 19,012 | 02-12-01 | 7:49a | TMMetaMgr__readTMMetaPacketFile( ).gif |
| 2,008 | 02-12-01 | 7:49a | TMMetaMgr__getProperties( ).gif |
| 2,029 | 02-27-01 | 4:53a | TMDataMgr__getProperties( ).gif |
| 2,240 | 02-27-01 | 4:53a | TMDataMgr__setCurrentDataPacket( ).gif |
| 5,918 | 02-12-01 | 7:49a | TMMetaMgr__getFieldSize( ).gif |
| 10,173 | 02-12-01 | 7:49a | TMMetaMgr__getIndexForSegmentField( ).gif |
| 5,671 | 02-27-01 | 4:53a | TMDataMgr__the( ).gif |
| 4,955 | 02-27-01 | 4:53a | tmdata.gif |
| 1,893 | 02-27-01 | 4:53a | TMDataMgr__dispose( ).gif |
| 2,782 | 02-27-01 | 4:53a | TMDataMgr__getCurrentACPacket( ).gif |
| 2,251 | 02-27-01 | 4:53a | TMDataMgr__getCurrentDataPacket( ).gif |
| 9,609 | 02-27-01 | 4:53a | TMDataMgr__getCurrentStudyId( ).gif |
| 9,763 | 02-27-01 | 4:53a | TMDataMgr__writePacketToFile( ).gif |

TABLE 1-continued

Contents of the Computer Program Listing Appendix

| | | | |
|---|---|---|---|
| 16,280 | 02-12-01 | 7:49a | TMMetaMgr__writeTMMetaTablesToFile( ).gif |
| 19,445 | 02-27-01 | 4:53a | TMDataMgr__initPacketFromHeader( ).gif |
| 39,660 | 02-27-01 | 4:53a | TMDataMgr__readPacketPRDFile( ).gif |
| 3,979 | 02-12-01 | 7:49a | tmmeta.gif |
| 31,650 | 02-12-01 | 7:49a | TMMetaMgr__announceNewMetadata( ).gif |
| 2,243 | 02-12-01 | 7:49a | TMMetaMgr__dispose( ).gif |
| 3,270 | 02-12-01 | 7:49a | TMMetaMgr__getAllMetadataTables( ).gif |
| 2,791 | 02-12-01 | 7:49a | TMMetaMgr__getCurrentACPacket( ).gif |
| 9,689 | 01-04-01 | 5:54p | tools__menu__class.gif |
| 7,081 | 01-15-01 | 12:08p | tools__menu__ui__class.gif |
| 2,915 | 02-27-01 | 4:54a | TranslatorMgr__the( ).gif |
| 2,114 | 02-27-01 | 4:54a | TranslatorMgr__update( ).gif |
| 22,982 | 02-27-01 | 4:54a | translator.gif |
| 4,247 | 02-27-01 | 4:54a | TranslatorMgr__getSkippedValueCode( ).gif |
| 3,744 | 02-27-01 | 4:54a | TranslatorMgr__getTranslateEvents( ).gif |
| 31,541 | 02-27-01 | 4:54a | TranslatorMgr__initializeForStudyMap( ).gif |
| 5,836 | 02-27-01 | 4:54a | TranslatorMgr__isAddingTimeToResponses( ).gif |
| 5,535 | 02-27-01 | 4:54a | TranslatorMgr__isHandlingTriggers( ).gif |
| 58,638 | 02-27-01 | 4:54a | TranslatorMgr__translateTmData( ).gif |
| 67,787 | 03-01-01 | 6:37a | Unjar.run.gif |
| 7,436 | 01-04-01 | 5:54p | update__server__status__detail.gif |
| 6,172 | 01-15-01 | 12:08p | update__system__events__ui__detail.gif |
| 5,440 | 01-04-01 | 5:54p | update__system__event__detail.gif |
| 8,092 | 01-15-01 | 12:08p | update__system__status__ui__detail.gif |
| 13,718 | 02-20-01 | 12:51a | wip__package.gif |
| Directory of D:\GGB__1.2.1\com\roche\rde\wip\doc-files\CVS | | | |
| 25,373 | 05-03-02 | 4:24p | Entries |
| 60 | 05-03-02 | 4:23p | Repository |
| 53 | 05-03-02 | 4:23p | Root |
| Directory of D:\GGB__1.2.1\com\roche\rde\wip\exec | | | |
| 13,613 | 03-28-02 | 6:20a | ACExecEvent.java |
| 3,493 | 12-19-00 | 5:56p | ActivityEvent.java |
| 30,555 | 10-19-01 | 5:04a | ConsoleApi.java |
| 26,562 | 05-03-02 | 4:26p | ConsoleApi__Stub.java |
| <DIR> | 05-03-02 | 4:24p | CVS |
| <DIR> | 05-03-02 | 4:24p | doc-files |
| 4,644 | 12-19-00 | 5:56p | ErrorEvent.java |
| 4,522 | 12-19-00 | 5:56p | ExecActivator.java |
| 48,328 | 05-03-02 | 7:36a | ExecCli.java |
| 29,964 | 05-03-02 | 4:26p | ExecCli__Stub.java |
| 6,751 | 12-19-00 | 5:56p | ExecFileNode.java |
| 63,431 | 05-03-02 | 7:36a | ExecMgr.java |
| 21,846 | 04-10-02 | 3:29a | ExecMgrTest.java |
| 1,889 | 04-05-02 | 5:19a | Exec.properties |
| 1,997 | 12-22-00 | 3:02p | HeartbeatEvent.java |
| 1,333 | 12-22-00 | 3:02p | IAuthorization.java |
| 12,068 | 01-24-01 | 5:09a | IConsoleApi.java |
| 9,182 | 04-05-02 | 5:19a | IExecCli.java |
| 3,575 | 12-22-00 | 3:02p | IMapExec.java |
| 1,353 | 12-22-00 | 3:02p | InvalidDateException.java |
| 1,153 | 12-22-00 | 3:02p | InvalidStudyException.java |
| 1,213 | 12-22-00 | 3:02p | InvalidStudySiteException.java |
| 11,739 | 12-22-00 | 3:02p | LogBook.java |
| 14,526 | 07-20-01 | 2:48a | Logon.java |
| 8,760 | 10-29-01 | 5:02a | Mailer.java |
| 8,600 | 02-13-01 | 7:39a | MapExecApi.java |
| 11,649 | 05-03-02 | 4:26p | MapExecApi__Stub.java |
| 1,785 | 05-04-01 | 2:56p | OCException.java |
| 18,637 | 04-11-01 | 1:54a | package.html |
| 1,072 | 12-22-00 | 3:02p | PatientMapException.java |
| 3,274 | 07-16-01 | 9:17a | PermissionDeniedEvent.java |
| 2,336 | 12-22-00 | 3:02p | PermissionGrantedEvent.java |
| 2,767 | 12-22-00 | 3:02p | ProcessTimer.java |
| 82,666 | 05-03-02 | 7:36a | Process.java |
| 1,196 | 12-22-00 | 3:02p | ProcessException.java |
| 5,950 | 12-22-00 | 3:02p | ProcessStatistic.java |
| 7,551 | 05-04-01 | 7:35a | ProcessThread.java |
| 117 | 07-21-00 | 9:36a | rmi.bat |
| 3,209 | 05-03-02 | 7:36a | ServerStatusEvent.java |
| 3,907 | 01-23-01 | 1:54a | ServerState.java |
| 1,779 | 12-22-00 | 3:02p | ServerCommandType.java |
| 5,146 | 07-16-01 | 9:17a | ServerPermissionEvent.java |
| 2,502 | 12-22-00 | 3:02p | ServerProcessEvent.java |
| 2,107 | 12-22-00 | 3:02p | ServerResponseEvent.java |
| 4,511 | 12-22-00 | 3:02p | SilentEvent.java |
| 81,484 | 05-03-02 | 7:36a | StatusAccountMgr.java |
| 649 | 10-13-00 | 12:21p | StatusAccount.properties |

TABLE 1-continued

Contents of the Computer Program Listing Appendix

| | | | |
|---|---|---|---|
| 24,471 | 12-22-00 | 3:02p | StatusAccountPacket.java |
| 1,380 | 12-22-00 | 3:02p | StudyAlreadyExistsException.java |

Directory of D:\GGB_1.2.1\com\roche\rde\wip\exec\CVS

| | | | |
|---|---|---|---|
| 2,334 | 05-03-02 | 4:24p | Entries |
| 19 | 05-03-02 | 4:24p | Entries.Log |
| 55 | 05-03-02 | 4:24p | Repository |
| 53 | 05-03-02 | 4:24p | Root |

Directory of D:\GGB_1.2.1\com\roche\rde\wip\exec\doc-files

| | | | |
|---|---|---|---|
| <DIR> | 05-03-02 | 4:24p | CVS |
| 304,309 | 01-25-01 | 7:24a | exec.gif |

Directory of D:\GGB_1.2.1\com\roche\rde\wip\exec\doc-files\CVS

| | | | |
|---|---|---|---|
| 48 | 05-03-02 | 4:24p | Entries |
| 65 | 05-03-02 | 4:24p | Repository |
| 53 | 05-03-02 | 4:24p | Root |

Directory of D:\GGB_1.2.1\com\roche\rde\wip\graphics

| | | | |
|---|---|---|---|
| 7,383 | 01-31-00 | 5:38p | ACFrame.java |
| 15,982 | 04-19-00 | 4:41p | ACFrameVwr.java |
| 957 | 09-20-99 | 12:25p | AWTButton.java |
| 1,961 | 02-19-99 | 12:04a | BorderFilter.java |
| 13,936 | 09-17-99 | 3:58p | BorderPanel.java |
| <DIR> | 05-03-02 | 4:24p | CVS |
| <DIR> | 05-03-02 | 4:24p | doc-files |
| 4,515 | 01-07-00 | 8:32p | FieldEntryDialog.java |
| 7,335 | 09-20-99 | 12:25p | GraphButton.java |
| 922 | 09-20-99 | 12:25p | IButton.java |
| 5,491 | 01-07-00 | 8:32p | LoginDialog.java |
| 3,787 | 01-27-00 | 11:47a | OKDialog.java |
| 701 | 01-10-01 | 11:20a | package.html |
| 5,494 | 09-20-99 | 12:25p | PadEdgeFilter.java |
| 4,804 | 09-20-99 | 12:25p | PercentLayout.java |
| 23,051 | 04-22-02 | 11:09a | ProgressBar.java |
| 5,560 | 04-19-00 | 4:41p | PropertiesDialog.java |
| 4,750 | 04-19-00 | 4:41p | SelectionDialog.java |
| 2,524 | 09-20-99 | 12:25p | SimpleMenu.java |
| 3,725 | 09-20-99 | 12:25p | StatusPanel.java |
| 1,729 | 09-20-99 | 12:25p | TintFilter.java |
| 6,939 | 08-12-99 | 9:42a | WidgetMaker.java |
| 3,795 | 01-07-00 | 8:32p | YesNoDialog.java |

Directory of D:\GGB_1.2.1\com\roche\rde\wip\graphics\CVS

| | | | |
|---|---|---|---|
| 1,053 | 05-03-02 | 4:24p | Entries |
| 19 | 05-03-02 | 4:24p | Entries.Log |
| 59 | 05-03-02 | 4:24p | Repository |
| 53 | 05-03-02 | 4:24p | Root |

Directory of D:\GGB_1.2.1\com\roche\rde\wip\graphics\doc-files

| | | | |
|---|---|---|---|
| <DIR> | 05-03-02 | 4:24p | CVS |
| 22,966 | 01-10-01 | 12:15p | graphics.gif |

Directory of D:\GGB_1.2.1\com\roche\rde\wip\graphics\doc-files\CVS

| | | | |
|---|---|---|---|
| 52 | 05-03-02 | 4:24p | Entries |
| 69 | 05-03-02 | 4:24p | Repository |
| 53 | 05-03-02 | 4:24p | Root |

Directory of D:\GGB_1.2.1\com\roche\rde\wip\install

| | | | |
|---|---|---|---|
| 8,480 | 10-26-01 | 7:27a | ACInstallGui.java |
| 34,161 | 10-26-01 | 7:27a | Configurator.java |
| <DIR> | 05-03-02 | 4:24p | CVS |
| <DIR> | 05-03-02 | 4:24p | doc-files |
| 24,915 | 06-28-01 | 2:32a | Installer.java |
| 2,313 | 10-29-01 | 5:02a | Install.properties |
| 6,561 | 04-10-02 | 4:16a | InstallTest.java |
| 5,051 | 03-01-01 | 9:07a | package.html |
| 9,363 | 03-21-01 | 8:38a | Unjar.java |

Directory of D:\GGB_1.2.1\com\roche\rde\wip\install\CVS

| | | | |
|---|---|---|---|
| 349 | 05-03-02 | 4:24p | Entries |
| 19 | 05-03-02 | 4:24p | Entries.Log |
| 58 | 05-03-02 | 4:24p | Repository |
| 53 | 05-03-02 | 4:24p | Root |

Directory of D:\GGB_1.2.1\com\roche\rde\wip\install\doc-files

| | | | |
|---|---|---|---|
| <DIR> | 05-03-02 | 4:24p | CVS |
| 35,217 | 01-26-01 | 2:35a | install.gif |

Directory of D:\GGB_1.2.1\com\roche\rde\wip\install\doc-files\CVS

| | | | |
|---|---|---|---|
| 51 | 05-03-02 | 4:24p | Entries |
| 68 | 05-03-02 | 4:24p | Repository |
| 53 | 05-03-02 | 4:24p | Root |

Directory of D:\GGB_1.2.1\com\roche\rde\wip\metamapper

| | | | |
|---|---|---|---|
| 2,811 | 09-01-00 | 10:23a | ACMetaElement.java |
| 1,520 | 02-05-00 | 1:37p | ACMetaIndex.java |
| 14,930 | 05-02-02 | 7:34p | ArezzoVocab.java |
| <DIR> | 05-03-02 | 4:24p | CVS |

TABLE 1-continued

Contents of the Computer Program Listing Appendix

| | | | |
|---|---|---|---|
| 6,391 | 12-03-99 | 10:00a | DataTypeChooser.java |
| 5,302 | 09-20-99 | 12:26p | DciTemplate.java |
| 20,442 | 11-13-00 | 1:27p | DcmQualifier.java |
| <DIR> | 05-03-02 | 4:24p | doc-files |
| 2,268 | 01-12-00 | 6:47p | ECrfCoordinate.java |
| 2,912 | 03-22-00 | 5:44p | Formatter.java |
| 28,520 | 09-21-01 | 7:27a | GroupRepeater.java |
| 28,765 | 08-10-01 | 8:07p | LayoutAdjuster.java |
| 3,704 | 09-05-00 | 6:11p | MapException.java |
| 39,216 | 07-11-01 | 2:41a | MapMgr.java |
| 16,093 | 04-10-02 | 4:16a | MapMgrTest.java |
| 68,910 | 04-29-02 | 2:17a | MapUpdater.java |
| 8,260 | 07-18-01 | 3:25a | Map.properties |
| 15,091 | 02-09-01 | 7:07a | MetaElementRegistry.java |
| 12,913 | 10-10-00 | 3:02p | OcClinicalPlannedEvent.java |
| 4,696 | 05-07-00 | 3:59p | OcClinicalStudy.java |
| 3,622 | 08-10-00 | 8:07p | OcDci.java |
| 9,598 | 10-09-00 | 7:02p | OcDcmLayout.java |
| 10,062 | 01-20-00 | 11:26a | OcDcmLayoutPage.java |
| 2,734 | 10-09-00 | 7:02p | OcDcmQuesRepeatDefault.java |
| 16,156 | 07-11-01 | 7:18a | OcDcmQuestion.java |
| 9,210 | 05-30-01 | 1:05p | OcDcmQuestionGroup.java |
| 8,809 | 08-10-00 | 8:07p | OcDcm.java |
| 3,299 | 04-27-00 | 2:11p | OcMetaElement.java |
| 19,549 | 08-11-00 | 1:24p | OcMetaIndex.java |
| 5,443 | 08-14-00 | 12:53p | OCObjBuilder.java |
| 1,327 | 12-05-99 | 8:59p | OcScreenCoordinate.java |
| 87,353 | 04-02-02 | 10:21a | OcTmMapper.java |
| 9,442 | 07-11-01 | 2:41a | OcTmMetaIndex.java |
| 1,892 | 02-19-01 | 2:14a | package.html |
| 32,325 | 07-11-01 | 7:18a | PromptFinder.java |
| 8,484 | 06-06-01 | 7:02a | QuestionDefaulter.java |
| 74,125 | 07-12-01 | 3:39a | StudyMap.java |
| 2,876 | 11-09-00 | 8:25p | StudyUpdateEvent.java |
| 8,917 | 04-30-02 | 12:17p | TmClinicalTrial.java |
| 20,697 | 04-03-02 | 12:34p | TmCRFElement.java |
| 24,489 | 05-10-01 | 2:39a | TmCRFPage.java |
| 21,588 | 10-17-01 | 7:58a | TmDataItem.java |
| 3,156 | 08-10-00 | 8:07p | TmEnrollForm.java |
| 2,168 | 08-10-00 | 8:07p | TmEnrollVisit.java |
| 5,191 | 04-28-00 | 2:08p | TmMetaElement.java |
| 3,797 | 08-11-00 | 1:24p | TmMetaIndex.java |
| 30,070 | 09-03-00 | 4:25p | TMObjBuilder.java |
| 5,612 | 10-17-01 | 7:58a | TmStudyDefinition.java |
| 10,006 | 08-10-00 | 8:07p | TmStudyVisit.java |
| 4,322 | 04-21-00 | 5:50p | TmStudyVisitCRFPage.java |
| 3,955 | 10-17-01 | 7:58a | TmTrialStatusHistory.java |
| 8,946 | 04-03-02 | 3:48a | TmValueData.java |
| 2,879 | 08-10-00 | 8:07p | TmVisitDateForm.java |
| 7,880 | 08-11-00 | 1:24p | WidgetChooser.java |
| Directory of D:\GGB_1.2.1\com\roche\rde\wip\metamapper\CVS | | | |
| 2,727 | 05-03-02 | 4:24p | Entries |
| 19 | 05-03-02 | 4:24p | Entries.Log |
| 61 | 05-03-02 | 4:24p | Repository |
| 53 | 05-03-02 | 4:24p | Root |
| Directory of D:\GGB_1.2.1\com\roche\rde\wip\metamapper\doc-files | | | |
| <DIR> | 05-03-02 | 4:24p | CVS |
| 98,656 | 01-10-01 | 12:14p | metamapper.gif |
| Directory of D:\GGB_1.2.1\com\roche\rde\wip\metamapper\doc-files\CVS | | | |
| 54 | 05-03-02 | 4:24p | Entries |
| 71 | 05-03-02 | 4:24p | Repository |
| 53 | 05-03-02 | 4:24p | Root |
| Directory of D:\GGB_1.2.1\com\roche\rde\wip\ocdata | | | |
| 4,968 | 04-05-02 | 6:42a | com_roche_rde_wip_ocdata_DcApi.h |
| <DIR> | 05-03-02 | 4:24p | CVS |
| 271,360 | 08-26-99 | 12:11p | dcapi.dll |
| 21,297 | 08-26-99 | 12:00p | dcapi.h |
| 24,992 | 08-26-99 | 12:03p | dcapi.lib |
| 20,832 | 04-05-02 | 6:42a | DcApi.java |
| 3,010 | 05-18-00 | 12:39p | delete_patient_data_1.sql |
| 2,267 | 05-24-00 | 12:24p | deleteDataNote.txt |
| <DIR> | 05-03-02 | 4:24p | doc-files |
| 24,339 | 04-05-02 | 6:42a | OCDataRecordLoader.java |
| 7,917 | 05-22-01 | 6:00a | OCDataTableReader.java |
| 16,827 | 04-02-02 | 10:19a | OCDataPacket.java |
| 6,326 | 10-31-00 | 9:38p | OCDataUtil.java |
| 1,798 | 11-09-00 | 8:25p | OCDataEvent.java |

TABLE 1-continued

Contents of the Computer Program Listing Appendix

| | | | |
|---|---|---|---|
| 2,614 | 04-02-02 | 10:07a | OCData.properties |
| 5,130 | 02-07-02 | 9:06a | OCDataLoadException.java |
| 30,681 | 05-03-02 | 8:01a | OCDataMgr.java |
| 12,924 | 04-10-02 | 5:17a | OCDataMgrTest.java |
| 4,850 | 09-05-00 | 9:16a | OCPatientRecordLoader.java |
| 4,757 | 01-10-01 | 11:21a | package.html |
| 2,272 | 04-02-00 | 6:16p | PatientRecord.java |
| 4,160 | 09-25-00 | 5:05p | RdciKeysRecord.java |
| 62,303 | 04-05-02 | 6:42a | wip_dcapi.c |
| 175,616 | 04-05-02 | 6:42a | wip_dcapi.dll |

Directory of D:\GGB_1.2.1\com\roche\rde\wip\ocdata\CVS

| | | | |
|---|---|---|---|
| 1,150 | 05-03-02 | 4:24p | Entries |
| 19 | 05-03-02 | 4:24p | Entries.Log |
| 57 | 05-03-02 | 4:24p | Repository |
| 53 | 05-03-02 | 4:24p | Root |

Directory of D:\GGB_1.2.1\com\roche\rde\wip\ocdata\doc-files

| | | | |
|---|---|---|---|
| <DIR> | 05-03-02 | 4:24p | CVS |
| 11,499 | 01-15-01 | 9:57a | ocdata.gif |

Directory of D:\GGB_1.2.1\com\roche\rde\wip\ocdata\doc-files\CVS

| | | | |
|---|---|---|---|
| 50 | 05-03-02 | 4:24p | Entries |
| 67 | 05-03-02 | 4:24p | Repository |
| 53 | 05-03-02 | 4:24p | Root |

Directory of D:\GGB_1.2.1\com\roche\rde\wip\ocmeta

| | | | |
|---|---|---|---|
| <DIR> | 05-03-02 | 4:24p | CVS |
| 9,281 | 05-03-02 | 8:32a | DciBookPageCleaner.java |
| 11,025 | 10-20-99 | 9:37a | DciJudge.java |
| <DIR> | 05-03-02 | 4:24p | doc-files |
| 1,391 | 03-28-02 | 9:11a | IncompleteStudyException.java |
| 22,111 | 03-29-02 | 3:16a | OCMetaMgr.java |
| 12,745 | 10-18-01 | 11:45a | OCMeta.properties |
| 17,289 | 04-10-02 | 5:17a | OCMetaMgrTest.java |
| 12,724 | 07-11-01 | 7:16a | OCMetaPacket.java |
| 49,806 | 04-22-02 | 12:08p | OCTableReader.java |
| 1,054 | 01-10-01 | 11:50a | package.html |

Directory of D:\GGB_1.2.1\com\roche\rde\wip\ocmeta\CVS

| | | | |
|---|---|---|---|
| 475 | 05-03-02 | 4:24p | Entries |
| 19 | 05-03-02 | 4:24p | Entries.Log |
| 57 | 05-03-02 | 4:24p | Repository |
| 53 | 05-03-02 | 4:24p | Root |

Directory of D:\GGB_1.2.1\com\roche\rde\wip\ocmeta\doc-files

| | | | |
|---|---|---|---|
| <DIR> | 05-03-02 | 4:24p | CVS |
| 4,777 | 01-10-01 | 12:13p | ocmeta.gif |

Directory of D:\GGB_1.2.1\com\roche\rde\wip\ocmeta\doc-files\CVS

| | | | |
|---|---|---|---|
| 50 | 05-03-02 | 4:24p | Entries |
| 67 | 05-03-02 | 4:24p | Repository |
| 53 | 05-03-02 | 4:24p | Root |

Directory of D:\GGB_1.2.1\com\roche\rde\wip\peer

| | | | |
|---|---|---|---|
| 4,612 | 07-23-01 | 7:49a | ACPeer.java |
| 7,612 | 02-08-01 | 6:55a | ACRmiPeer.java |
| <DIR> | 05-03-02 | 4:24p | CVS |
| <DIR> | 05-03-02 | 4:24p | doc-files |
| 1,009 | 02-08-01 | 6:55a | IACBot.java |
| 1,826 | 02-08-01 | 6:55a | IClient.java |
| 1,138 | 02-08-01 | 6:55a | IRdeBot.java |
| 2,932 | 02-08-01 | 6:55a | IRmiService.java |
| 836 | 02-08-01 | 6:55a | IRmiTestSvr.java |
| 1,319 | 02-08-01 | 6:55a | IServer.java |
| 7,454 | 02-20-01 | 4:57a | package.html |
| 2,275 | 05-03-02 | 7:35a | PeerException.java |
| 302 | 07-23-01 | 9:24a | Peer.properties |
| 131 | 08-08-00 | 2:33p | rmi.bat |
| 6,178 | 02-08-01 | 6:55a | RmiActivatableService.java |
| 7,133 | 05-03-02 | 4:26p | RmiActivatableService_Stub.java |
| 4,604 | 02-08-01 | 6:55a | RmiClient.java |
| 7,303 | 02-09-01 | 9:17a | RmiServer.java |
| 9,521 | 05-18-01 | 3:07a | RmiService.java |
| 7,111 | 05-03-02 | 4:26p | RmiService_Stub.java |
| 3,049 | 04-10-02 | 11:20a | RmiTest.java |
| 4,155 | 02-09-01 | 9:17a | RmiTestClient.java |
| 3,561 | 07-23-01 | 7:51a | RmiTestSvr.java |
| 7,853 | 05-03-02 | 4:26p | RmiTestSvr_Stub.java |

Directory of D:\GGB_1.2.1\com\roche\rde\wip\peer\CVS

| | | | |
|---|---|---|---|
| 924 | 05-03-02 | 4:24p | Entries |
| 19 | 05-03-02 | 4:24p | Entries.Log |
| 55 | 05-03-02 | 4:24p | Repository |
| 53 | 05-03-02 | 4:24p | Root |

Directory of D:\GGB_1.2.1\com\roche\rde\wip\peer\doc-files

TABLE 1-continued

Contents of the Computer Program Listing Appendix

| | | | |
|---|---|---|---|
| <DIR> | 05-03-02 | 4:24p | CVS |
| 97,736 | 01-26-01 | 5:40a | peer.gif |

Directory of D:\GGB_1.2.1\com\roche\rde\wip\peer\doc-files\CVS

| | | | |
|---|---|---|---|
| 48 | 05-03-02 | 4:24p | Entries |
| 65 | 05-03-02 | 4:24p | Repository |
| 53 | 05-03-02 | 4:24p | Root |

Directory of D:\GGB_1.2.1\com\roche\rde\wip\rdesim

| | | | |
|---|---|---|---|
| 2,762 | 11-05-99 | 3:15p | ACDataGenerator.java |
| 14,539 | 02-05-00 | 1:37p | ACRdeSimMgr.java |
| 13,193 | 12-01-99 | 5:16p | ConfigHelper.java |
| <DIR> | 05-03-02 | 4:24p | CVS |
| 15,429 | 11-05-99 | 3:15p | OCDataGenerator.java |
| 1,332 | 02-19-01 | 5:41a | package.html |
| 37,097 | 02-05-00 | 1:37p | RdeOCSimMgr.java |
| 38,522 | 05-31-00 | 2:05p | RdeSimLsnr.java |
| 1,921 | 10-18-99 | 4:55p | RdeSim.properties |
| 13,420 | 04-10-02 | 5:17a | RdeSimTest.java |
| 4,527 | 05-18-00 | 1:00p | RdeSimulator.java |
| 21,252 | 10-08-99 | 9:04a | RdeSimVwr.java |
| 19,125 | 05-31-00 | 2:05p | RdeTMSimMgr.java |
| 23,574 | 03-22-00 | 5:44p | TMDataGenerator.java |

Directory of D:\GGB_1.2.1\com\roche\rde\wip\rdesim\CVS

| | | | |
|---|---|---|---|
| 668 | 05-03-02 | 4:24p | Entries |
| 57 | 05-03-02 | 4:24p | Repository |
| 53 | 05-03-02 | 4:24p | Root |

Directory of D:\GGB_1.2.1\com\roche\rde\wip\rdesvr

| | | | |
|---|---|---|---|
| 5,452 | 10-18-00 | 4:32a | ACLock.java |
| 19,431 | 05-04-01 | 7:35a | ACMacroApi.java |
| 16,629 | 02-02-01 | 7:12a | ACRule.java |
| 9,985 | 05-14-00 | 6:22p | ACRuleCrossTableCheck.java |
| <DIR> | 05-03-02 | 4:24p | api |
| <DIR> | 05-03-02 | 4:24p | CVS |
| 3,140 | 10-18-00 | 10:48a | DBAndFileLock.java |
| <DIR> | 05-03-02 | 4:24p | dbconnect |
| 6,218 | 10-18-00 | 5:39a | DBLock.java |
| <DIR> | 05-03-02 | 4:24p | doc-files |
| 11,624 | 10-18-00 | 4:36a | FileLock.java |
| 2,681 | 07-06-01 | 3:33a | FindRdeServer.java |
| 492 | 05-04-01 | 5:56p | ICRFPageDataItemVisitIdRule.java |
| 463 | 07-12-00 | 5:05p | IGetRow.java |
| 4,606 | 07-23-01 | 1:21a | IMacroDataApi.java |
| 1,821 | 07-23-01 | 1:21a | IMacroGgbApi.java |
| 1,506 | 07-23-01 | 1:21a | IMacroMetaApi.java |
| 864 | 05-15-00 | 8:39a | InvalidCheckValuesException.java |
| 751 | 07-20-00 | 5:09p | IPageItemVisitCheck.java |
| 1,092 | 07-06-01 | 3:37a | IRdeBot.java |
| 608 | 05-14-00 | 6:23p | IRule.java |
| 1,095 | 07-23-01 | 1:22a | IStudySiteApi.java |
| 798 | 07-20-00 | 5:09p | ITrialVisitPageItemCheck.java |
| 122,363 | 04-02-02 | 10:18a | MacroDataApi.java |
| 18,560 | 04-02-02 | 10:16a | MacroGgbApi.java |
| 18,729 | 01-28-01 | 11:19p | MacroMetaApi.java |
| 12,239 | 01-18-01 | 4:27a | package.html |
| 2,361 | 05-02-01 | 3:47a | RdeActivator.java |
| 964 | 10-09-00 | 11:51a | RdeDatabaseLockException.java |
| 967 | 07-20-00 | 5:09p | RdeSiteNotFoundException.java |
| 971 | 07-20-00 | 5:09p | RdeStudyNotFoundException.java |
| 42,162 | 04-02-02 | 10:14a | RdeSvrMgr.java |
| 5,494 | 05-01-02 | 11:56a | RdeSvr.properties |
| 50,513 | 05-01-02 | 3:28a | RdeSvrMgrTest.java |
| 1,687 | 05-11-01 | 1:51a | RdeSvrTest.properties |
| 35,217 | 05-03-02 | 4:26p | RdeSvrMgr_Stub.java |
| <DIR> | 05-03-02 | 4:24p | rmi |
| 55 | 05-02-01 | 3:51a | rmi.bat |
| 838 | 05-11-00 | 5:06p | RowNotValidException.java |
| 1,937 | 08-30-00 | 12:40p | RuleClinicalTrial.java |
| 2,082 | 05-14-00 | 6:40p | RuleCRFElement.java |
| 1,979 | 05-14-00 | 6:40p | RuleCRFPage.java |
| 1,769 | 05-14-00 | 6:40p | RuleDataItem.java |
| 2,829 | 05-22-00 | 2:52p | RulePageItemVisit.java |
| 2,018 | 05-14-00 | 6:41p | RuleStudyVisit.java |
| 3,297 | 05-14-00 | 6:41p | RuleTrialVisitPageItem.java |
| 1,678 | 05-14-00 | 6:41p | RuleValueData.java |
| 5,799 | 02-04-02 | 8:42a | StudySiteApi.java |
| 21,081 | 05-02-02 | 11:31a | TmDbField.java |
| 2,558 | 07-20-00 | 5:09p | TmDbRow.java |

TABLE 1-continued

Contents of the Computer Program Listing Appendix

```
   5,367    02-02-01    7:18a    TmDbTable.java
   8,728    07-20-00    5:09p    TmTablePool.java
Directory of D:\GGB_1.2.1\com\roche\rde\wip\rdesvr\api
   <DIR>    05-03-02    4:24p    CVS
   <DIR>    05-03-02    4:24p    data
   <DIR>    05-03-02    4:24p    ggb
   <DIR>    05-03-02    4:24p    meta
Directory of D:\GGB_1.2.1\com\roche\rde\wip\rdesvr\api\CVS
       3    05-03-02    4:24p    Entries
      41    05-03-02    4:24p    Entries.Log
      61    05-03-02    4:24p    Repository
      53    05-03-02    4:24p    Root
Directory of D:\GGB_1.2.1\com\roche\rde\wip\rdesvr\api\data
   <DIR>    05-03-02    4:24p    CVS
Directory of D:\GGB_1.2.1\com\roche\rde\wip\rdesvr\api\data\CVS
       3    05-03-02    4:24p    Entries
      66    05-03-02    4:24p    Repository
      53    05-03-02    4:24p    Root
Directory of D:\GGB_1.2.1\com\roche\rde\wip\rdesvr\api\ggb
   <DIR>    05-03-02    4:24p    CVS
Directory of D:\GGB_1.2.1\com\roche\rde\wip\rdesvr\api\ggb\CVS
       3    05-03-02    4:24p    Entries
      65    05-03-02    4:24p    Repository
      53    05-03-02    4:24p    Root
Directory of D:\GGB_1.2.1\com\roche\rde\wip\rdesvr\api\meta
   <DIR>    05-03-02    4:24p    CVS
Directory of D:\GGB_1.2.1\com\roche\rde\wip\rdesvr\api\meta\CVS
       3    05-03-02    4:24p    Entries
      66    05-03-02    4:24p    Repository
      53    05-03-02    4:24p    Root
Directory of D:\GGB_1.2.1\com\roche\rde\wip\rdesvr\CVS
   2,427    05-03-02    4:24p    Entries
      64    05-03-02    4:24p    Entries.Log
      57    05-03-02    4:24p    Repository
      53    05-03-02    4:24p    Root
Directory of D:\GGB_1.2.1\com\roche\rde\wip\rdesvr\dbconnect
   <DIR>    05-03-02    4:24p    CVS
Directory of D:\GGB_1.2.1\com\roche\rde\wip\rdesvr\dbconnect\CVS
       3    05-03-02    4:24p    Entries
      67    05-03-02    4:24p    Repository
      53    05-03-02    4:24p    Root
Directory of D:\GGB_1.2.1\com\roche\rde\wip\rdesvr\doc-files
   <DIR>    05-03-02    4:24p    CVS
  38,137    01-10-01   12:12p    rdesvr.gif
Directory of D:\GGB_1.2.1\com\roche\rde\wip\rdesvr\doc-files\CVS
      50    05-03-02    4:24p    Entries
      67    05-03-02    4:24p    Repository
      53    05-03-02    4:24p    Root
Directory of D:\GGB_1.2.1\com\roche\rde\wip\rdesvr\rmi
   <DIR>    05-03-02    4:24p    CVS
Directory of D:\GGB_1.2.1\com\roche\rde\wip\rdesvr\rmi\CVS
       3    05-03-02    4:24p    Entries
      61    05-03-02    4:24p    Repository
      53    05-03-02    4:24p    Root
Directory of D:\GGB_1.2.1\com\roche\rde\wip\service
   <DIR>    05-03-02    4:24p    about
   8,966    08-31-01    6:54a    AboutSplash.java
   9,842    12-20-00    2:56p    ACSession.java
   7,039    03-30-01    3:47a    Authenticate.java
     507    08-27-01    4:34a    Authenticate.properties
   9,805    08-27-01    4:42a    AuthenticateLDAP.java
   7,689    07-20-01    2:30a    AuthenticateTEXT.java
     925    08-08-00    9:34a    blue-ball.gif
   5,333    01-19-01    3:54p    BusyThread.java
   <DIR>    05-03-02    4:27p    console
   <DIR>    05-03-02    4:24p    CVS
   <DIR>    05-03-02    4:24p    doc-files
   9,683    12-20-00    2:56p    ExampleFileFilter.java
   <DIR>    05-03-02    4:27p    exec
  28,086    10-17-01    8:49a    GenericClient.java
   3,657    12-20-00    2:56p    GGBTreePath.java
   2,930    05-03-02    4:26p    GGBTreePath_Stub.java
     886    08-08-00    9:34a    green-ball.gif
   1,480    07-19-01    9:26a    IAuthenticate.java
   1,174    12-20-00    2:56p    IDataConsumer.java
   1,382    12-20-00    5:01p    ILogon.java
   1,209    12-20-00    2:56p    ILogonClose.java
```

TABLE 1-continued

Contents of the Computer Program Listing Appendix

| | | | |
|---|---|---|---|
| 1,077 | 12-20-00 | 2:56p | InvalidSessionException.java |
| 1,744 | 12-20-00 | 2:56p | IProperty.java |
| 1,070 | 12-20-00 | 5:01p | IReconnect.java |
| 2,586 | 12-20-00 | 2:56p | IServiceWord.java |
| 2,756 | 12-20-00 | 2:56p | ISession.java |
| 1,083 | 12-20-00 | 2:56p | ITreeChildren.java |
| 2,006 | 12-20-00 | 2:56p | ITreePath.java |
| 1,035 | 12-21-00 | 9:44a | IUninstall.java |
| 4,187 | 12-20-00 | 5:01p | JStatusPanel.java |
| 8,815 | 12-20-00 | 5:01p | LocalThread.java |
| 6,370 | 07-20-01 | 2:33a | LogonData.java |
| 4,388 | 07-19-01 | 9:33a | LogonException.java |
| 9,974 | 07-20-01 | 2:34a | LogonPanel.java |
| 6,951 | 12-20-00 | 5:01p | LogonView.java |
| <DIR> | 05-03-02 | 4:26p | map |
| 4,108 | 12-20-00 | 2:56p | NodeProperties.java |
| 1,452 | 01-10-01 | 12:01p | package.html |
| 527 | 08-08-00 | 9:35a | red-ball.gif |
| 9,701 | 05-01-01 | 2:59p | RegisterRMIServer.java |
| 1,768 | 10-16-01 | 7:38a | Register.properties |
| 6,217 | 12-21-00 | 9:48a | RemoveRMIServer.java |
| 59 | 07-21-00 | 9:36a | rmi.bat |
| 3,595 | 12-20-00 | 5:01p | Subspace.java |
| 8,561 | 02-23-01 | 1:10a | SwingThread.java |
| 4,981 | 12-20-00 | 5:01p | TableMap.java |
| 18,181 | 12-20-00 | 5:01p | TableSorter.java |
| 36,627 | 05-18-01 | 7:57a | ToolsAccess.java |
| 21,114 | 05-31-01 | 4:13a | ToolsMenu.java |

Directory of D:\GGB_1.2.1\com\roche\rde\wip\service\about

| | | | |
|---|---|---|---|
| <DIR> | 05-03-02 | 4:24p | CVS |
| <DIR> | 05-03-02 | 4:24p | doc-files |

Directory of D:\GGB_1.2.1\com\roche\rde\wip\service\about\CVS

| | | | |
|---|---|---|---|
| 3 | 05-03-02 | 4:24p | Entries |
| 19 | 05-03-02 | 4:24p | Entries.Log |
| 64 | 05-03-02 | 4:24p | Repository |
| 53 | 05-03-02 | 4:24p | Root |

Directory of D:\GGB_1.2.1\com\roche\rde\wip\service\about\doc-files

| | | | |
|---|---|---|---|
| <DIR> | 05-03-02 | 4:24p | CVS |

Directory of D:\GGB_1.2.1\com\roche\rde\wip\service\about\doc-files\CVS

| | | | |
|---|---|---|---|
| 3 | 05-03-02 | 4:24p | Entries |
| 74 | 05-03-02 | 4:24p | Repository |
| 53 | 05-03-02 | 4:24p | Root |

Directory of D:\GGB_1.2.1\com\roche\rde\wip\service\console

| | | | |
|---|---|---|---|
| 925 | 09-01-00 | 3:55p | blue-ball.gif |
| 45,728 | 10-17-01 | 8:51a | ConsoleClient.java |
| 298 | 06-26-01 | 6:30a | Console.properties |
| 1,337 | 12-21-00 | 5:37p | ConsoleException.java |
| 29,718 | 04-09-02 | 5:18a | ConsoleGUITest.java |
| <DIR> | 05-03-02 | 4:24p | CVS |
| <DIR> | 05-03-02 | 4:24p | doc-files |
| 7,335 | 01-23-01 | 5:20a | DrawXCanvas.java |
| 22,518 | 12-21-00 | 5:37p | GraphCanvas.java |
| 886 | 09-01-00 | 3:55p | green-ball.gif |
| 3,461 | 12-21-00 | 5:37p | ImageCanvas.java |
| 8,671 | 12-21-00 | 5:37p | LogData.java |
| 7,816 | 12-21-00 | 5:37p | LogPanel.java |
| 2,658 | 04-10-02 | 4:16a | LogPanelTest.java |
| 3,685 | 12-21-00 | 5:37p | LogView.java |
| 6,269 | 01-25-01 | 7:32a | MessagePanel.java |
| 3,008 | 04-10-02 | 4:16a | MessagePanelTest.java |
| 4,544 | 12-21-00 | 5:37p | MessageView.java |
| 2,019 | 01-15-01 | 9:57a | package.html |
| 3,803 | 12-21-00 | 5:37p | PropertyView.java |
| 16,812 | 07-06-01 | 3:17a | PropertyData.java |
| 4,671 | 12-21-00 | 5:37p | PropertyFileNode.java |
| 13,716 | 02-14-01 | 7:54a | PropertyPanel.java |
| 2,736 | 04-10-02 | 5:17a | PropertyPanelTest.java |
| 8,450 | 12-21-00 | 5:37p | RDEMachineComboBoxData.java |
| 527 | 09-01-00 | 3:55p | red-ball.gif |
| 23,708 | 01-24-01 | 5:52a | ServerAccess.java |
| 1,024 | 09-01-00 | 4:24p | StatusData.java |
| 6,876 | 01-23-01 | 5:22a | StatusPanel.java |
| 4,280 | 01-23-01 | 5:23a | StatusPanelTest.java |
| 4,604 | 12-21-00 | 5:37p | StatusView.java |
| 7,197 | 12-21-00 | 5:37p | StudyComboBoxData.java |
| 18,610 | 10-18-01 | 5:36a | StudyData.java |
| 11,754 | 12-21-00 | 5:37p | StudyPanel.java |

TABLE 1-continued

Contents of the Computer Program Listing Appendix

```
     2,797   12-21-00   5:37p    StudyPanelTest.java
     9,612   12-21-00   5:37p    StudyView.java
    27,141   01-17-01  12:27p    topology.jpg
Directory of D:\GGB_1.2.1\com\roche\rde\wip\service\console\CVS
     1,790   05-03-02   4:24p    Entries
        19   05-03-02   4:24p    Entries.Log
        66   05-03-02   4:24p    Repository
        53   05-03-02   4:24p    Root
Directory of D:\GGB_1.2.1\com\roche\rde\wip\service\console\doc-files
   165,386   01-03-01   5:39p    console.jpg
     <DIR>   05-03-02   4:24p    CVS
Directory of D:\GGB_1.2.1\com\roche\rde\wip\service\console\doc-files\CVS
        51   05-03-02   4:24p    Entries
        76   05-03-02   4:24p    Repository
        53   05-03-02   4:24p    Root
Directory of D:\GGB_1.2.1\com\roche\rde\wip\service\CVS
     2,182   05-03-02   4:24p    Entries
        78   05-03-02   4:24p    Entries.Log
        58   05-03-02   4:24p    Repository
        53   05-03-02   4:24p    Root
Directory of D:\GGB_1.2.1\com\roche\rde\wip\service\doc-files
     <DIR>   05-03-02   4:24p    CVS
   657,615   01-03-01   2:35p    service.jpg
Directory of D:\GGB_1.2.1\com\roche\rde\wip\service\doc-files\CVS
        51   05-03-02   4:24p    Entries
        68   05-03-02   4:24p    Repository
        53   05-03-02   4:24p    Root
Directory of D:\GGB_1.2.1\com\roche\rde\wip\service\exec
     1,601   03-23-00   3:03p    AppSvr.java
     <DIR>   05-03-02   4:24p    CVS
     1,214   10-26-00  12:26p    ExecClnt.java
     2,835   04-21-00   1:36p    ExecSvr.java
       240   04-05-00   4:03p    ExecSvr.properties
     7,859   05-03-02   4:26p    ExecSvr_Stub.java
       219   03-23-00   2:57p    IExecSvr.java
    BAT 59   07-21-00   9:36a    rmi.bat
Directory of D:\GGB_1.2.1\com\roche\rde\wip\service\exec\CVS
       281   05-03-02   4:24p    Entries
        63   05-03-02   4:24p    Repository
        53   05-03-02   4:24p    Root
Directory of D:\GGB_1.2.1\com\roche\rde\wip\service\map
       925   04-04-00   1:52p    blue-ball.gif
    12,493   05-04-01   8:09a    ConfigureData.java
    19,720   12-22-00   5:37p    ConfigurePanel.java
     4,366   12-22-00   5:37p    ConfigureView.java
    11,560   12-22-00   5:37p    CRFDataItem.java
    18,709   12-22-00   5:37p    CRFElement.java
    18,653   08-30-01   4:04a    CRFPainter.java
     <DIR>   05-03-02   4:24p    CVS
     <DIR>   05-03-02   4:24p    doc-files
       886   04-04-00   1:52p    green-ball.gif
    14,594   12-22-00   5:37p    IMap.java
    18,835   07-23-01   1:24a    MapActivator.java
    28,315   05-03-02   4:26p    MapActivator_Stub.java
    45,012   10-17-01   8:53a    MapClient.java
   120,096   03-28-02   9:11a    MapServer.java
       703   06-26-01   6:31a    MapServer.properties
    30,701   05-04-01   8:10a    MapServerAccess.java
    26,236   04-10-02   4:16a    MapServerTest.java
    27,643   05-03-02   4:26p    MapServer_Stub.java
       166   06-26-01   6:31a    MapUser.properties
     2,391   01-10-01  12:01p    package.html
     9,422   12-22-00   5:37p    PropertyNode.java
       527   04-04-00   1:52p    red-ball.gif
       103   07-21-00   9:36a    rmi.bat
    18,566   04-03-02   8:54a    StudyChooser.java
    20,268   04-03-02   9:02a    StudyChooserData.java
     8,174   10-17-01   2:17a    StudyChooserView.java
    20,392   05-04-01   8:11a    StudyData.java
    26,012   10-18-01   8:14a    StudyPanel.java
     6,971   12-22-00   5:37p    StudyView.java
Directory of D:\GGB_1.2.1\com\roche\rde\wip\service\map\CVS
     1,317   05-03-02   4:24p    Entries
        19   05-03-02   4:24p    Entries.Log
        62   05-03-02   4:24p    Repository
        53   05-03-02   4:24p    Root
```

TABLE 1-continued

Contents of the Computer Program Listing Appendix

```
Directory of D:\GGB_1.2.1\com\roche\rde\wip\service\map\doc-files
  <DIR>       05-03-02    4:24p    CVS
  152,175     01-03-01    5:44p    map.jpg
Directory of D:\GGB_1.2.1\com\roche\rde\wip\service\map\doc-files\CVS
       47     05-03-02    4:24p    Entries
       72     05-03-02    4:24p    Repository
       53     05-03-02    4:24p    Root
Directory of D:\GGB_1.2.1\com\roche\rde\wip\storage
    4,040     12-28-99    4:19a    ACStorageMgr.java
  <DIR>       05-03-02    4:24p    CVS
  <DIR>       05-03-02    4:24p    doc-files
    3,201     06-07-00    1:35p    EventRange.java
   70,537     10-18-01    9:24a    GgbTableRdr.java
    6,009     01-10-01    12:02p   package.html
   32,884     01-19-01    4:13p    StorageMgr.java
   10,782     08-06-01    1:03a    Storage.properties
   33,273     04-10-02    12:59p   StorageMgrTest.java
Directory of D:\GGB_1.2.1\com\roche\rde\wip\storage\CVS
      358     05-03-02    4:24p    Entries
       19     05-03-02    4:24p    Entries.Log
       58     05-03-02    4:24p    Repository
       53     05-03-02    4:24p    Root
Directory of D:\GGB_1.2.1\com\roche\rde\wip\storage\doc-files
  <DIR>       05-03-02    4:24p    CVS
    5,518     01-10-01    12:10p   storage.gif
Directory of D:\GGB_1.2.1\com\roche\rde\wip\storage\doc-files\CVS
       51     05-03-02    4:24p    Entries
       68     05-03-02    4:24p    Repository
       53     05-03-02    4:24p    Root
Directory of D:\GGB_1.2.1\com\roche\rde\wip\studysite
  <DIR>       05-03-02    4:24p    CVS
   25,822     09-03-00    4:25p    DciQualifier.java
    6,522     04-04-01    7:40a    DciQualReader.java
  <DIR>       05-03-02    4:24p    doc-files
    2,558     02-04-02    1:04p    OcDesignElement.java
    5,378     02-04-02    1:04p    OcInvestigator.java
    9,007     02-08-02    2:55a    OcPatient.java
    7,001     02-04-02    1:04p    OcSite.java
   39,188     02-11-02    4:11a    OCStudySiteTableReader.java
    3,195     01-10-01    12:02p   package.html
   41,435     03-28-02    3:58a    PatientMapper.java
    3,170     11-09-00    8:25p    StudySiteEvent.java
    2,890     05-03-02    4:28a    StudySite.properties
   34,461     02-11-02    4:11a    StudySiteMgr.java
   10,543     04-10-02    12:59p   StudySiteMgrTest.java
    6,184     06-12-00    6:29p    StudySitePacket.java
Directory of D:\GGB_1.2.1\com\roche\rde\wip\studysite\CVS
      740     05-03-02    4:24p    Entries
       19     05-03-02    4:24p    Entries.Log
       60     05-03-02    4:24p    Repository
       53     05-03-02    4:24p    Root
Directory of D:\GGB_1.2.1\com\roche\rde\wip\studysite\doc-files
  <DIR>       05-03-02    4:24p    CVS
   13,129     02-23-01    1:14a    studysite.gif
Directory of D:\GGB_1.2.1\com\roche\rde\wip\studysite\doc-files\CVSE
       53     05-03-02    4:24p    Entries
       70     05-03-02    4:24p    Repository
       53     05-03-02    4:24p    Root
Directory of D:\GGB_1.2.1\com\roche\rde\wip\testdata
    2,110     02-04-02    1:04p    BA15428_TMData_June6.prd
  235,360     10-15-99    9:55a    BA15428.sdd
      893     01-05-00    6:29p    BA15428_OCDpkt.octabin
   28,241     08-18-00    10:11a   BA15428_A1_SITE1_egar.prd
   51,817     11-08-99    3:50p    BA15428_OCCfg_rdesim.properties
        6     12-08-99    6:00p    BA15428_rpl02163_1.psf
  368,327     03-01-00    9:47a    BA15428_Edi20_MapTester.sdd
  401,217     05-24-00    3:39p    BA15428_Map2_TransTester.tab
    1,045     11-08-99    3:50p    BA15428_OCData_rdesim.txt
   24,967     12-12-99    6:26p    BA15428_Edi_rdesim.prd
  404,838     08-07-00    6:58p    BA15428_Edi_MapTester.sdd
  181,986     03-06-00    12:31p   BA15428_Map_20_MapTester.tab
    2,906     05-03-02    6:00a    BA15428_g42site1_unittest.prd
  326,031     05-03-02    4:28a    BA15428_Map_MapTester.tab
   71,918     12-08-99    6:00p    BA15428_rpl02163_19991208165132.prd
   52,495     12-30-99    11:01a   BA15428_OCData.tab
    2,375     09-13-00    3:30p    BA15428_TMDpkt_peerTester.tab
  182,188     08-28-01    3:20a    BA15428_OCMpkt.tab
```

TABLE 1-continued

Contents of the Computer Program Listing Appendix

| | | | |
|---|---|---|---|
| 234,061 | 11-08-99 | 3:50p | BA15428__OCMpkt__rdesim__rdesim.tab |
| 560,869 | 11-24-99 | 4:42p | BA15428__TMMeta__mmpr.tab |
| 1,175 | 05-02-02 | 6:05a | BA15428__OCData__JUNIT.tab |
| 92,627 | 01-25-00 | 3:31p | BA15428__TMDpkt__rdesim.tab |
| 72,612 | 09-13-00 | 3:30p | BA15428__OCData__TransTester.tab |
| 602 | 11-29-99 | 12:11p | BA15428__StdSitepkt.tab |
| 79,261 | 12-22-99 | 4:53p | BA15428__rpl02163__19991222153929.prd |
| 70,111 | 12-22-99 | 4:57p | BA15428__rpl02163__19991222154651.prd |
| 4,131 | 12-05-99 | 9:34a | BASE311C__OCMpkt.tab |
| <DIR> | 05-03-02 | 4:24p | CVS |
| 566 | 05-10-00 | 10:58a | GGB__TEST.jar |
| 3,300 | 03-23-00 | 7:57a | JUnit__log__Storage.tab |
| 453,082 | 03-23-00 | 7:57a | JUnit__Map__Storage.tab |
| 1,586 | 10-19-00 | 10:19a | JUnit__SACpkt__Storage.tab |
| 3,135 | 01-07-00 | 4:24p | log__exec.tab |
| 74,347 | 01-19-00 | 6:15p | M75003__OCMpkt.tab |
| 160,958 | 02-21-00 | 3:42a | M75005__Edi20__MapTester.sdd |
| 204,136 | 06-06-00 | 4:17p | M75005__Map__MapTester.tab |
| 32,943 | 05-03-02 | 4:28a | M75005__Edi__MapTester.sdd |
| 56,203 | 06-06-00 | 4:17p | M75005__OCMpkt.tab |
| 99,224 | 06-06-00 | 4:17p | MF4491__OCMpkt.tab |
| 235,846 | 06-14-00 | 9:50p | MF4499__Edi__MapTester.sdd |
| 226,866 | 06-14-00 | 9:50p | MF4499__Map__MapTester.tab |
| 103,225 | 04-24-00 | 7:09p | MF4499__OCMpkt.tab |
| 286,511 | 08-14-00 | 4:40p | NM16189__TMMpkt__july27__rde01__RdeTester.sdd |
| 97,335 | 07-11-00 | 2:11p | NM16189__963345973587__OCMPKT.tab |
| 42,397 | 07-11-00 | 2:11p | NM16189__963346005172__TMMPKT.tab |
| 4,220 | 07-11-00 | 2:11p | NM16189__963346005192__STUDYMAP.tab |
| 131,189 | 07-21-00 | 11:20a | NM16189__OCMpkt.tab |
| 133,068 | 08-14-00 | 4:13p | NM16189__OCMpkt__update__aug14.tab |
| 2,980 | 11-08-99 | 3:54p | package.html |
| 147,904 | 11-08-99 | 3:50p | PP15981.sdd |
| 55,236 | 11-08-99 | 3:50p | PP15981__Edi__rdesim.prd |
| 11,697 | 11-08-99 | 3:50p | PP15981__TMCfg__rdesim.properties |
| 45,648 | 11-08-99 | 3:50p | PP15981__TMDpkt__rdesim.tab |
| 127,753 | 11-08-99 | 3:50p | PP15981__TMMpkt__rdesim__rdesim.tab |
| 196,691 | 03-08-01 | 5:25a | PV16000__OCMpkt__ApiTester.tab |
| <DIR> | 05-03-02 | 4:24p | regression |
| 670 | 08-22-00 | 11:20a | TESTNM16189__StudyAudit.tab |
| 18,036 | 09-28-00 | 4:49p | TESTNM16189__OCMpkt__Pre__Treatment.tab |
| 19,616 | 08-23-00 | 1:24p | TESTNM16189__OCMpkt__Post__Treatment.tab |
| 17,944 | 07-11-00 | 2:11p | TESTNM16189__963345443124__OCMPKT.tab |
| 50,237 | 07-11-00 | 2:11p | TESTNM16189__963345459137__TMMPKT.tab |
| 4,196 | 07-11-00 | 2:11p | TESTNM16189__963345459267__STUDYMAP.tab |
| 18,045 | 08-10-00 | 8:23p | TESTNM16189__OCMpkt.tab |
| 17 | 05-10-00 | 11:31a | Test.properties |
| 741 | 05-02-02 | 6:05a | TSTRPTFORM__OCDpkt__repeats__e.tab |
| 971 | 05-02-02 | 6:05a | TSTRPTFORM__OCDpkt__repeats__c.tab |
| 741 | 05-02-02 | 6:05a | TSTRPTFORM__OCDpkt__repeats__d.tab |
| 13,584 | 07-23-01 | 8:24a | TSTRPTFORM__2Visits__OCMptk.tab |
| 19,574 | 07-23-01 | 8:24a | TSTRPTFORM__4Visits__OCMptk.tab |
| 1,201 | 05-02-02 | 6:05a | TSTRPTFORM__OCDpkt__repeats__a.tab |
| 980 | 05-02-02 | 6:05a | TSTRPTFORM__OCDpkt__repeats__b.tab |
| 31,834 | 12-05-99 | 9:34a | VALID311C__OCMpkt.tab |

Directory of D:\GGB__1.2.1\com\roche\rde\wip\testdata\CVS

| | | | |
|---|---|---|---|
| 4,187 | 05-03-02 | 4:24p | Entries |
| 20 | 05-03-02 | 4:24p | Entries.Log |
| 59 | 05-03-02 | 4:24p | Repository |
| 53 | 05-03-02 | 4:24p | Root |

Directory of D:\GGB__1.2.1\com\roche\rde\wip\testdata\regression

| | | | |
|---|---|---|---|
| 445,901 | 05-02-02 | 11:36a | BA15428__Edi__RegressionTest__Input.sdd |
| 334,326 | 05-02-02 | 11:36a | BA15428__Map__RegressionTest__Input.tab |
| 1,177 | 05-02-02 | 11:36a | BA15428__OCDPkt__RegressionTest__Input.tab |
| 163,158 | 05-02-02 | 11:36a | BA15428__OCMpkt__RegressionTest__Input.tab |
| 3,870 | 05-02-02 | 11:36a | BA15428__TMDpkt__RegressionTest__Input.tab |
| 359,678 | 05-02-02 | 11:36a | BA15428__TMMPkt__RegressionTest__Input.tab |
| <DIR> | 05-03-02 | 4:24p | CVS |
| 3,203 | 09-13-00 | 2:25p | RSTEST__Map__RegressionTest__Input.tab |
| 3,590 | 09-13-00 | 2:25p | RSTEST__Map__RegressionTest__Input__Updated.tab |
| 4,771 | 09-13-00 | 2:25p | RSTEST__OCMpkt__RegressionTest__Input.tab |
| 4,976 | 09-13-00 | 2:25p | STEST__OCMpkt__RegressionTest__Input__Update.tab |
| 64,038 | 05-02-02 | 11:36a | TESTNM16189__Edi__RegressionTest__Input.sdd |
| 63,412 | 05-02-02 | 11:36a | TESTNM16189__Map__RegressionTest__Input.tab |
| 18,138 | 05-02-02 | 11:36a | TESTNM16189__OCMpkt__RegressionTest__Input.tab |
| 54,775 | 05-02-02 | 11:36a | TESTNM16189__TMMPkt__RegressionTest__Input.tab |

TABLE 1-continued

Contents of the Computer Program Listing Appendix

```
Directory of D:\GGB_1.2.1\com\roche\rde\wip\testdata\regression\CVS
     1,036    05-03-02    4:24p    Entries
        70    05-03-02    4:24p    Repository
        53    05-03-02    4:24p    Root
Directory of D:\GGB_1.2.1\com\roche\rde\wip\tester
    12,851    07-10-00   11:56a    ACWipTestLsnr.java
    19,258    07-10-00   11:56a    ACWipTestMgr.java
    20,487    12-22-99    7:01p    ACWipTestVwr.java
    <DIR>    05-03-02    4:26p    api
    <DIR>    05-03-02    4:26p    auditor
    <DIR>    05-03-02    4:24p    CVS
    <DIR>    05-03-02    4:26p    db
    <DIR>    05-03-02    4:24p    doc-files
    <DIR>    05-03-02    4:26p    map
    <DIR>    05-03-02    4:26p    ocdata
     6,047    02-19-01    2:08a    package.html
    11,311    04-30-02    8:20a    PacketVwr.java
    <DIR>    05-03-02    4:27p    patientaudit
    <DIR>    05-03-02    4:27p    peer
    <DIR>    05-03-02    4:27p    rdesvr
    <DIR>    05-03-02    4:27p    reconcile
    <DIR>    05-03-02    4:26p    regression
    <DIR>    05-03-02    4:26p    rmipeer
    <DIR>    05-03-02    4:26p    storage
    <DIR>    05-03-02    4:26p    studysite
    <DIR>    05-03-02    4:27p    table
     4,979    04-30-02    8:20a    TableMap.java
     8,179    04-30-02    8:20a    TableSorter.java
    <DIR>    05-03-02    4:26p    trans
     9,126    07-23-01    7:14a    WipTestMgr.java
     6,412    12-21-99    5:12p    WipTestVwr.java
     4,029    01-14-00    5:10p    WipTestVwrMetaOCtoTM.java
    15,658    07-23-01    7:20a    WipTestMgrMetaOCtoTM.java
     8,242    01-14-00    5:10p    WipTestVwrDataTMtoOC.java
    20,299    07-23-01    7:51a    WipTestMgrDataTMtoOC.java
     8,778    04-18-00   11:31a    WipTester.java
    14,784    01-17-00    9:44a    WipTestLsnr.java
    28,576    01-17-00    5:42p    WipTestLsnrDataTMtoOC.java
    26,409    01-25-00    5:45p    WipTestLsnrMetaOCtoTM.java
Directory of D:\GGB_1.2.1\com\roche\rde\wip\tester\api
     1,907    02-19-99   12:05a    ApiTester.ini
     4,283    05-18-00    1:00p    ApiTester.java
    41,700    03-28-02    9:11a    ApiTestLsnr.java
    12,520    09-05-00    1:21p    ApiTestVwr.java
    <DIR>    05-03-02    4:24p    CVS
    <DIR>    05-03-02    4:24p    doc-files
       986    02-19-01    7:36a    package.html
Directory of D:\GGB_1.2.1\com\roche\rde\wip\tester\api\CVS
       246    05-03-02    4:24p    Entries
        19    05-03-02    4:24p    Entries.Log
        61    05-03-02    4:24p    Repository
        53    05-03-02    4:24p    Root
Directory of D:\GGB_1.2.1\com\roche\rde\wip\tester\api\doc-files
     5,492    02-19-01    2:13a    ApiTester_State.gif
    <DIR>    05-03-02    4:24p    CVS
Directory of D:\GGB_1.2.1\com\roche\rde\wip\tester\api\doc-files\CVS
        59    05-03-02    4:24p    Entries
        71    05-03-02    4:24p    Repository
        53    05-03-02    4:24p    Root
Directory of D:\GGB_1.2.1\com\roche\rde\wip\tester\auditor
     3,301    07-21-00    2:37p    AuditorTester.java
    20,783    07-23-01    6:59a    AuditorTestLsnr.java
     8,315    09-29-00    9:26a    AuditorTestVwr.java
    <DIR>    05-03-02    4:24p    CVS
Directory of D:\GGB_1.2.1\com\roche\rde\wip\tester\auditor\CVS
       163    05-03-02    4:24p    Entries
        65    05-03-02    4:24p    Repository
        53    05-03-02    4:24p    Root
Directory of D:\GGB_1.2.1\com\roche\rde\wip\tester\CVS
       913    05-03-02    4:24p    Entries
       264    05-03-02    4:24p    Entries.Log
        57    05-03-02    4:24p    Repository
        53    05-03-02    4:24p    Root
Directory of D:\GGB_1.2.1\com\roche\rde\wip\tester\db
    <DIR>    05-03-02    4:24p    CVS
     3,807    05-18-00    1:00p    DbTester.java
    19,150    10-30-00    9:49a    DbTestLsnr.java
```

TABLE 1-continued

Contents of the Computer Program Listing Appendix

| | | | |
|---|---|---|---|
| 6,588 | 09-22-00 | 12:54p | DbTestVwr.java |
| <DIR> | 05-03-02 | 4:24p | doc-files |
| 1,016 | 02-19-01 | 2:13a | package.html |

Directory of D:\GGB_1.2.1\com\roche\rde\wip\tester\db\CVS

| | | | |
|---|---|---|---|
| 196 | 05-03-02 | 4:24p | Entries |
| 19 | 05-03-02 | 4:24p | Entries.Log |
| 60 | 05-03-02 | 4:24p | Repository |
| 53 | 05-03-02 | 4:24p | Root |

Directory of D:\GGB_1.2.1\com\roche\rde\wip\tester\db\doc-files

| | | | |
|---|---|---|---|
| <DIR> | 05-03-02 | 4:24p | CVS |
| 5,197 | 02-19-01 | 2:13a | DbTester_State.gif |

Directory of D:\GGB_1.2.1\com\roche\rde\wip\tester\db\doc-files\CVS

| | | | |
|---|---|---|---|
| 58 | 05-03-02 | 4:24p | Entries |
| 70 | 05-03-02 | 4:24p | Repository |
| 53 | 05-03-02 | 4:24p | Root |

Directory of D:\GGB_1.2.1\com\roche\rde\wip\tester\doc-files

| | | | |
|---|---|---|---|
| <DIR> | 05-03-02 | 4:24p | CVS |
| 4,887 | 02-19-01 | 2:09a | WipTester_State.gif |

Directory of D:\GGB_1.2.1\com\roche\rde\wip\tester\doc-files\CVS

| | | | |
|---|---|---|---|
| 59 | 05-03-02 | 4:24p | Entries |
| 67 | 05-03-02 | 4:24p | Repository |
| 53 | 05-03-02 | 4:24p | Root |

Directory of D:\GGB_1.2.1\com\roche\rde\wip\tester\map

| | | | |
|---|---|---|---|
| 3,072 | 05-08-00 | 8:02p | CRFInspectorVwr.java |
| <DIR> | 05-03-02 | 4:24p | CVS |
| 5,898 | 05-08-00 | 8:02p | DcmLayInspectorVwr.java |
| <DIR> | 05-03-02 | 4:24p | doc-files |
| 4,572 | 02-13-01 | 1:35p | MapTester.java |
| 52,537 | 03-28-02 | 9:11a | MapTestLsnr.java |
| 25,320 | 02-13-01 | 1:35p | MapTestVwr.java |
| 14,098 | 10-11-00 | 1:15p | OCQuestionVwr.java |
| 965 | 02-19-01 | 2:13a | package.html |
| 6,238 | 08-10-00 | 8:07p | TMQuestionVwr.java |

Directory of D:\GGB_1.2.1\com\roche\rde\wip\tester\map\CVS

| | | | |
|---|---|---|---|
| 415 | 05-03-02 | 4:24p | Entries |
| 19 | 05-03-02 | 4:24p | Entries.Log |
| 61 | 05-03-02 | 4:24p | Repository |
| 53 | 05-03-02 | 4:24p | Root |

Directory of D:\GGB_1.2.1\com\roche\rde\wip\tester\map\doc-files

| | | | |
|---|---|---|---|
| <DIR> | 05-03-02 | 4:24p | CVS |
| 7,456 | 02-19-01 | 2:13a | MapTester_State.gif |

Directory of D:\GGB_1.2.1\com\roche\rde\wip\tester\map\doc-files\CVS

| | | | |
|---|---|---|---|
| 59 | 05-03-02 | 4:24p | Entries |
| 71 | 05-03-02 | 4:24p | Repository |
| 53 | 05-03-02 | 4:24p | Root |

Directory of D:\GGB_1.2.1\com\roche\rde\wip\tester\ocdata

| | | | |
|---|---|---|---|
| | 05-03-02 | 4:24p | CVS |
| 3,168 | 05-18-00 | 1:00p | OCDataTester.java |
| 15,284 | 10-04-00 | 3:51p | OCDataTestLsnr.java |
| 6,274 | 10-04-00 | 3:51p | OCDataTestVwr.java |

Directory of D:\GGB_1.2.1\com\roche\rde\wip\tester\ocdata\CVS

| | | | |
|---|---|---|---|
| 160 | 05-03-02 | 4:24p | Entries |
| 64 | 05-03-02 | 4:24p | Repository |
| 53 | 05-03-02 | 4:24p | Root |

Directory of D:\GGB_1.2.1\com\roche\rde\wip\tester\patientaudit

| | | | |
|---|---|---|---|
| <DIR> | 05-03-02 | 4:24p | CVS |
| 3,635 | 12-18-00 | 8:56a | DifferencesFrame.java |
| 1,923 | 12-18-00 | 8:42a | IAuditLabels.java |
| 18,388 | 12-18-00 | 9:26a | PatientAuditVwr.java |
| 7,399 | 12-18-00 | 9:27a | PatientChooser.java |
| 10,167 | 12-18-00 | 8:54a | Patient.java |
| 20,451 | 12-18-00 | 8:45a | PatientAuditLsnr.java |
| 17,647 | 12-18-00 | 9:25a | PatientAuditModel.java |
| 1,212 | 12-18-00 | 8:54a | PatientAuditTester.java |

Directory of D:\GGB_1.2.1\com\roche\rde\wip\tester\patientaudit\CVS

| | | | |
|---|---|---|---|
| 430 | 05-03-02 | 4:24p | Entries |
| 70 | 05-03-02 | 4:24p | Repository |
| 53 | 05-03-02 | 4:24p | Root |

Directory of D:\GGB_1.2.1\com\roche\rde\wip\tester\peer

| | | | |
|---|---|---|---|
| <DIR> | 05-03-02 | 4:24p | CVS |
| 3,336 | 04-10-01 | 6:47a | DataTester.java |
| 21,011 | 07-23-01 | 5:14a | DataTestLsnr.java |
| 11,016 | 04-26-01 | 8:56a | DataTestVwr.java |
| 1,305 | 11-03-99 | 3:07p | package.html |
| 3,373 | 05-18-00 | 1:00p | PeerTester.java |
| 21,225 | 07-23-01 | 7:15a | PeerTestLsnr.java |
| 11,297 | 04-26-01 | 8:56a | PeerTestVwr.java |

TABLE 1-continued

Contents of the Computer Program Listing Appendix

```
Directory of D:\GGB_1.2.1\com\roche\rde\wip\tester\peer\CVS
       351    05-03-02    4:24p    Entries
        62    05-03-02    4:24p    Repository
        53    05-03-02    4:24p    Root
Directory of D:\GGB_1.2.1\com\roche\rde\wip\tester\rdesvr
     <DIR>    05-03-02    4:24p    CVS
     2,821    10-01-00    3:59p    DateConverter.java
    11,871    12-27-00   10:32p    DateConvertLsnr.java
     5,532    10-01-00    5:21p    DateConvertVwr.java
     5,444    02-23-01    8:19a    ImportTimeVwr.java
     1,125    02-19-01    7:36a    package.html
     3,121    04-10-02   11:20a    RdeSvrTest.java
       665    11-08-00    1:25p    RdeSvrTest.properties
     1,268    11-28-00    3:52a    RdeTester.java
    31,090    05-01-01    5:53a    RdeTestLsnr.java
     8,458    10-12-00    7:30p    RdeTestMgr.java
    19,674    04-24-01    8:22a    RdeTestVwr.java
Directory of D:\GGB_1.2.1\com\roche\rde\wip\tester\rdesvr\CVS
       562    05-03-02    4:24p    Entries
        64    05-03-02    4:24p    Repository
        53    05-03-02    4:24p    Root
Directory of D:\GGB_1.2.1\com\roche\rde\wip\tester\reconcile
     <DIR>    05-03-02    4:24p    CVS
     1,206    07-25-01   10:15a    Logger.java
     4,786    07-24-01    5:55a    OCDataReader.java
     4,441    07-26-01   10:21a    Reconcile.java
     9,597    07-25-01   10:12a    TmDataReader.java
Directory of D:\GGB_1.2.1\com\roche\rde\wip\tester\reconcile\CVS
       198    05-03-02    4:24p    Entries
        67    05-03-02    4:24p    Repository
        53    05-03-02    4:24p    Root
Directory of D:\GGB_1.2.1\com\roche\rde\wip\tester\regression
     <DIR>    05-03-02    4:24p    CVS
    22,479    04-10-02   11:20a    RegressionTest.java
Directory of D:\GGB_1.2.1\com\roche\rde\wip\tester\regression\CVS
        56    05-03-02    4:24p    Entries
        68    05-03-02    4:24p    Repository
        53    05-03-02    4:24p    Root
Directory of D:\GGB_1.2.1\com\roche\rde\wip\tester\rmipeer
     <DIR>    05-03-02    4:24p    CVS
       250    04-13-00   11:01a    ITestSvr.java
       834    04-20-00   10:37a    package.html
        59    07-21-00    9:36a    rmi.bat
     3,514    07-21-00    2:37p    RmiPeerTester.java
    16,711    05-18-01    3:07a    RmiPeerTestLsnr.java
     8,873    04-13-00   11:01a    RmiPeerTestVwr.java
     4,342    10-16-01   10:13a    TestClnt.java
     3,801    10-16-01   10:13a    TestSvr.java
     7,871    05-03-02    4:26p    TestSvr_Stub.java
     4,143    04-13-00   11:01a    TextIOStream.java
Directory of D:\GGB_1.2.1\com\roche\rde\wip\tester\rmipeer\CVS
       440    05-03-02    4:24p    Entries
        65    05-03-02    4:24p    Repository
        53    05-03-02    4:24p    Root
Directory of D:\GGB_1.2.1\com\roche\rde\wip\tester\storage
     <DIR>    05-03-02    4:24p    CVS
     <DIR>    05-03-02    4:24p    doc-files
     2,914    01-09-00    7:16p    ObjectVwr.java
       995    02-19-01    2:13a    package.html
     2,941    05-18-00    1:00p    StorageTester.java
    37,813    04-30-02    8:21a    StorageTestLsnr.java
    10,909    04-30-02    8:21a    StorageTestVwr.java
Directory of D:\GGB_1.2.1\com\roche\rde\wip\tester\storage\CVS
       258    05-03-02    4:24p    Entries
        19    05-03-02    4:24p    Entries.Log
        65    05-03-02    4:24p    Repository
        53    05-03-02    4:24p    Root
Directory of D:\GGB_1.2.1\com\roche\rde\wip\tester\storage\doc-files
     <DIR>    05-03-02    4:24p    CVS
     4,959    02-19-01    2:13a    StorageTester_State.gif
Directory of D:\GGB_1.2.1\com\roche\rde\wip\tester\storage\doc-files\CVS
        63    05-03-02    4:24p    Entries
        75    05-03-02    4:24p    Repository
        53    05-03-02    4:24p    Root
```

TABLE 1-continued

Contents of the Computer Program Listing Appendix

```
Directory of D:\GGB_1.2.1\com\roche\rde\wip\tester\studysite
<DIR>        05-03-02    4:24p    CVS
<DIR>        05-03-02    4:24p    doc-files
     1,016   02-19-01    2:13a    package.html
     4,096   05-18-00    1:23p    StdSiteTester.java
    27,554   02-02-00   10:16a    StdSiteTestLsnr.java
    10,721   12-20-99    7:00p    StdSiteTestVwr.java
     3,020   05-18-00    1:23p    StudySiteTester.java
    25,776   02-04-02   11:41a    StudySiteTestLsnr.java
    11,656   04-04-01    7:40a    StudySiteTestVwr.java
Directory of D:\GGB_1.2.1\com\roche\rde\wip\tester\studysite\CVS
       375   05-03-02    4:24p    Entries
        19   05-03-02    4:24p    Entries.Log
        67   05-03-02    4:24p    Repository
        53   05-03-02    4:24p    Root
Directory of D:\GGB_1.2.1\com\roche\rde\wip\tester\studysite\doc-files
<DIR>        05-03-02    4:24p    CVS
     4,295   02-19-01    2:13a    StudySiteTester_State.gif
Directory of D:\GGB_1.2.1\com\roche\rde\wip\tester\studysite\doc-files\CVS
        65   05-03-02    4:24p    Entries
        77   05-03-02    4:24p    Repository
        53   05-03-02    4:24p    Root
Directory of D:\GGB_1.2.1\com\roche\rde\wip\tester\table
<DIR>        05-03-02    4:24p    CVS
     1,711   05-22-00    2:45p    FieldDifference.java
     3,727   05-22-00    2:45p    TableComparison.java
     1,392   05-14-00    6:46p    TableTester.java
    10,369   05-11-00    5:41p    TableTestLsnr.java
    10,255   05-22-00    2:45p    TableTestVwr.java
Directory of D:\GGB_1.2.1\com\roche\rde\wip\tester\table\CVS
       264   05-03-02    4:24p    Entries
        63   05-03-02    4:24p    Repository
        53   05-03-02    4:24p    Root
Directory of D:\GGB_1.2.1\com\roche\rde\wip\tester\trans
<DIR>        05-03-02    4:24p    CVS
<DIR>        05-03-02    4:24p    doc-files
     3,129   12-13-99    6:45p    OCResponseVwr.java
       982   02-19-01    2:13a    package.html
     3,128   12-13-99    6:45p    TMResponseVwr.java
     4,212   07-06-01    9:39a    TransTester.java
    24,816   07-06-01    9:39a    TransTestLsnr.java
    10,303   01-25-00    3:24p    TransTestVwr.java
Directory of D:\GGB_1.2.1\com\roche\rde\wip\tester\trans\CVS
       308   05-03-02    4:24p    Entries
        19   05-03-02    4:24p    Entries.Log
        63   05-03-02    4:24p    Repository
        53   05-03-02    4:24p    Root
Directory of D:\GGB_1.2.1\com\roche\rde\wip\tester\trans\doc-files
<DIR>        05-03-02    4:24p    CVS
     3,958   02-19-01    2:13a    TransTester_State.gif
Directory of D:\GGB_1.2.1\com\roche\rde\wip\tester\trans\doc-files\CVS
        61   05-03-02    4:24p    Entries
        73   05-03-02    4:24p    Repository
        53   05-03-02    4:24p    Root
Directory of D:\GGB_1.2.1\com\roche\rde\wip\tmdata
<DIR>        05-03-02    4:24p    CVS
<DIR>        05-03-02    4:24p    doc-files
       760   10-13-00   12:23p    NullTimeStampException.java
     1,074   01-10-01   12:02p    package.html
    21,438   04-02-02   10:13a    PRDataReader.java
    11,407   04-02-02   10:12a    TMDataMgr.java
    20,383   04-30-02   12:18p    TMData.properties
     9,644   04-10-02    1:22p    TMDataMgrTest.java
    25,027   10-17-01    2:42a    TMDataPacket.java
Directory of D:\GGB_1.2.1\com\roche\rde\wip\tmdata\CVS
       367   05-03-02    4:24p    Entries
        19   05-03-02    4:24p    Entries.Log
        57   05-03-02    4:24p    Repository
        53   05-03-02    4:24p    Root
Directory of D:\GGB_1.2.1\com\roche\rde\wip\tmdata\doc-files
<DIR>        05-03-02    4:24p    CVS
     4,955   01-10-01   12:08p    tmdata.gif
Directory of D:\GGB_1.2.1\com\roche\rde\wip\tmdata\doc-files\CVS
        50   05-03-02    4:24p    Entries
        67   05-03-02    4:24p    Repository
        53   05-03-02    4:24p    Root
```

TABLE 1-continued

Contents of the Computer Program Listing Appendix

```
Directory of D:\GGB_1.2.1\com\roche\rde\wip\tmmeta
   <DIR>      05-03-02    4:24p    CVS
   <DIR>      05-03-02    4:24p    doc-files
    1,051     01-10-01   12:02p    package.html
   15,574     09-12-00   12:34p    TMMetaMgr.java
   36,524     04-30-02   10:28a    TMMeta.properties
   11,177     04-10-02    1:22p    TMMetaMgrTest.java
   13,567     09-12-00   12:55p    TMMetaPacket.java
   21,542     12-27-00   10:32p    TMTableReader.java
Directory of D:\GGB_1.2.1\com\roche\rde\wip\tmmeta\CVS
      308     05-03-02    4:24p    Entries
       19     05-03-02    4:24p    Entries.Log
       57     05-03-02    4:24p    Repository
       53     05-03-02    4:24p    Root
Directory of D:\GGB_1.2.1\com\roche\rde\wip\tmmeta\doc-files
   <DIR>      05-03-02    4:24p    CVS
    3,979     01-10-01   12:07p    tmmeta.gif
Directory of D:\GGB_1.2.1\com\roche\rde\wip\tmmeta\doc-files\CVS
       50     05-03-02    4:24p    Entries
       67     05-03-02    4:24p    Repository
       53     05-03-02    4:24p    Root
Directory of D:\GGB_1.2.1\com\roche\rde\wip\translator
    1,112     12-12-99    6:26p    BasicFcn.java
    3,292     12-13-99    9:22a    CannotComputeException.java
    2,605     12-13-99    9:22a    ConcatFcn.java
    3,886     03-22-00    2:44p    ConstantFcn.java
   <DIR>      05-03-02    4:24p    CVS
   <DIR>      05-03-02    4:24p    doc-files
   15,145     09-15-00    7:51p    FcnInterpreter.java
   12,815     12-27-00   10:32p    FormatDateFcn.java
    3,046     12-12-99    6:26p    FormatFcn.java
    1,214     12-12-99    6:26p    IFcn.java
    5,802     09-08-00   12:11p    MapFcn.java
    1,562     01-10-01   12:03p    package.html
    2,136     02-04-00   12:16p    ResponseFcn.java
    2,990     12-12-99    6:26p    RowValueFcn.java
    4,151     09-19-00    4:15p    TmOcAssignments.java
   55,462     05-01-02   12:21p    TmOcTranslator.java
    3,579     12-12-99    6:26p    TokenizeFcn.java
    2,283     04-10-00   11:44a    ToUpperFcn.java
    1,956     11-09-00    8:25p    TranslateEvent.java
    3,055     02-28-00    3:19p    TranslatorException.java
   10,347     12-20-00    4:20p    TranslatorMgr.java
    6,734     04-10-02    1:22p    TranslatorMgrTest.java
      706     07-19-01   12:45a    Trans.properties
Directory of D:\GGB_1.2.1\com\roche\rde\wip\translator\CVS
    1,078     05-03-02    4:24p    Entries
       19     05-03-02    4:24p    Entries.Log
       61     05-03-02    4:24p    Repository
       53     05-03-02    4:24p    Root
Directory of D:\GGB_1.2.1\com\roche\rde\wip\translator\doc-files
   <DIR>      05-03-02    4:24p    CVS
   22,982     02-23-01    1:14a    translator.gif
Directory of D:\GGB_1.2.1\com\roche\rde\wip\translator\doc-files\CVS
       54     05-03-02    4:24p    Entries
       71     05-03-02    4:24p    Repository
       53     05-03-02    4:24p    Root
Directory of D:\GGB_1.2.1\com\roche\rde\wip\util
    7,503     10-09-00   11:57a    AccessSQLMaker.java
    9,288     04-02-02   10:11a    ACDbPropertyReader.java
    2,518     11-09-00    8:25p    ACEvent.java
   16,340     04-17-00    5:44p    ACGuiListener.java
    9,070     09-20-99   12:29p    ACListener.java
    4,060     04-18-00   11:31a    ACMgr.java
    2,342     02-26-01    1:31p    ACSQLMaker.java
    2,419     07-23-01   10:16a    ACTestCase.java
    3,262     11-23-99   11:32p    ACTesterLsnr.java
   <DIR>      05-03-02    4:24p    client
    8,697     04-05-02    5:13a    Cli.java
   <DIR>      05-03-02    4:25p    control
   <DIR>      05-03-02    4:24p    CVS
    3,613     03-20-00    5:34p    DatabaseException.java
      824     08-30-00   12:42p    DatabaseLockException.java
   28,431     12-27-00   10:32p    DateParser.java
    3,154     08-12-99    9:42a    DateParserAux.java
   56,771     07-02-01    9:14a    DateUtil.java
   21,056     04-09-02    5:18a    DateUtilTest.java
```

TABLE 1-continued

Contents of the Computer Program Listing Appendix

| | | | |
|---|---|---|---|
| 4,529 | 04-10-01 | 7:05a | DBComparison.java |
| 2,637 | 11-09-00 | 6:09a | DBComparisonAccess.java |
| 3,154 | 04-10-01 | 7:05a | DBComparisonOracle.java |
| 3,490 | 02-19-99 | 12:07a | DBMetaDataLayout.java |
| 94,633 | 04-02-02 | 11:39a | DBUtil.java |
| 3,470 | 10-26-00 | 5:39p | DBUtilException.java |
| <DIR> | 05-03-02 | 4:24p | doc-files |
| 2,890 | 09-20-99 | 12:29p | ILsnr.java |
| 1,829 | 02-15-99 | 3:43a | IMgr.java |
| 19,698 | 08-12-99 | 9:42a | IniFile.java |
| 898 | 02-15-99 | 3:43a | IObservable.java |
| 822 | 02-15-99 | 3:43a | IObserver.java |
| 1,226 | 02-15-99 | 3:43a | IStatusReporter.java |
| 1,825 | 02-15-99 | 3:43a | IVwr.java |
| 3,021 | 09-20-99 | 12:29p | JNIException.java |
| 4,151 | 05-31-00 | 3:18p | LabelUtil.java |
| <DIR> | 05-03-02 | 4:24p | ldap |
| 3,433 | 09-20-00 | 10:26a | LoginPrompt.java |
| 2,400 | 12-06-99 | 6:22p | ObservableComponent.java |
| 6,584 | 09-20-00 | 5:13a | OracleSQLMaker.java |
| 508 | 01-10-01 | 12:03p | package.html |
| 3,567 | 02-28-00 | 3:19p | PackageException.java |
| 16,354 | 07-06-01 | 5:17a | Profiler.java |
| 3,847 | 04-22-02 | 12:08p | Profiler.properties |
| 7,166 | 05-02-01 | 1:36a | PropertiesLoader.java |
| 3,852 | 02-07-02 | 4:11p | RankUtil.java |
| 5,707 | 08-20-99 | 3:57p | SimpleFilenameFilter.java |
| 965 | 07-02-01 | 2:29a | SortUtil.java |
| 33,601 | 04-22-02 | 11:09a | StringUtil.java |
| 3,964 | 08-20-99 | 3:57p | Timer.java |

Directory of D:\GGB_1.2.1\com\roche\rde\wip\util\client

| | | | |
|---|---|---|---|
| <DIR> | 05-03-02 | 4:24p | about |
| <DIR> | 05-03-02 | 4:24p | CVS |
| <DIR> | 05-03-02 | 4:24p | logon |

Directory of D:\GGB_1.2.1\com\roche\rde\wip\util\client\about

| | | | |
|---|---|---|---|
| <DIR> | 05-03-02 | 4:24p | CVS |

Directory of D:\GGB_1.2.1\com\roche\rde\wip\util\client\about\CVS

| | | | |
|---|---|---|---|
| 3 | 05-03-02 | 4:24p | Entries |
| 68 | 05-03-02 | 4:24p | Repository |
| 53 | 05-03-02 | 4:24p | Root |

Directory of D:\GGB_1.2.1\com\roche\rde\wip\util\client\CVS

| | | | |
|---|---|---|---|
| 3 | 05-03-02 | 4:24p | Entries |
| 30 | 05-03-02 | 4:24p | Entries.Log |
| 62 | 05-03-02 | 4:24p | Repository |
| 53 | 05-03-02 | 4:24p | Root |

Directory of D:\GGB_1.2.1\com\roche\rde\wip\util\client\logon

| | | | |
|---|---|---|---|
| <DIR> | 05-03-02 | 4:24p | CVS |

Directory of D:\GGB_1.2.1\com\roche\rde\wip\util\client\logon\CVS

| | | | |
|---|---|---|---|
| 3 | 05-03-02 | 4:24p | Entries |
| 68 | 05-03-02 | 4:24p | Repository |
| 53 | 05-03-02 | 4:24p | Root |

Directory of D:\GGB_1.2.1\com\roche\rde\wip\util\control

| | | | |
|---|---|---|---|
| <DIR> | 05-03-02 | 4:24p | CVS |
| <DIR> | 05-03-02 | 4:24p | doc-files |
| 416 | 01-10-01 | 12:04p | package.html |
| 18,396 | 09-20-99 | 12:30p | StateModel.java |
| 1,874 | 09-20-99 | 12:30p | StateTransitionException.java |
| 7,542 | 08-12-99 | 9:42a | State.java |
| 5,538 | 09-20-99 | 12:30p | Transition.java |

Directory of D:\GGB_1.2.1\com\roche\rde\wip\util\control\CVS

| | | | |
|---|---|---|---|
| 254 | 05-03-02 | 4:24p | Entries |
| 19 | 05-03-02 | 4:24p | Entries.Log |
| 63 | 05-03-02 | 4:24p | Repository |
| 53 | 05-03-02 | 4:24p | Root |

Directory of D:\GGB_1.2.1\com\roche\rde\wip\util\control\doc-files

| | | | |
|---|---|---|---|
| 5,391 | 01-10-01 | 12:06p | control.gif |
| <DIR> | 05-03-02 | 4:24p | CVS |

Directory of D:\GGB_1.2.1\com\roche\rde\wip\util\control\doc-files\CVS

| | | | |
|---|---|---|---|
| 51 | 05-03-02 | 4:24p | Entries |
| 73 | 05-03-02 | 4:24p | Repository |
| 53 | 05-03-02 | 4:24p | Root |

Directory of D:\GGB_1.2.1\com\roche\rde\wip\util\CVS

| | | | |
|---|---|---|---|
| 2,232 | 05-03-02 | 4:24p | Entries |
| 66 | 05-03-02 | 4:24p | Entries.Log |
| 55 | 05-03-02 | 4:24p | Repository |
| 53 | 05-03-02 | 4:24p | Root |

TABLE 1-continued

Contents of the Computer Program Listing Appendix

```
Directory of D:\GGB_1.2.1\com\roche\rde\wip\util\doc-files
<DIR>       05-03-02    4:24p   CVS
   50,282   01-10-01   12:05p   util.gif
Directory of D:\GGB_1.2.1\com\roche\rde\wip\util\doc-files\CVS
       48   05-03-02    4:24p   Entries
       65   05-03-02    4:24p   Repository
       53   05-03-02    4:24p   Root
Directory of D:\GGB_1.2.1\com\roche\rde\wip\util\ldap
<DIR>       05-03-02    4:24p   CVS
Directory of D:\GGB_1.2.1\com\roche\rde\wip\util\ldap\CVS
        3   05-03-02    4:24p   Entries
       60   05-03-02    4:24p   Repository
       53   05-03-02    4:24p   Root
Directory of D:\GGB_1.2.1\com\roche\rde\wip\xml
<DIR>       05-03-02    4:24p   CVS
Directory of D:\GGB_1.2.1\com\roche\rde\wip\xml\CVS
        3   05-03-02    4:24p   Entries
       54   05-03-02    4:24p   Repository
       53   05-03-02    4:24p   Root
Directory of D:\GGB_1.2.1\data
<DIR>       05-03-02    4:23p   CVS
Directory of D:\GGB_1.2.1\data\CVS
        3   05-03-02    4:23p   Entries
       45   05-03-02    4:23p   Repository
       53   05-03-02    4:23p   Root
Directory of D:\GGB_1.2.1\lib
   45,386   05-03-02    4:23p   activation.jar
1,564,620   05-03-02    4:23p   classes12_01.zip
<DIR>       05-03-02    4:23p   CVS
<DIR>       05-03-02    4:24p   ggb
    2,881   05-03-02    4:23p   ggb_server_policy
  167,941   05-03-02    4:23p   ldapjdk.jar
  225,932   05-03-02    4:23p   mail.jar
<DIR>       05-03-02    4:23p   oc
  152,795   05-03-02    4:23p   test.jar
Directory of D:\GGB_1.2.1\lib\CVS
      330   05-03-02    4:23p   Entries
       44   05-03-02    4:23p   Repository
       53   05-03-02    4:23p   Root
Directory of D:\GGB_1.2.1\lib\ggb
  171,520   05-03-02    4:23p   .#wip_dcapi.dll.1.4
<DIR>       05-03-02    4:23p   CVS
  271,360   05-03-02    4:24p   dcapi.dll
   21,297   05-03-02    4:23p   dcapi.h
  130,048   05-03-02    4:23p   hello.dll
  175,616   05-03-02    4:24p   wip_dcapi.dll
Directory of D:\GGB_1.2.1\lib\ggb\CVS
      198   05-03-02    4:23p   Entries
       48   05-03-02    4:23p   Repository
       53   05-03-02    4:23p   Root
Directory of D:\GGB_1.2.1\lib\oc
<DIR>       05-03-02    4:23p   CVS
Directory of D:\GGB_1.2.1\lib\oc\CVS
        3   05-03-02    4:23p   Entries
       47   05-03-02    4:23p   Repository
       53   05-03-02    4:23p   Root
Total files listed:

1,494 file(s)         32,318,461 bytes
   579 dir(s)
```

The Computer Program Listing Appendix disclosed in Table 1 is hereby incorporated by reference.

3. FIELD OF THE INVENTION

This invention relates generally to a software program and method that converts a back-end clinical definition, defining a data structure and legacy data entry forms for data entry into a clinical data management system, to a front-end study definition.

4. BACKGROUND OF THE INVENTION

Before a new drug may be sold in many countries of the world, regulatory approval must be granted. One of the most expensive and difficult aspects of obtaining this regulatory approval is the presentation of statistically significant data from clinical trials. Typically, clinical trials used to support a new drug application are divided into three or more phases, the most prominent of which are phases I, II, and III.

Phase I studies are primarily concerned with assessing the safety of a drug. Phase I testing in humans is typically done in about 20 to 100 healthy volunteers. A phase I clinical study is designed to determine what happens to the drug in the patient. That is, how it is absorbed, metabolized, and excreted. In addition, by measuring the side effects of the drug at various dosage levels, a phase I study provides information on optimal drug dosage.

While a phase I study is directed to drug safety, a phase II clinical trial is directed to drug efficacy. A phase II study occurs after successful completion of a phase I study. A phase II clinical study may last from several months to two years, and involve up to several hundred patients at numerous clinical sites throughout the world. Most phase II studies are randomized trials. One group of patients receives the experimental drug while a control group receives a placebo. Often phase II studies are "blinded" in the sense that neither the patients nor the researchers know who is getting the experimental drug. In this manner, the phase II study can provide a pharmaceutical company and a regulatory body, such as the United States Food and Drug Administration (FDA) of the United States or the European Commission (EC) of the European Union, comparative information about the efficacy of the new drug. If the phase II study is successful, a phase III study may be authorized.

Typically, in a phase III study, the new drug is tested in several hundred to several thousand patients at hundreds of clinical sites throughout the world. This large-scale testing provides the pharmaceutical company and the regulatory agency with a more thorough understanding of the drug's effectiveness, benefits, and the range of possible adverse reactions. Most phase III studies are randomized and blinded trials. Phase III studies typically last several years. Once a phase III study is successfully completed, a pharmaceutical company can request regulatory approval for marketing the new drug.

The resources needed to support a complex multi-site phase II or phase III clinical are staggering. Trained professionals must administer the new drug under the exact requirements of the protocols of the clinical study and intricate patient records must be maintained. The clinical trial protocol may require numerous patient visits over an extended period of time. Any error in the patient record could result in patient data disqualification.

Because of the complexity of the protocols used in clinical trials, the amount of information that must be tracked requires the capabilities of a back-end clinical data management system (CDMS). Representative back-end clinical data management systems include Clintrial 4.3, (Clinsoft Corporation, Lexington, Mass., www.clinsoft.net), and Oracle Clinical (O/C), Oracle Inc., Redwood Shores, Calif., www.oracle.com). These back-end clinical data management systems typically provide sophisticated tools such as, a batch validation engine, a batch data loader, a randomization system, a thesaurus management system, and a lab reference range system. However, because a clinical trial may be conducted at hundreds of sites throughout the world, it is impracticable to place a back-end CDMS at each clinical site. The problem of routing clinical data into a back-end CDMS: has therefore been addressed by a number of different approaches in the art.

A traditional approach to routing clinical data to a back-end CDMS is to gather clinical data at each site using paper-based forms designed in accordance with the specifications of a clinical trial. At a later date, the paper-based forms are manually entered twice into a computer. This double-entry is requested in order to compare the two data sets in order to check for data entry errors. While this approach is functional, it is unsatisfactory. Electronic data entry based on the paper-based forms is often done at a site that is remote from the clinical setting, making it difficult to consult the clinician if there is a problem with the content of the paper-based forms. Because of the exact requirements of the clinical trial protocol, such unresolved errors typically result in patient disqualification. Another problem with paper-based forms is that the information is essentially processed twice, first, when the data is entered on the paper-based form and, second, when the electronic data entry is done based on the content of the paper-base forms. This effectively doubles the chance of error in the data entry process. Yet another problem with paper based forms is that there is considerable delay before the clinical data is available is review because a sponsor needs to wait until the clinical data is entered into the back-end database before electronic analysis may be run on the clinical data.

To address the problems with traditional approaches to clinical data entry into a legacy CDMS, an entire industry of Remote Data Entry (RDE) products has developed. Representative vendors in this industry include InferMed, Ltd., London UK, (www.infermed.com), Phase Forward Inc., Waltham, Mass., (www.phaseforward.com), CB Technology, Philadelphia, Pa., (www.cbtech.com), DataTRAK Cleveland, Ohio, (www.datatraknet.com), and Araccel, Stockholm, Sweden, (www.araccel.com), and TEAMworks, Hannover, Germany (www.teamworks.de). These RDE products are also termed front-end data acquisition products. RDE products provide capabilities for making electronic clinical data entry forms that are used on a client computer, such as a laptop, at the clinical site. Data collected using an RDE product are sent electronically to a centralized back-end CDMS where statistical analysis is performed on the clinical data to ascertain drug efficacy and/or safety.

RDE products are advantageous because they prevent discrepancies during data entry. An RDE product provides electronic case report forms (eCRFs) to the data entrant for entry of clinical data. The eCRF is capable of containing data validation checks that show a warning in the case when incorrect or "out of the programmed range" entries are received. The data entrant can then correct the problem with the data entry immediately. In addition the eCRF provides "protocol guidance." For example, pregnancy test questions are only displayed to the data entrant when the patient has indicated that she is female.

While RDE products represent an advance over the paper-based form approach, they are unsatisfactory. RDE products require a custom study definition to be prepared for each clinical trial. For example, MACRO from InferMed, Ltd., London UK, requires that a macro study definition be prepared for each clinical trial monitored by MACRO. The macro study definition is a collection of metatables that describe the patient data collected at a clinical site. The macro study definition may also include the format of the electronic forms used to acquire the clinical data as well as other pertinent data acquisition components.

In the art, a clinical definition must be set up for the back-end CDMS. The back-end clinical definition is a data structure that is used to track all the patients in a clinical study. The back-end clinical definition is designed in accordance with the specifications of the particular back-end CDMS used to support a particular clinical study. The problem with the RDE custom study definitions and the back-end clinical definitions becomes apparent when one tries to interface the RDE custom study definition to the back-end clinical definition. Because there are no industry standards for RDE study definitions and back-end clinical definitions, significant custom programming is needed for each clinical study, in order to allow an RDE system to electronically feed data to a back-end CDMS.

A third approach to addressing the problem of clinical data entry is to provide a web page interface to a back-end CDMS. An example of a product that uses this approach is Oracle Clinical Remote Data Capture v4i, Oracle Inc., Redwood Shores, Calif. In this approach, each clinical site includes a client computer with a standard web browser. The web browser is used to load into the client computer a data entry form from a remote web server. Clinical data are then entered into the data entry form. Advantageously, the data entered into the web-based data entry form may be electronically entered directly into the back-end CDMS. While the third approach eliminates the need to interface a front-end study definition with a back-end clinical definition, this approach is still unsatisfactory. First, the client computer must be connected to the back-end CDMS by a long-distance network throughout data entry. This requirement limits how the web page interface may be constructed and deployed. Another disadvantage to using a long-distance network throughout data entry are the issues of network latency, network bandwidth limitations, and server load that are inevitably raised. These issues conspire to make data entry a frustrating experience. In fact, it is widely appreciated that data entry using a web page driven by a remote server requires tremendous patience. For example, consider the amount of patience required to enter personal data at an Internet web site, such as www.amazon.com, in order to register at the site. Clinical data entry using a web page system, such as Oracle Clinical Remote Data Capture v4i, is comparable to registering hundreds to thousands of people at a site such as www.amazaon.com or www.gap.com on a periodic basis over an extended period of time.

Yet another disadvantage of using a web page interface to a back-end CDMS is that back-end CDMS interfaces are designed for data-entry clerks. Therefore, they lack support for the tools necessary to ensure that clinical trial protocol is followed. Such tools include protocol violation alerts, enforced eligibility, and protocol recommendations regarding dosing or test procedures. Furthermore, direct data entry into a back-end CDMS using a web-page introduces questionable practices. Back-end CDMS interfaces are designed to facilitate data entry by data-entry clerks. As such, many of the fields in the data entry forms have defaulted answers. While the use of defaulted answers is appropriate for routine data-entry, it is not appropriate for forms that are considered source documents. A source document represents the form that records actual clinical observations. In order to ensure that all clinical observations mandated by a clinical protocol are actually made, the source form should not have defaulted answers.

In view of these difficulties, what is needed in the art is a system and method for collecting clinical data without the many drawbacks found in preexisting systems and methods.

Discussion or citation of a reference herein will not be construed as an admission that such reference is prior art to the present invention.

5. SUMMARY OF THE INVENTION

The present invention provides novel solutions to the drawbacks found in the art. In particular, the present invention uses a back-end clinical definition developed in accordance with a legacy back-end CDMS to generate a set of forms, also termed a front-end study definition, that can be used by a front-end Remote Data Entry (RDE) product. A clinical worker designs a back-end clinical definition using a back-end CDMS. Then, using the instant invention, the back-end clinical definition is converted into a front-end study definition. The front-end study definition is transferred to each computer hosting a front-end data RDE product in a clinical trial. The front-end RDE product uses the front-end study definition to regulate the acquisition of clinical data. The front-end study definition includes the description of a set of forms that are used by a data entrant to enter clinical data.

During the process of converting a back-end clinical definition to a front-end study definition, a novel conversion map is created. The conversion map allows for the conversion of clinical data acquired with the RDE product to a format that can be electronically read by a back-end CDMS. In one embodiment of the present invention, clinical data acquired using the front-end RDE product is converted into a novel front-end data packet that can be electronically imported into the legacy back-end CDMS. In this way, data can be acquired without independently creating a back-end clinical definition and a front-end study definition and tediously resolving conflicts between the two definitions. Furthermore, the instant invention allows front-end data to be acquired in real-time without the use of time consuming Internet driven menus that attempt to pipe data directly into a back-end CDMS over the Internet using web page-based data entry screens.

One aspect of the present invention provides a method for defining a front-end study definition based on a back-end clinical definition. In the method, a conversion map is created for matching a set of first components in the back-end clinical definition with a set of second components in the front-end study definition. Each of the first components in the set of first components in the back-end clinical definition is parsed. This parsing step involves: (i) adding an identifier to the conversion map that corresponds to the first component, (ii) editing the front-end study definition to include a second component that corresponds to the first component and, (iii) revising the conversion map to include the identity of the second component in the front-end study definition that corresponds with the first component. When the parsing step is completed, the conversion map includes a record of matching first and second components in the back-end clinical definition and the corresponding front-end study definition. In one embodiment of the present invention the back-end study definition is an Oracle Clinical definition and the front-end study definition is a macro study definition.

Another aspect of the present invention provides a computer readable memory that is used to direct a client/server system to function in a specified manner. The computer readable memory includes a back-end CDMS that is capable of saving data in accordance with a back-end clinical definition. The memory further includes a Remote Data Entry module for collecting clinical data in accordance with a front-end study definition. The memory also includes a mapper server module for converting the back-end clinical definition into a corresponding front-end study definition. The study definition module includes executable instructions stored in the computer readable memory, including instructions for creating a conversion map that matches a set of first components in the back-end clinical definition with a set of second components in the corresponding front-end study definition. Further the study definition module includes instructions for parsing each of the first components in the set of first components in the back-end clinical definition. For each of these first components in the set of first components, the instructions for parsing include (i) instructions for adding an identifier to the conversion map that corresponds to the first component, (ii) instructions for editing the corresponding front-end study definition to include a second component that corresponds to the first component, and (iii) instructions for revising the conversion map to include the identity of the second component in the front-end study definition that corresponds with the first component. When the instructions for parsing are completed, the conversion map includes a record of matching first and second components in the back-end clinical definition and the corresponding front-end study definition.

Yet another aspect of the present invention provides a method for storing clinical data in a back-end CDMS in accordance with a back-end clinical definition. In this method, a front-end data packet is obtained from a Remote Data Entry module. The Remote Data Entry module collects the clinical data in accordance with a front-end study definition. Then the front-end data packet is parsed. For each patient in the front-end data packet, this parsing step comprises adding front-end study definition/back-end clinical definition match data for the patient to a conversion map. Once all the patients are parsed, the conversion map is used to construct a back-end data packet that is uploaded to the back-end CDMS. In some embodiments, the parsing step further comprises verifying that clinical identifiers have been set for the patient, wherein, when the clinical identifiers have not been set for the patient, data in the front-end data packet associated with the patient is rejected. In some embodiments of the present invention, the back-end study definition is an Oracle Clinical definition and the front-end study definition is a macro study definition.

Another aspect of the present invention provides a method for electronically resolving a discrepancy arising in a CDMS. The method comprises converting, using a conversion map, the discrepancy from a back-end format, used to store a clinical value corresponding to the discrepancy, into a front-end format that is compatible with a front-end study definition. Further, the discrepancy is transferred, in the front-end format, to a front-end site where the clinical value associated with the discrepancy was first entered. A discrepancy response is received from the front-end site. When the discrepancy response resolves the discrepancy, the discrepancy response is stored in the CDMS, thereby resolving the discrepancy.

In some embodiments, the method further comprises determining whether the discrepancy response resolves the discrepancy by: (i) converting the discrepancy response from the front-end format to the back-end format, and (ii) verifying that the discrepancy response satisfies a data entry criterion associated with the clinical value. The data entry criterion may be, for example, a data type or a data range.

In some embodiments, the CDMS includes: (1) a database to store the clinical value, (2) a SAS module to analyze the clinical value using statistics, (3) a generic loader to load data not found in a case report form, (4) a thesaurus module to access a thesaurus that harmonizes adverse reaction terminology, and (5) an audit trail module to access an audit trail. In some embodiments, the conversion map stores a one-to-one correspondence between respective questions and events in the back-end format and respective questions and events in the front-end study definition.

Another embodiment of the present invention provides a computer readable memory used to direct a client/server system to function in a specified manner. The computer readable memory includes a back-end clinical data management system (CDMS). The back-end CDMS is capable of saving data in accordance with a back-end clinical definition. The computer readable memory further includes a remote data entry module for collecting clinical data in accordance with a front-end study definition. The computer readable memory further includes a mapper server module for resolving a discrepancy arising in the back-end CDMS. The mapper server module includes executable instructions stored in the computer readable memory. The executable instructions include instructions for converting, with a conversion map, the discrepancy from the back-end clinical definition format used to store a clinical value corresponding to the discrepancy into the front-end study definition format. The executable instructions further include instructions for transferring the discrepancy, in the front-end study definition format, to a front-end site where the clinical value associated with the discrepancy was entered. The executable instructions further include instructions for receiving a discrepancy response from the front-end site as well as instructions for storing the discrepancy response in the back-end CDMS when the discrepancy response resolves the discrepancy.

6. BRIEF DESCRIPTION OF THE, DRAWINGS

Additional objects and features of the invention will be more readily apparent from the following detailed description and appended claims when taken in conjunction with the drawings, in which:

Figure 11:
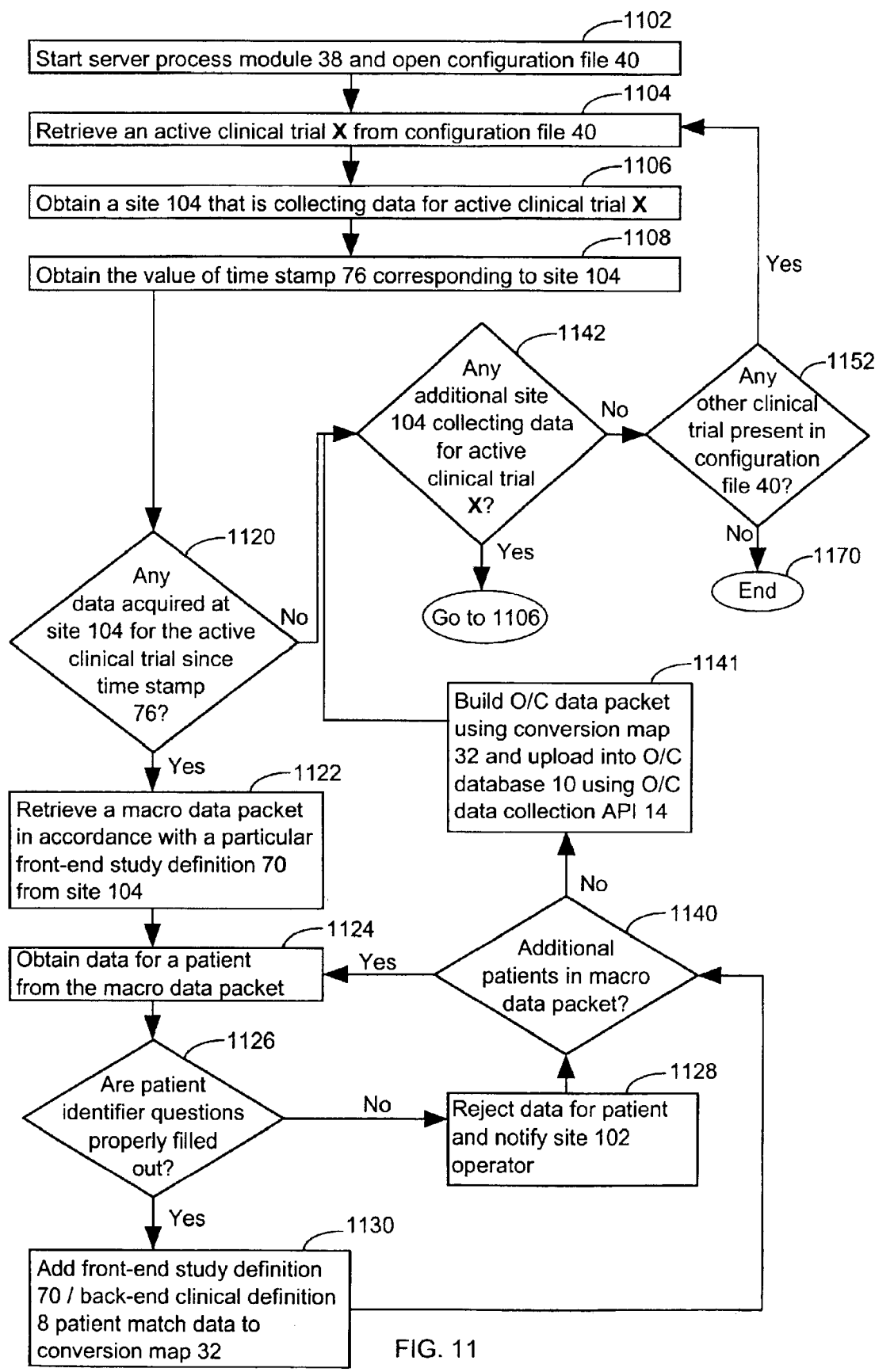
Figure 12:
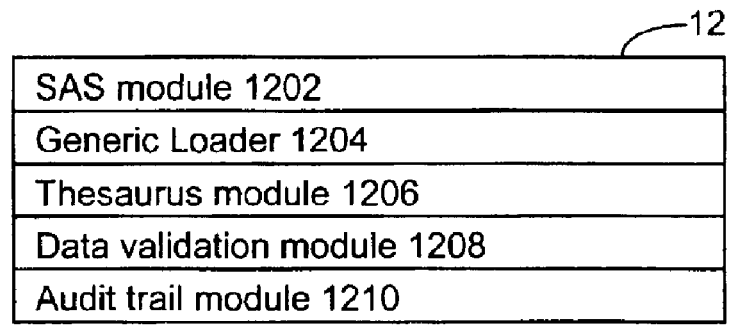
Figure 14:
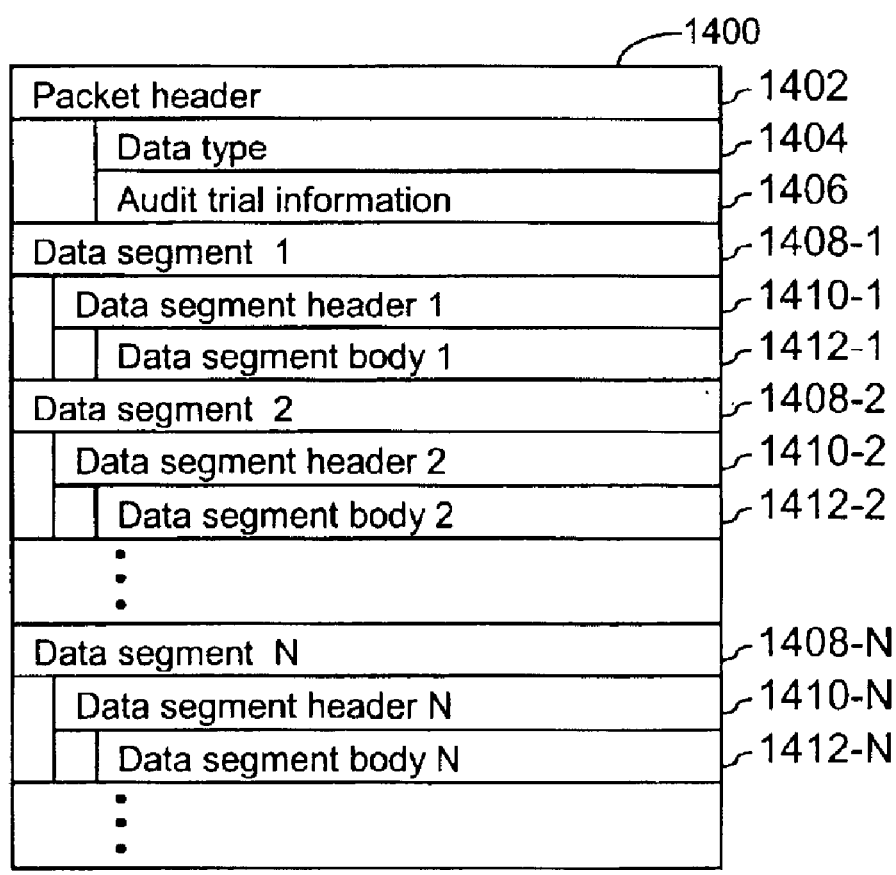
Figure 13:
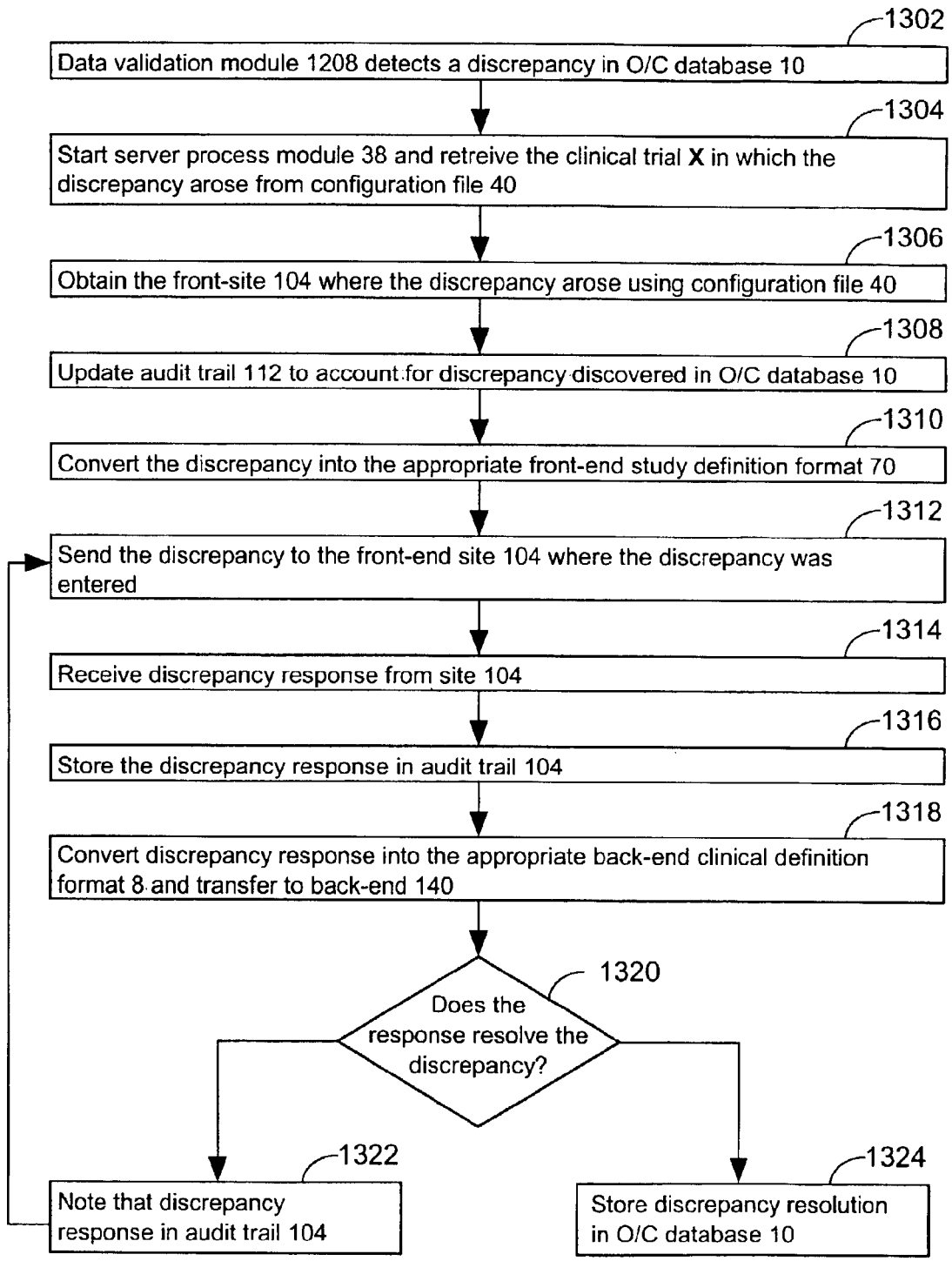
Figure 15:
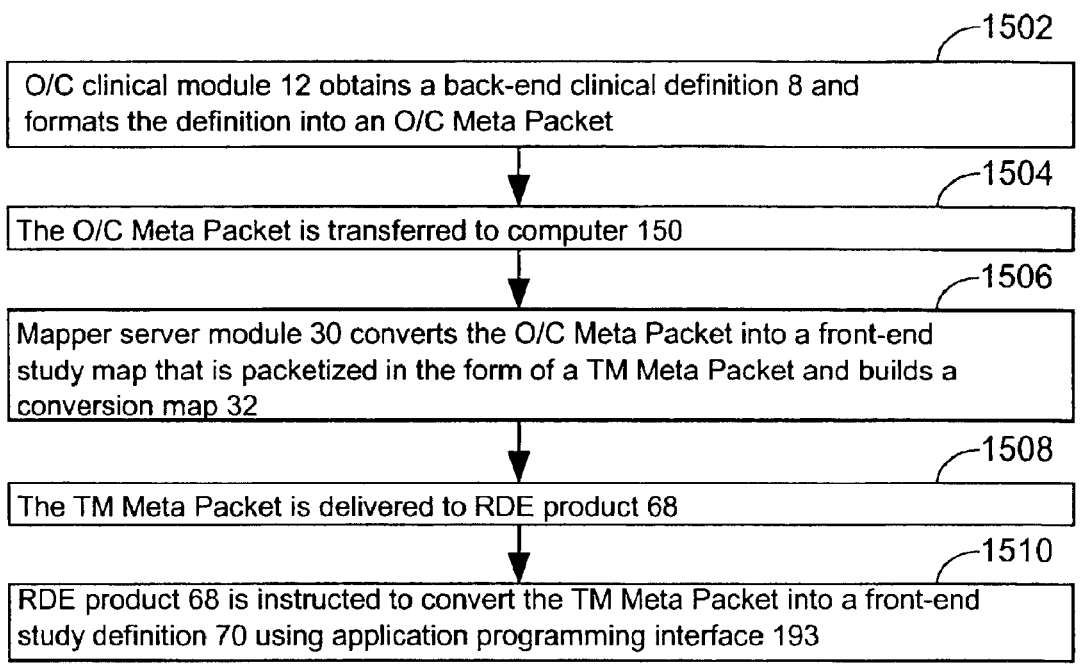
Figure 16:
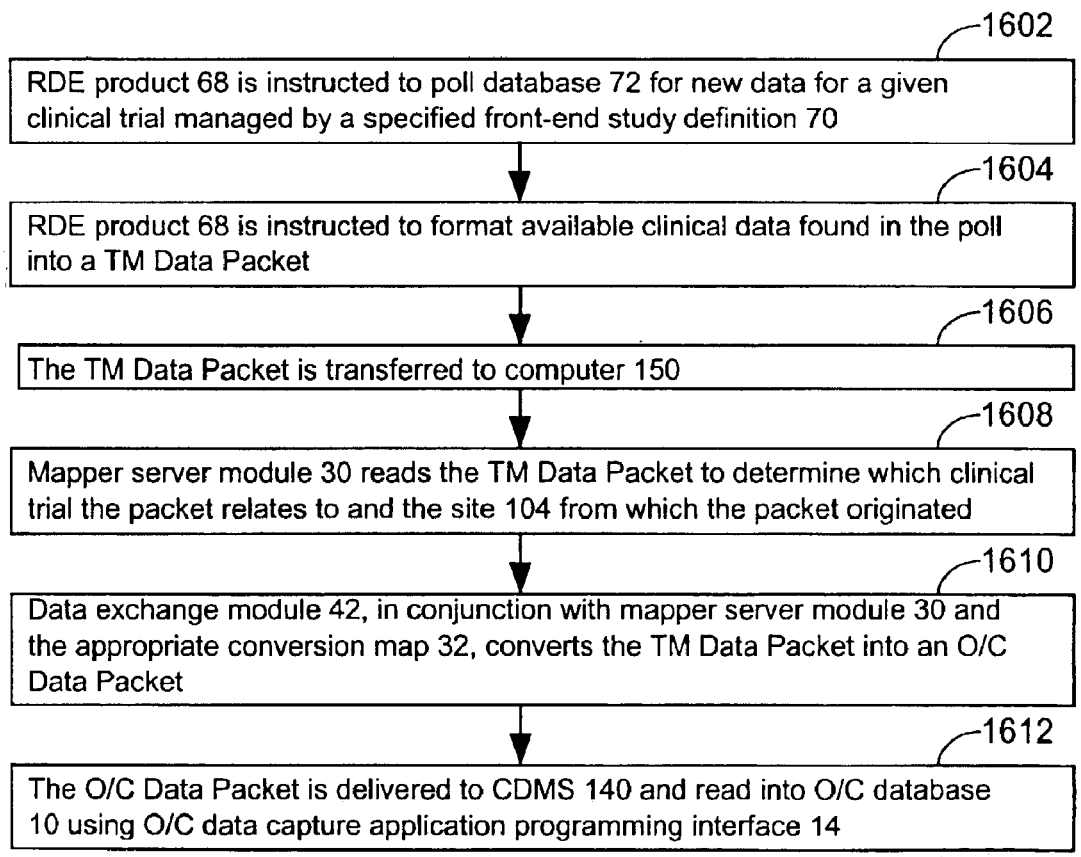
Figure 17:
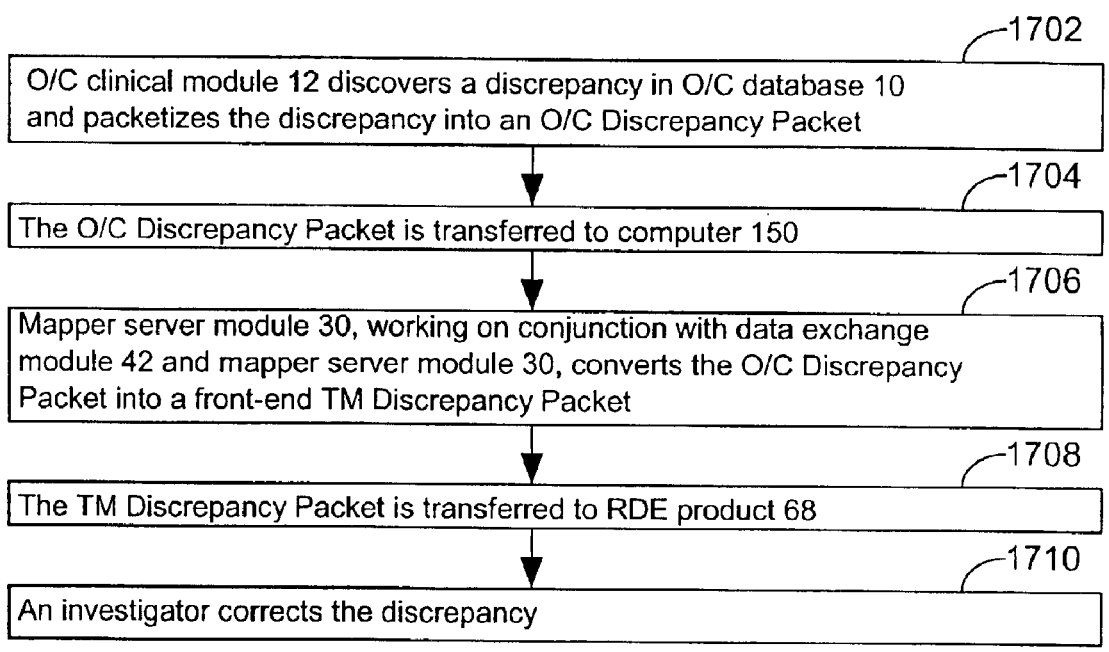

FIGS. 7A, 7B, and 7C respectively illustrate exemplary OcCpEvent, OcDci, and OcDciMod segments of a conversion map in accordance with one embodiment of the present invention;

FIGS. 8A, 8B, and 8C respectively illustrate exemplary OcQuestion, TmDerivedItem, and OcSite segments of a conversion map in accordance with one embodiment of the present invention;

FIGS. 9A, 9B, and 9C respectively illustrate exemplary OcInvestigator, OcPatient, and OcKey segments of a conversion map in accordance with one embodiment of the present invention;

FIG. 10 illustrates an exemplary SpecialValues segment of a conversion map in accordance with one embodiment of the present invention;

FIG. 11 illustrates processing steps for obtaining clinical data from a front-end clinical site in accordance with one embodiment of the present invention;

FIG. 12 illustrates software modules found in an O/C clinical module in accordance with one embodiment of the present invention;

FIG. 13 illustrates processing steps for resolving a discrepancy that arises in a back-end clinical data management system, in accordance with one embodiment of the present invention;

FIG. 14 illustrates a packet formatted in a back-end and front-end independent data structure in accordance with one embodiment of the present invention;

FIG. 15 illustrates processing steps for converting a back-end clinical definition into a front-end study definition in accordance with one embodiment of the present invention;

FIG. 16 illustrates processing steps for transferring clinical data from a front-end clinical site to a back-end clinical data management system in accordance with one embodiment of the present invention; and FIG. 17 illustrates a method of using a data packet structure to resolve a discrepancy in a back-end clinical data management system in accordance with one embodiment of the present invention.

Like reference numerals refer to corresponding parts throughout the several views of the drawings.

7. DETAILED DESCRIPTION OF THE INVENTION

The present invention provides an apparatus and method for integrating front-end data collection systems with a back-end CDMS such as Oracle Clinical. The present invention orchestrates bi-directional conversion and transportation of data, metadata, and process data between front-end data collection systems and back-end clinical data management systems. The present invention is capable of operating continuously at a plurality of back-end data warehousing sites. A number of aspects of the instant invention are accessible via open application program interfaces ("API"). In addition, the present invention provides an API that acts as a client to front-end data collection systems as well as an additional API that acts as a client to the back-end CDMS.

In one embodiment, the present invention provides an interface between a front-end data collection system having Remote Data Entry capabilities, such as MACRO from InferMed, Ltd., London UK, with a legacy back-end CDMS, such as Oracle Clinical (O/C), Oracle Inc., Redwood Shores, Calif. MACRO and Oracle Clinical were developed independently and have no common standards for data or metadata representation. Thus, one embodiment of the present invention provides an automated interface between these two products. The inventive apparatus and method interprets O/C study definitions and converts them to macro study definitions. The converted macro study definitions are then loaded into MACRO. The macro study definitions serve as a basis for collecting clinical data using MACRO. As study data is collected using MACRO, the instant invention translates the macro study data into a data format that can be read by O/C and loads the formatted data, on an incremental basis, into a designated O/C server. Thus, the present invention provides three important use case scenarios, (i) mapping a back-end clinical definition to a front-end study definition, (ii) retrieving and translating clinical data from a Remote Data Entry program, such as MACRO, and populating a back-end CDMS with the retrieved clinical data, and (iii) resolving discrepancies that are discovered in the back-end CDMS electronically and in a fully audited fashion.

7.1 OVERVIEW OF SYSTEM COMPONENTS USED IN THE PRESENT INVENTION

Figure 1:
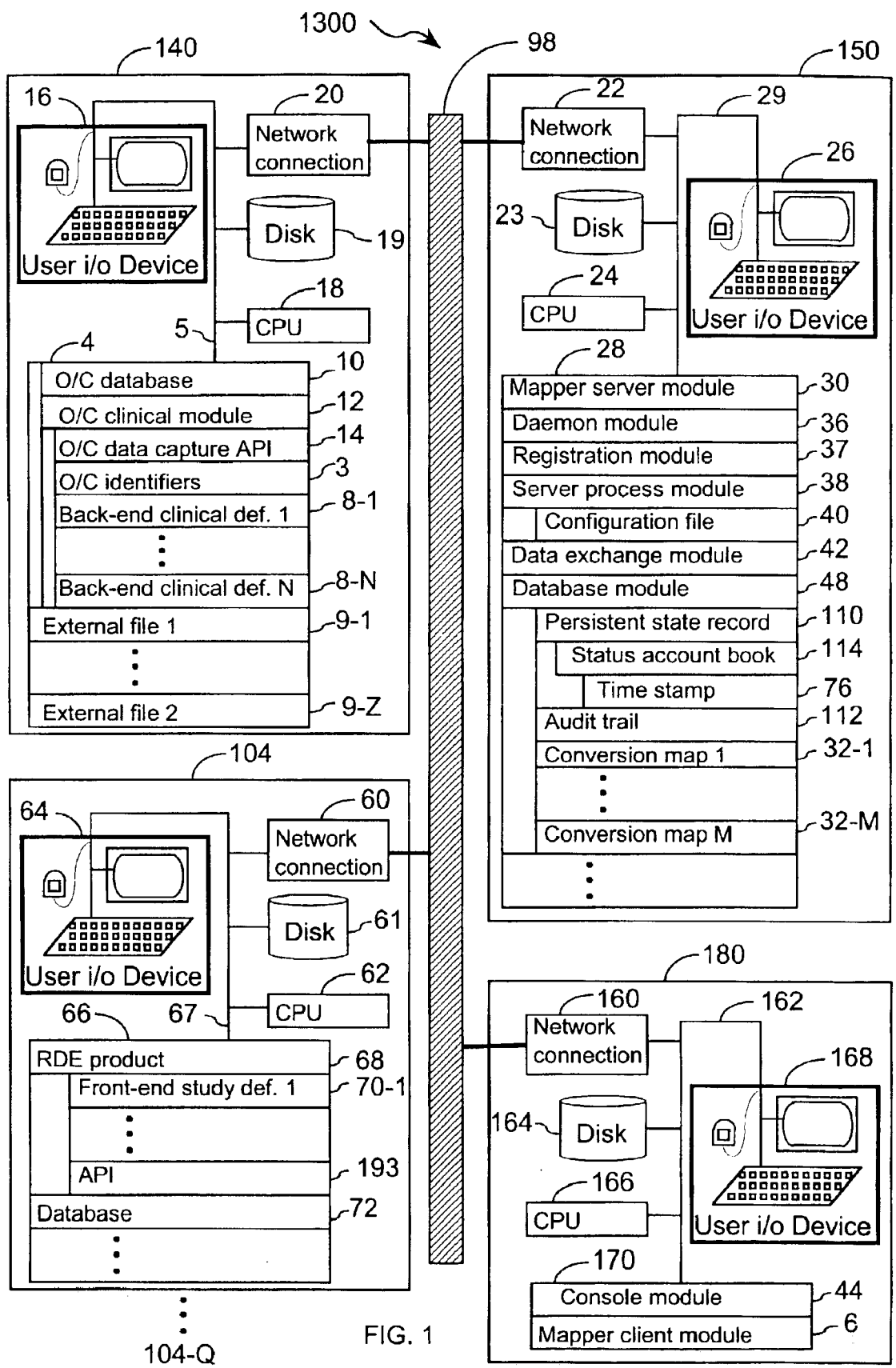
FIG. 1 illustrates an exemplary computer system network with which the present invention may be implemented.

The present invention provides a set of component software modules and databases that are linked together by an intranet, internet, or other wired or wireless communications systems, referred to herein as a transmission channel. A significant advantage of the present invention is that the component software modules can be configured to function when the individual component software modules are separated by large geographical distances. Another advantage of the present invention is that the system can be scaled to handle a wide range of work loads. FIG. 1 shows an exemplary system, such as system 1300, for converting a back-end clinical definition 8 to a front-end study definition 70 using the methods of the present invention. In one embodiment, back-end clinical definition 8 is an Oracle Clinical definition and front-end study definition 70 is a macro study definition. System 1300 preferably includes the hardware and software components illustrated in FIG. 1, including a back-end computer 140 that hosts a back-end O/C database 10, a server 150 that hosts a server process module 38, one or more front-end sites 104, each having a Remote Data Entry (RDE) product 68, a transmission channel 98, and clients 180 that host a console module 44 and/or a mapper client module 6.

In an overview to FIG. 1, a back-end clinical definition 8 in O/C database 10 on computer 140 is selected by mapper client module 6 resident on computer 180. The selected back-end clinical definition 8 is then converted to a front-end study definition 70 by mapper server module 30 on computer 150. The data format of back-end clinical definition 8 is quite different from that of front-end study definition 70. In fact, many of the attributes and metatables found in back-end clinical definitions 8 simply are not used in front-end study definition 70. These unused metatables and attributes are usually stored in a conversion map (e.g., study map) 32 on computer 150 that is created by mapper server module 30 during conversion of back-end clinical definition 8 to front-end study definition 70. Furthermore, the conversion map 32 stores the one to one correspondence between questions and events in the back-end clinical definition 8 and the front-end study definition 70. Once converted, a front-end study definition 70 is distributed to front-end sites 104. After clinical data are received by front-end sites 104, server process module 38 (on computer 150) queries each database 72 for clinical data and adds the clinical data to conversion map 32. After each front-end site 104 is queried, data in conversion map 32 is used to construct a novel back-end data packet that may be read by O/C database 10.

Now that a broad overview of FIG. 1 has been given, attention now turns to front-end site 104 in FIG. 1. In fact, in a typical implementation of system 1300, there exists any number of front-end sites 104 spread out over large geographical distances. For example, each front-end site 104 may be located at a remote clinical site. In a preferred embodiment, each front-end site 104 includes:

a central processing unit 62;

a main non-volatile storage unit 61, preferably a hard disk drive, for storing software and data;

a network connection 60 for connecting front-end site 104 to transmission channel 98, which may be any wired or wireless transmission channel;

a system memory 66, preferably RAM, for storing system control programs, data, and application programs, including programs and data loaded from non-volatile storage unit 61;

a user interface 64, including one or more input devices; and an internal bus 67, for interconnecting the aforementioned elements to the system.

Operation of each front-end site 104 is controlled by means of an operating system or a round-robin scheme in accordance with methods well known in the art. In a typical implementation, system memory includes the means for controlling front-end site 104 as well as a number of software modules and data structures used in the instant invention. These software modules and data structures include RDE product 68, one or more front-end study definitions 70, and database 72. Typically, a portion of one or more of these modules is stored on non-volatile storage unit 61. The function and purpose of each of these software modules will now be described.

RDE product 68. In one embodiment of the present invention, RDE product 68 is version 3.0 of a set of applications and utilities ("MACRO") provided by InferMed Ltd., London, England. RDE product 68 is used to display a set of forms to a data entrant. The forms are highly specialized and present questions to the data entrant in a highly regularized manner. For example, each question present in a form may be restricted to a range of values. In addition, the RDE product 68 includes extensive scheduling information for each form presented. For example, in a multi-week trial, a form for each patient registered in the trial may be presented to the data entrant on a weekly basis in accordance with a schedule maintained by RDE product 68.

Front-end study definition 70. Each front-end study definition 70 defines the data format needed to facilitate Remote Data Entry at a particular trial site and study. An advantage of the present invention is that each front-end study definition 70 is electronically generated based on a corresponding back-end clinical definition 8 (FIG. 1). In one embodiment of the present invention, front-end study definition 70 is a MACRO 3.0 (InferMed) macro study definition that includes the metatables described in Table 2.

TABLE 2

Description of selected metatables in one embodiment of front-end study definition 70

| Metatable Name | Metatable Function |
|---|---|
| ClinicalTrial | The name or identifier for a particular clinical trial that is being conducted using system 1300. |
| StudyDefinition | Header information that describes basic properties of the ClinicalTrial, such as the number of patients to be enrolled in the study. |
| TrialStatusHistory | The number of patients that have been recruited so far. |
| ReasonForChange | Tracks the reasons why any answers to questions were subsequently changed by the data entrant, so that the integrity of the clinical trial is maintained. |
| ValueData | Allowed answers to a DataItem. |
| DataItem | Clinical question and clinical question attributes, such as whether alphanumeric response is allowed. |
| DataItem validation | Range of values allowed in response to a DataItem. |
| CaseReportFormPage | Size of form (page size), description of form, including possible logo. |
| CaseReportFormElement | Describes the location of an element, such as a DataItem on the CaseReportFormPage |
| StudyVisit | Name of a clinical visit and the date |
| StudyVisitCaseReportFormPage | A link to a page in as StudyVisit |
| TrialPhase | ClinicalTrial phase |

More details on these macro metatables can be found in the technical documentation for MACRO v.3.0, Infermed Ltd., London, England. Furthermore, a description of how the metatables listed in Table 2 are generated based on a corresponding back-end clinical definition 8 will be disclosed under "Use Case 1" below.

API 192. Application programming interface (API) 192 is provided by some embodiments of RDE 68. API 192 provides a mechanism for uploading information into RDE 68 and database 72 in a manner that insulated from the internal data structure of database 72.

Database 72. In one embodiment of the present invention, database 72 is an installation of the Oracle 9i database, Redwood Shores, Calif. Database 72 stores clinical data in accordance with a front-end study definition 70.

Turning attention to back-end computer 140 in FIG. 1, computer 140 preferably includes:

- a central processing unit 18;
- a main non-volatile storage unit 19, preferably a hard disk drive, for storing software and data;
- a network connection 20 for connecting back-end computer 140 to transmission channel 98;
- a system memory 4, preferably RAM, for storing system control programs, data, and application programs, including programs and data loaded from non-volatile storage unit 19;
- a user interface 16, including one or more input devices; and
- an internal bus 5, for interconnecting the aforementioned elements to the system.

Operation of back-end computer 140 is controlled by means of an operating system or a round-robin scheme in accordance with methods well known in the art. In a typical implementation, system memory includes the means for controlling back-end computer 140 as well as a number of software modules, data files and databases used in the instant invention. Typically, portions of these software modules, data files and/or databases are stored in non-volatile storage unit 19. These software modules, data files, and/or databases include an O/C database 10 and, optionally, one or more external files 9. O/C database 10 works in conjunction with an O/C clinical module 12 and an O/C data capture API 14. In some embodiments of the present invention, O/C database 10 stores O/C identifiers 3 and one or more back-end clinical definitions 8. The function and purpose of each of these software modules, data files and/or databases will now be described.

O/C database 10. O/C database 10 is a database management system for storing and retrieving clinical data. A database management system is a software program that typically operates on a database server or mainframe system to manage data, accept queries from users about the data, and respond to those queries. In some embodiments, a database management system is capable of: (i) providing a way to structure data as records, tables, or objects, (ii) accepting data input from operators and storing that data for later retrieval, (iii) providing a query language for searching, sorting, reporting, and other decision support activities that help users correlate and make sense of the collected data, (iv) providing multi-user access to the data, along with security features that prevent some users from viewing and/or changing certain types of information, (v) providing data integrity features that prevent more than one user from accessing and changing the same information simultaneously, and (vi) providing a data dictionary that describes the structure of the database, related files, and record information.

Most database management systems, such as that hosted by back-end computer 140, are client/server based and operate over networks. In the embodiment illustrated in FIG. 1, the server is the back-end computer 140, whereas the clients include front-end sites 104, clients 180 or other undisclosed clients within system 1300. Database management systems include an engine that runs on a back-end computer 140 with a high-performance channel to the large data store. The back-end computer accepts requests from clients, such as client 180, that may require sorting and extracting data. A typical language for accessing most database systems is SQL (Structured Query Language). In one embodiment, back-end computer 140 uses an Oracle database management system that is responsive to SQL queries. Therefore, in one embodiment, O/C database 10 is an Oracle database, such as Oracle 9i (Oracle, Redwood Shores, Calif.).

In another embodiment of the present invention, O/C database 10 is a flat-file database. Flat-file databases are generally applicable to simple data systems, since all the information can be stored in one file. In another embodiment, O/C database 10 is a relational database system and/or object-oriented database system. A relational database management system stores clinical data in multiple tables or metatables. The tables are related and combined in a number of ways to correlate and view the data. A typical O/C database 10 might contain hundreds of tables that potentially produce thousands of relationships. A common element, such as a patient ID or clinical trial ID, may link information across the tables.

Object-oriented databases, which are within the scope of the preferred embodiments for O/C database 10, generally include the capabilities of relational databases but are capable of storing many different data types including images, audio, and video. Additionally, object oriented databases are adapted to store methods, which include properties and procedures that are associated with objects directly in the database. A variety of references are publicly available for further information on implementing relational and/or object oriented databases for enabling the implementation of the systems and methods disclosed herein; see, for example, Cassidy, High Performance Oracle8 SOL Programming and Tuning, Coriolis Group (March 1998), and Loney and Koch, Oracle 8: The Complete Reference, (Oracle Series), Oracle Press (September 1997), the contents of which are hereby incorporated by reference into the present disclosure.

O/C clinical module 12. In one aspect of the present invention, O/C clinical module 12 is a product of Oracle Corporation, Redwood Shores, Calif. For example, in one embodiment, O/C clinical module 12 is version 3.1.1.1 of Oracle Clinical and O/C database 10 is Oracle database version 7.3.2. In this embodiment, the Oracle database version 7.3.2 seat is the O/C database 10. In another embodiment of the present invention, O/C clinical module 12 is Oracle Clinical v4i. O/C clinical module 12 is used to store back-end clinical definitions 8 within O/C database 10. In another embodiment of the present invention, O/C clinical module 12 is Clintrial 4.3 (Phaseforward, Waltham, Mass.). Those of skill in the art will appreciate that there are other commercial implementations of O/C clinical module 12. In addition, O/C clinical module 12 may be a hybrid between commercially available products and highly customized software that is not commercially available.

O/C data capture API 14. Optionally, some embodiments of the present invention include O/C data capture API 14. O/C data capture API 14 is an application programming interface ("API"). In one embodiment of the present invention, O/C data capture API 14 is Oracle Clinical Data Capture provided by Oracle Clinical for uploading back-end data packets from clinical field offices.

O/C identifiers 3. Optionally, some embodiments of the present invention include O/C identifiers 3. O/C identifiers 3 describe the corresponding O/C site, O/C investigator and O/C patient code for a particular back-end clinical definition 8.

Back-end clinical definition 8. As illustrated in FIG. 1, system 1300 includes a number of back-end clinical definitions 8 such as Oracle Clinical definitions. Back-end clinical definitions 8 in system 1300 are stored in a database such as O/C database 10. In FIG. 1, there is a set of N back-end clinical definitions 8 stored in O/C database 10.

In one embodiment of the present invention, back-end clinical definition 8 is an Oracle Clinical definition include the metatables described in Table 3.

TABLE 3

Description of selected metatables in one embodiment
of back-end clinical definition 8

| Metatable Name | Metatable Function |
| --- | --- |
| CLINICAL_PLANNED_EVENT | Name or serial number for a clinical event, such as: clinical_planned_event_id, planned_study_interval_id |
| CLINICAL_STUDY | Short description of a clinical event, including the number of patients expected and the number of patients enrolled. |
| DATA_COLLECTION_INSTRUMENT (DCI) | A series of data entry questions used in the clinical event. The DCI includes clinical questions and clinical question attributes. |
| DCI_BOOK | A series of question classifications (sets of DCIs) that are presented to the data entrant for a given patient over the course of a clinical trial. |
| DCI_BOOK_PAGE | One page in DCI_BOOK. The page may include one or more DCIs. |
| DCI_INSTRUMENT_MODULE | Reference to a DCI_BOOK_PAGE in the DCI_BOOK |
| DATA_COLLECTION_MODULE (DCM) | A group of DCIs |

TABLE 3-continued

Description of selected metatables in one embodiment of back-end clinical definition 8

| Metatable Name | Metatable Function |
| --- | --- |
| DCM_LAYOUT_ABS_PAGE | The layout of a 80 × 40 legacy display used by O/C data collection API 14 to display DCIs and DCMs. |
| DCM_LAYOUT_GRAPHIC | A graphic displayed on the DCM_LAYOUT_ABS_PAGE |
| DCM_LAYOUT_PAGE | A link between a DCM and a page in a DCI_BOOK. |
| DCM_LAYOUT_TEXT | A caption to a question. For example "Gender?" |
| DCM_QUES_REPEAT_DEFAULT | The default number of times the group of DCIs in the DCM will be presented to the data entrant. |
| DCM_QUESTION | Screen attributes of a DCI. |
| DCM_QUESTION_GROUP | The Attributes of a DCM question group |
| DCM_SCHEDULE | When a DCM will be presented to the data entrant for a given patient. |
| DISCRETE_VALUE | Allowed response to a DCI. |
| DISCRETE_VALUE_GROUP | Allowed response to a DCI. |

More details on the structure of the aforementioned metatables are found in the O/C v.3.1.1.1 stable-views documentation, Oracle Corporation, Redwood Shores, Calif.

External files 9. Optionally, some embodiments of the present invention include external files 9. Back-end clinical definitions 8 may be exported from the O/C database 10 and stored as external files 9. An external file 9 contains the complete description of the data structure in an internal back-end clinical definition 8. One difference between an external file 9 and a back-end clinical definition 8 is that the back-end clinical definition 8 is stored as a collection of metatables within O/C database 10 whereas the corresponding file 9 contains a complete, metatable independent, description of the clinical study. It will be appreciated that the present invention imposes no requirements on the location of external files 9 within system 1300 provided that they are at a location that is addressable by system 1300.

In one embodiment of the present invention, back-end computer 140 is a clinical data management system (CDMS). A CDMS stores clinical trial results in a database, such as O/C database 10. In one embodiment of the present invention, a CDMS is defined as any computer that supports the following core functionality: (1) a database to store clinical trial data, (2) access to SAS functionally to analyze the clinical trial data using statistics, (3) a generic loader to load data not found in a case report form, (4) a thesaurus to harmonize adverse reaction terminology, (5) any applicable data validation procedures, and (6) an audit trail. In some embodiments of the present invention, the database used to store clinical trial data is O/C database 10.

In some embodiments of the present invention, the core functionality of a CDMS, apart from the database, is found in O/C clinical module 12. FIG. 12 illustrates an exemplary O/C clinical module 12 in accordance with one embodiment of the present invention. In FIG. 12, O/C clinical module includes SAS module 1202. In some embodiments, SAS module 1202 is a statistical package available from SAS (Cary, N.C.) that is used to statistically analyze clinical data. In other embodiments, SAS module 1202 is a mechanism for exporting data from O/C database 10 into a form that may be analyzed by a statistical package, such as SAS. It will be appreciated that, while SAS is a preferred statistical package in accordance with the present invention, other statistical programs may be used to carry out core CDMS functionality, and that all such programs are encompassed within the scope of the present invention.

The exemplary O/C clinical module 12 illustrated in FIG. 12 further includes a generic loader module 1204. In one embodiment, generic loader module 1204 loads data not found in a case report form. Such data includes, for example, lab results such as blood tests and electrocardiogram analyses. The case report form is used at front-end sites to obtain clinical data. However, it is often the case that some of the data for a clinical trial can only be derived from lab results. Many lab tests are performed at centralized locations long after a clinical subject has left the front-end site. Therefore, case report forms are not used to report lab results. Instead, lab results are communicated from the laboratories where testing is performed directly to the CDMS. Generic loader module 1204 receives this data and matches the data with the correct clinical subjects. The data is then stored in O/C database 10.

The exemplary O/C clinical module 12 illustrated in FIG. 12 further includes a thesaurus module 1206 in order to harmonize adverse reaction terminology. For example, in practice, one clinician may diagnose a headache as a "headache" while another clinician may diagnose a headache as a "migraine." Further, one clinician may capitalize headache (i.e. "Headache") while other clinicians might not. Thus, even for the simple symptoms such as a headache, there may be a great deal of diversity in how the term is recorded. Thesaurus module 1206 harmonizes this terminology using a standard dictionary of medical terms. In one embodiment, the dictionary of medical terms is the MedDRA dictionary. MedDRA, an International Conference on Harmonization (ICH) initiative, is a standardized dictionary of medical terminology. MedDRA is based on the UK Medicines Control Agency's (MCA) medical terminology. It incorporates World Health Organization Adverse Reaction Terminology (WHO-ART; WHO Collaborating Center for International Drug Monitoring, Uppsala, Sweden), regulatory related terminology from the International Classification of Diseases (ICD) and from the International Classification of Diseases with Clinical Modification (ICD-CM), Coding Symbols for a Thesaurus of Adverse Reaction Terms (COSTART; Department of Health, Education and Welfare; Food and Drug administration, Rockville, Md.) and Japanese Adverse Reaction Terminology (J-ART). In other embodiments, other terminology thesaurus are used by thesaurus module 1206, such as World Health Organization Adverse Reaction Dictionary (WHO ARD), COSTART, or the Hoechst Adverse Reaction Terminology System (HARTS).

The exemplary O/C clinical module 12 illustrated in FIG. 12 further includes a data validation module 1208 for validating clinical data. An advantage of the present invention is that some forms of data validation may be performed using the front-end data acquisition product (e.g., FIG. 1; RDE product 68). For example, product 68 may be used to ensure that data entries fall within allowed ranges. Even though product 68 can be used for some forms of data validation, a CDMS must have a data validation module to handle some forms of data validation that are not easily performed using product 68. The types of data validation that are not easily run using product 68, and therefore must be performed by a CDMS, are best illustrated by example. In one example, a clinical trial may require a check across a large clinical population to see if a significant percentage of the entire population has a particular side effect. Such a check is not easy to perform using RDE product 68 because any given installation of RDE product 68 will only have access to patient data that was collected at the site where the RDE product 68 is installed. Since a clinical trial typically involves many remote sites spread across a very large geographical region, an RDE product 68 simply will not have readily available access to the patient data necessary to perform a check across a large clinical population.

The exemplary O/C clinical module 12 illustrated in FIG. 12 further includes an audit trail module 1210 for tracking all changes made to O/C database 10. Audit trail module 1210 is a necessary component of a CDMS system because all data entries in a CDMS system must be audited in order to meet regulatory requirements for submission of clinical data in many countries. Among other tasks, an audit trail tracks how discrepancies in O/C database are discovered and how they are resolved. For example, when a clinician overrides RDE product 68 safeguards and enters a value for a particular clinical event that is not within required ranges, a discrepancy will be triggered by data validation module 1208. In one embodiment of the present invention, data validation module 1208 will communicate the discrepancy to the front-end site 104 that originated the offending data for resolution. Then, a clinician at the front-end will resolve the discrepancy. This resolution will ultimately be transmitted back to the back-end computer 140, thereby resolving the discrepancy. Importantly, audit trail module 1210 keeps track of all of these steps so that at any given time, each step that was performed to resolve a discrepancy can be determined. In one embodiment of the present invention, audit trail module 1210 is compliant with Good Clinical Practice as promulgated by the Food and Drug Administration (FDA). Good Clinical Practice (GCP) is a standard for the design, conduct, performance, monitoring, auditing, recording, analysis, and reporting of clinical trials. Compliance with this standard assures that the data and reported results are credible and accurate and that the rights, safety, and well-being of trial subjects are protected. FDA requires that the biomedical research it regulates conforms to GCP standards as articulated in FDA regulations.

It will be appreciated that a CDMS may use more than one computer to provide the full functionality associated with a CDMS. For example, in some embodiments, data validation module 1208 works in conjunction with database module 48 on computer 150 (FIG. 1), which stores an audit trail 112. However, a CDMS typically does not rely on a front-end site 104 to provide the core functionality associated with a CDMS because a front-end computer typically does not have access to the full set of clinical data found in O/C database 10.

Turning attention to computer 150 in FIG. 1, computer 150 preferably includes:

a central processing unit 24;

a main non-volatile storage unit 23, preferably a hard disk drive, for storing software and data;

a network connection 22 for connecting computer 150 to transmission channel 98;

a system memory 28, preferably high speed random-access memory (RAM), for storing system control programs, data, and application programs, including programs and data loaded from non-volatile storage unit 23;

a user interface 26, including one or more input devices; and an internal bus 29, for interconnecting the aforementioned elements to the system.

Operation of computer 150 is controlled by means of an operating system or a round-robin scheme in accordance with methods well known in the art. In a typical implementation, system memory includes the means for controlling computer 150 as well as a number of software and data modules used in the instant invention. These software and data modules include mapper server module 30, daemon module 36, registration module 37, server process module 38, configuration file 40, data exchange module 42, database module 48, persistent state record 110, status account book 114, one or more time stamps 76, audit trail 112, and conversion maps 32. Typically, a portion of one or more of these software and/or data modules is stored on non-volatile storage until 19. The function and purpose of each of these software and data modules will now be described.

Mapper server module 30. Mapper server module 30 converts a back-end clinical definition 8 or external file 9 into an equivalent front-end study definition 70. It also generates a translation key so that server process module 38 and data exchange module 42 can later translate data collected by RDE product 68 into a data format that is compatible with a back-end clinical definition 8. The translation key is referred to as a conversion map 32.

In one aspect of the present invention, mapper server module 30 provides a user session for each mapper client module 6 when a new connection is established. The user session maintains information while a mapper client module 6 is connected to the mapper server module. Each session is unique to a mapper client module 6. In some embodiments, mapper server module 30 allows only one connection at a time. The user session is created when a mapper client module 6 first calls the startsession( ) method. The user session is deleted when the mapper client module 6 calls the stopsession( ) method. The user session expires if it is idle for more than 30 minutes.

The user session is identified by a user name and a session token that is generated by the client 180 and sent to the computer 150 that hosts mapper server module 30. In an exemplary embodiment, the session token is a unique string generated by the Secure Hash Algorithm (SHA-1) and each method call from a mapper client module 6 contains a session token. The mapper server module 30 validates the session token and the session expiration time for each method call.

In one embodiment of the present invention, an exception is thrown when the session token is not recognized or the user session has expired. For each method call, the user session is retrieved based on the session token. A subset of properties for the study definition exists within the user session. Under such a situation, when back-end clinical definition 8 is changed, this subset of properties is replaced.

In another aspect of the invention, mapper server module 30 provides an IMap Interface. Exemplary mapper server modules 30 support mapper client modules 6 as defined by the IMap public interface shared by the two components. The methods of the Map interface are itemized and described in Table 4 below.

TABLE 4

Public API Provided by the IMap Interface

| Name | Description |
| --- | --- |
| addConfigurationValue | Mapper client module 6 uses this method to send a new property value to Mapper server module 30 for inclusion in a map.properties object. |
| deleteConfigurationValue | Mapper client module 6 uses this method to notify mapper server module 30 of a property value to be deleted from the map.properties object. |
| doLoadStudy | Provides instructions to a load back-end clinical definition 8 for a selected study from O/C database 10. The study is loaded into a temporary location. |
| doSelectStudy | Causes the study definition loaded by the doLoadStudy( ) method to be made. |
| editConfigurationValue | Provides notification that a property value is to be changed in the map.properties object. The new property value is supplied. |
| findElement | Asks mapper server module 30 to find where a study definition question on one server is located in the study definition on another server. |
| generateTMStudyDefinition | Mapper client module 6 sends this request to mapper server module 30 in order to instruct mapper server module to create (or update) a front-end study definition 70 and conversion map 32 based on the currently loaded back-end clinical definition 8. |
| getchildren | Requests mapper server module 30 to provide a set of child nodes used for display in a hierarchical tree. The parent node is provided. |
| getCRFElements | Requests the set of electronic case report form elements that comprise a specific electronic case report form page. The elements are used to display a case report form page to the user. |
| getOCQuestion | Requests the attributes that describe a question in a back-end clinical definition 8. |
| getRootNode | Requests the root node for a specific tree display. A keyword is provided for the requested tree. |
| getServerNameList | Returns a set of names of back-end computers 140 within system 1300. |
| getStudyDescription | Requests a description of a back-end clinical definition 8. Mapper server module 30 sends mapper client module 6 the name of the study on the currently connected back-end computer 140. Mapper server module 30 returns a text string. |
| getStudyNameList | Upon receiving this request from mapper client module 6, mapper server module 30 returns the names of the clinical studies that are present on the currently-connected back-end computer 140. |
| queryTMStudyStatus | Upon receiving this request, mapper server module 30 determines whether a front-end study definition 70 and corresponding conversion map 32 should be created or updated. Mapper client module 6 is sent a response that is displayed to the user. |
| readOCMetaFile | Upon execution of this command, mapper server module 30 creates an OCMetaPacket by opening a local file and converting it to an OCMetaPacket. Mapper server module 30 loads the OCMetaPacket and sets it to be the currently selected back-end clinical definition 8. |
| saveStudyDefinition | Updates MACRO server module 30 with the currently generated front-end study definition 70, and updates computer 150 with the currently generated conversion map 32. |
| startSession | Called by a mapper client module 6 to create a new user session. |
| stopSession | Called by a mapper client module 6 to stop and discard the current user session. |
| writeOCMetaFile | Requests currently selected back-end clinical definition 8 back to mapper client module 6 as an OCMetaPacket. Mapper client module 6 or data exchange module 42 converts the OCMetaPacket to a file for local storage. |

Daemon module 36. Daemon module 36 acts as the activation mechanism for server process module 38, Mapper server 30, and data exchange module 42. When an instance of the invention is started, daemon module 36 starts and automatically launches server process module 38. Daemon module 36 waits for requests to start additional server processes and to restart server process module 38 when it is stopped. In one embodiment, daemon module 36 requires little intervention and as such does not have a user interface. However, in another embodiment, it does act as the system console for all output messages and as such is typically available for monitoring when necessary.

Registration module 37. Within registration module 37, entries for different back-end computers 140 in system 1300 are placed when the servers are ready to be used. Queries to use different servers are sent to registration module 37, and the registration module replies with a reference to the requested module. If a module 38, 30 or 42 is not available when it is requested, daemon module 36 is contacted, and the corresponding server is started.

Server process module 38. Server process module 38 works in conjunction with data exchange module 42 to collect clinical data from each front-end site 104 and, using the appropriate conversion map 32, to translate the data into a back-end data packet that can be read by O/C database 10. In some embodiments of the present invention, server process module 38 includes scheduling functionality. This scheduling functionality is used to time the frequency in which front-end sites 104 are polled for new clinical data.

Server process module 38 also interacts with database module 48 to keep a persistent record of its state. This record is stored as persistent state record 110 in database module 48. Persistent state record 110 includes the state of external system connections (to 140 and 104), the state of current data load progress, as well as statistical information about load events.

Server process module 38 also stores an audit trail of events 112 in database module 48. Audit trail 112 is categorized into either "Activity" or "Error" event types. In a preferred embodiment, these events are stored historically and are accessed via queries using languages such as structured query language (SQL).

Server process module 38 works in conjunction with other files and software modules, including configuration file 40, data exchange module 42 and console module 44.

Configuration file 40. Configuration file 40 contains installation-specific settings, including selections of the appropriate O/C database 10 and database 72 instances to bridge as well as a list of clinical trials to watch. For each clinical trial watch specified by server process module 38, a special designation is made as to whether the trial is in "test mode." When a trial is in "test mode," data is loaded into O/C clinical module 12 test tables rather than O/C clinical module 12 production tables.

Data exchange module 42. This module provides an interface to front-end sites 104. This module allows a front-end study definition 70 to be loaded into an RDE product 68. This module works in conjunction with server process module 38 to extract new patient data out of front-end sites 104 so that it can be loaded into O/C database 10. In one embodiment, data exchange module 42 works in conjunction with server process module 38 to receive clinical data from a front-end site 104 and translate the data into a form that is compatible with O/C clinical module 12. This process is described with more detail below in the section entitled "Use case 2."

Database module 48. In a preferred embodiment, database module 48 is supported by an Oracle 9i database server. Database module 48 provides a persistent repository for the storage of information used or generated by server process module 38. In some embodiments, database module 48 includes persistent state record 110, audit trail 112, status account book 114, and conversion maps 32.

Persistent state record 110. Persistent state record 110 includes an ACTIVITY_EVENT database table that records all of the events detected by server process module 38. Persistent state record 110 also includes an ERROR_EVENT database table that records all of the errors detected by server process module 38. Persistent state record 110 further includes STATUS_ACCOUNT and STATUS_ACCOUNT_LINE database tables that store the status of each of the studies and front-end sites 104, and the time that the last patient information was loaded. Server process module 38 uses this information when polling sites for new patient information. Database module 48 also includes a STUDY_AUDIT database table that stores the results of audits performed on studies. A study is audited when it is first loaded or when a study is updated.

Status Account book 114 and time stamps 76. Status account book 114 is part of persistent state record 110 and it keeps two time stamps 76 per front-end site 104. The first time stamp 76 designates the last successfully loaded front-end clinical response data. The second time stamp designates the most recent time stamp for the front-end site 104 at which time O/C identifiers 3 were still missing for a patient. Thus, some time stamps 76 represent the time and date of the last data access from server process module 38 of computer 150. Accordingly, when server process module 38 interrogates front-end site 104 for clinical data, the time stamp 76 that corresponds to a chosen front-end study is queried. Then, all data that has been entered into the database 72 for the front-end study definition 70 since the time stamp 76 was last set is transferred to computer 150 for processing.

Conversion maps 32. Each conversion map 32 comprises a key that includes the listings of visits, forms, questions, etc. for a front-end study definition 70 and the corresponding back-end clinical definition 8. Once data translation is started by data exchange module 42, the conversion map 32 is updated with the corresponding patient numbers used for each patient by the front-end study definition 70 and the corresponding back-end clinical definition 8.

Now reference will be made to client 180. Client 180 includes:

a central processing unit 166;

a main non-volatile storage unit 164, preferably a hard disk drive, for storing software and data;

a network connection 160 for connecting client 180 to transmission channel 98;

a system memory 170, preferably RAM, for storing system control programs, data, and application programs, including programs and data loaded from non-volatile storage unit 164;

a user interface 168, including one or more input devices; and an internal bus 162, for interconnecting the aforementioned elements to the system.

Operation of client 180 is controlled by means of an operating system or a round-robin scheme in accordance with methods well known in the art. In a typical implementation, system memory includes the means for controlling client 180 as well as one or more software modules used in the instant invention. These software module include console module 44 and/or mapper client module 6. The function and purpose of each of these software modules will now be described. In some embodiment of the present invention, console module is found on computer system 150 rather than computer system 180.

Console module 44. Console module 44 provides a view of server process module 38 through which a system administrator can monitor activity and execute system commands. In some embodiments of the present invention, console module 44 provides the following display panels: (i) a system status panel, (ii) a system message panel, (iii) an inspect system events panel, (iv) an inspect study status panel, (v) an inspect/change properties panel, and (vi) a tools menu.

(i) System status panel. The system status panel provides both graphic—and text-based summaries of O/C clinical module 12, RDE product 68, and server process module 38. For each software module monitored, pertinent information is provided. If the status of any of the monitored software modules changes, the system status panel is updated.

(ii) System message panel. The system messages panel provides a view of the system status that is more detailed than the view disclosed by the system status panel. In addition, text-based output from server process module 38 is displayed by the system message panel.

(iii) Inspect system events panel. The inspect system events panel provides a graph and a table that disclose a picture of server process module 38 activity. The graph shows the activity from the most recent 10 processing cycles. The graph is intended to provide a quick summary of current activity. Typically, the graph will show how many studies, sites, and patients are processed by server process module 38. The x-axis shows the process ID. The y-axis shows the count of how many of each type were processed. The table provides a view of the most recent actions and events that have occurred. Each row of the table displays the time, the process ID, the event code and the event description. Double-clicking on a table row provides a complete view of the event record.

(iv) Inspect study status panel. The inspect study status panel provides a view of data so that the system administrator is able to determine how many patients have been processed for a given front-end site 104. After selection of a clinical study associated with a front-end study definition 70 as well as a front-end site 104, the set of patients for that front-end site 104 is displayed. The list of patients confirms the enrollment for a front-end site 104. The list of patients also displays the corresponding patient numbers in the O/C database 10 and database 72. This allows the system administrator to compare the same patient on the two systems to verify that all information has been transferred correctly.

(v) Inspect/change properties panel. The inspect/change properties panel provides the system administrator with the ability to inspect and change the properties used by server process module 38. In some embodiments of the present invention, access privileges are enforced for this panel. That is, a user must have write access privileges in order to make any changes to the inspect/change properties panel.

(vi) Tools menu. The tools menu is used to send commands to server process module 38. These are high level commands such as Start/Stop/Enable/Disable. Each command is described in Table 5. In some embodiments of the present invention, only users who have write access are able to use the tools menu. Users with read access are not provided with the tools menu and cannot use it.

TABLE 5

Summary of the console module 44 tools menu

| | |
|---|---|
| Show sub-menu | Contains commands to show status information |
| Show Version | Shows server process module 38 version information. |
| Show Configuration | Shows server process module 38 configuration settings. |
| Show Timer | Shows length of various timing cycles used by server process module 38. |
| Show Status Account | Shows status of studies and sites being processed by each instance of server process module 38. |
| Show Uptime | Shows elapsed time since computer 150 was started. |
| Front-end study definition 70 sub-menu | Contains commands to change front-end study definition 70 processing. |
| Enable Study | Enables a study in status account book 114. |
| Disable Study | Disables a study in the status account book 114. |
| Audit Study | Compares a back-end clinical definition 8 with the front-end study definition 70 and conversion map 32 to see if there are any discrepancies. The result is stored in the persistent state record (110) of database module 48. |
| Add Study | Adds a study to the status account book 114. |
| Front-end site 104 sub-menu | Contains commands that operate on the status account book 114. |
| Enable front-end site 104 | Enables a front-end site 104 for processing by server process module 38. The user enters both the front-end study definition 70 and the name of front-end site 104. |
| Disable front-end site 104 | Disables a front-end site 104 so that processing of data from the front-end site 104 no longer occurs. The user enters both the front-end study definition 70 and the name of front-end site 104. |
| Restart Exec | Directs server process module 38 to restart itself. Mapper server module 30 and data exchange module 42 are also restarted. |
| Reset front-end sites 104 | Operates on status account book 114 to change the processing status of all studies. |
| Computer 150 | Contains commands that affect computer 150 processing. |
| Update database module 48 | Instructs server process module 38 to save the current status account information to database module 48. |
| Resume Server | Instructs server process module 38 to resume processing of data, after it has been paused. |
| Pause Server | Instructs server process module 38 to temporarily suspend processing of data. |
| Shutdown Exec | Instructs Server module 38 to shut down. Daemon module 36 will always restart server process module 38, so this command has the same effect as a restart request. |

TABLE 5-continued

Summary of the console module 44 tools menu

| | |
|---|---|
| Process Patient Data | Server process module 38 is directed to start the next process cycle immediately. |
| O/C clinical module 12 | Contains commands for connecting to O/C clinical module 12. |
| Enable OC Server | This command causes server process module 38 to reconnect to O/C clinical module 12 and start sending data. If problems occur back-end computer 140 is disabled. |
| Disable OC Server | This command disconnects the server hosting server process module 38 from the server hosting O/C database 10. |
| RDE product 68 | Contains commands for connecting to front-end site 104. |
| Enable front-end site 104 | Tries to reconnect to front-end site 104 to start querying for data. If problems occur then front-end site 104 is disabled. |
| Disable front-end site 104 | This command disconnects the server hosting server process module 38 from front-end site 104. |

Mapper client module 6. Mapper client software module 6 is the remote user interface to mapper server module 30. It provides a user interface for creating or updating front-end study definitions 70 and their corresponding conversion maps 32. The intended user of mapper client module 6 is an electronic case report form designer or clinical programmer, a person who is involved in the design of a new clinical trial. After a clinical trial has started, mapper client module 6 may be used to update the appropriate front-end study definition 70. Mapper client module 6 provides the following functionalities: (i) loading a back-end clinical definition 8 or external file 9, (ii) generating a front-end study definition 70 based on the back-end clinical definition or external file 9, (iii) inspecting and comparing front-end study definitions 70 to back-end clinical definitions 8, and (iv) modifying electronic properties of front-end study definitions 70. These functionalities will now be described with reference to an exemplary system that uses Oracle Clinical (O/C) as the back-end CDMS and MACRO as the front-end RDE product.

Figure 3:
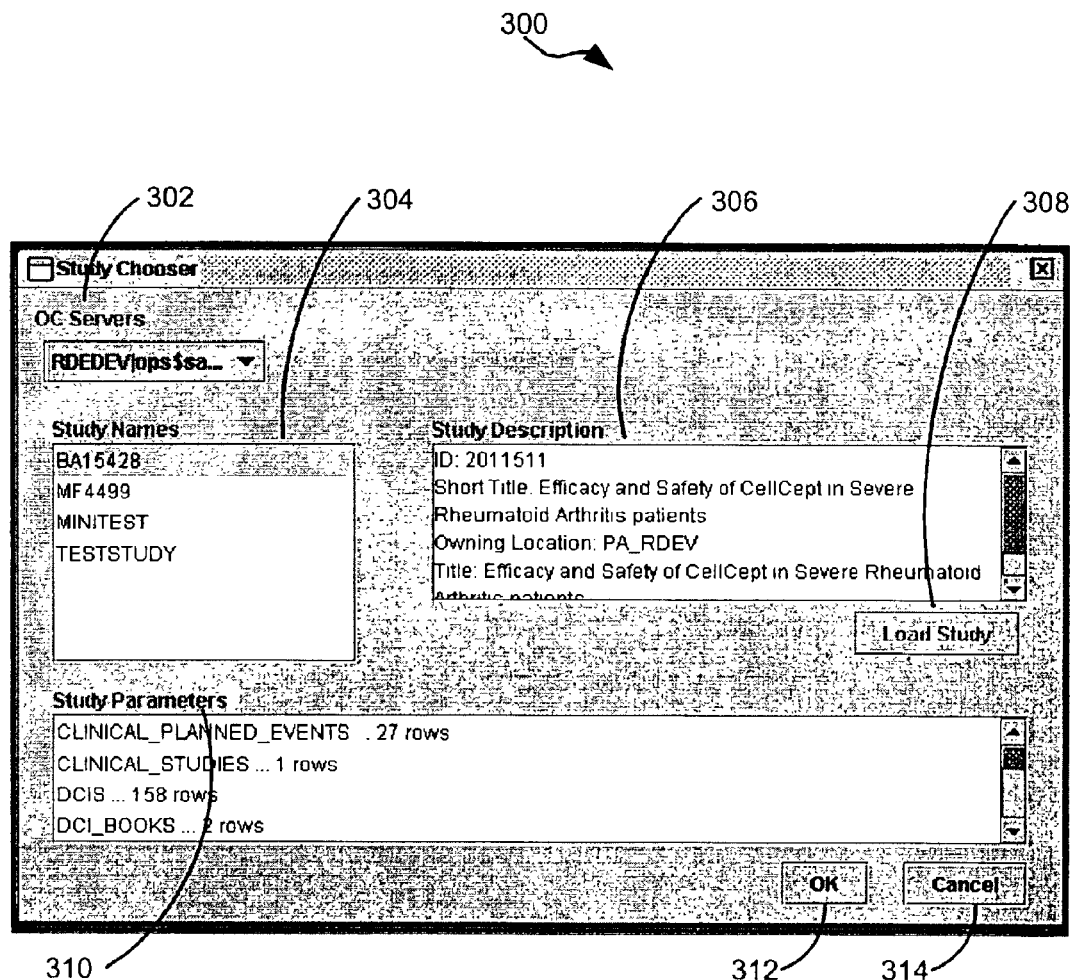
FIG. 3 is an illustration of the Study Chooser dialog used to select an Oracle Clinical definition, in accordance with one embodiment of the present invention.

(i) Loading a back-end clinical definition 8 or external file 9. A back-end clinical definition 8 defines a clinical study as a series of metadata tables within O/C database 10. In one embodiment of the present invention, mapper client module 6 provides the ability to load a back-end clinical definition 8 from an O/C database 10 using an interface such as panel 400 of FIG. 4. By clicking on the "Read From DB" button 406 in panel 400 (FIG. 4), the user is provided with a study chooser dialog window 300 of FIG. 3. Table 6 explains the purpose of each of the user interface elements provided by study chooser dialog window 300.

TABLE 6

Description of the elements of study chooser dialog window 300

| Element | Type | Purpose |
|---|---|---|
| Back-end computer 140 selection list 302 | Drop-Down list | Display and select a list of back-end computers 140 that have back-end clinical definitions 8 in an O/C database 10 |
| Study names box 304 | List Box | Display and select a back-end clinical definition 8 from the back-end computer 140 designated by back-end computer 140 selection list 302 |
| Study description box 306 | Text Area | Display a description of a selected back-end clinical definition 8 |
| Load study button 308 | Button | Retrieve the back-end clinical definition 8 from the back-end computer 140 designated by back-end computer 140 selection list 302 |
| Study parameters box 310 | Text Area | Display the contents of the selected back-end clinical definition 8 |
| OK button 312 | Button | Select a back-end clinical definition 8 for further processing |
| Cancel button 314 | Button | Close study chooser dialog window 300 and discard the selected back-end clinical definition 8 |

In Study chooser dialog window 300 (FIG. 3), the user selects a server using the "OC Servers" back-end computer 140 selection list 302. Back-end computer 140 selection list 302 may point to any computer addressable within system 1300 (FIG. 1). However, back-end clinical definitions are only found on computers that host an O/C database 10. A list of servers displayed in back-end computer 140 selection list 302 from which a back-end clinical definition 8 may be selected is provided by any one of a number of methods. For instance, each back-end computer 140 in system 1300 (FIG. 1) could be registered in a registry in memory of 28 of computer 150. Study chooser dialog window 300 would then read this registry and display it as back-end computer 140 selection list 302. Once a server has been selected, the list of back-end clinical definitions 8 available in an O/C database 10 on the selected server is displayed in study names box 304.

Rather than loading a back-end clinical definition 8 from an O/C database 10, an external file 9 may be loaded by mapper client module 6 using the "Read from File" button 404 of panel 400. An external file 9 includes a complete description of a clinical study. When the user selects "Read from File" button 404, a panel similar to that of panel 300 is displayed. Such a panel is then used to select an external file 9 within system 1300 to load.

Figure 4:
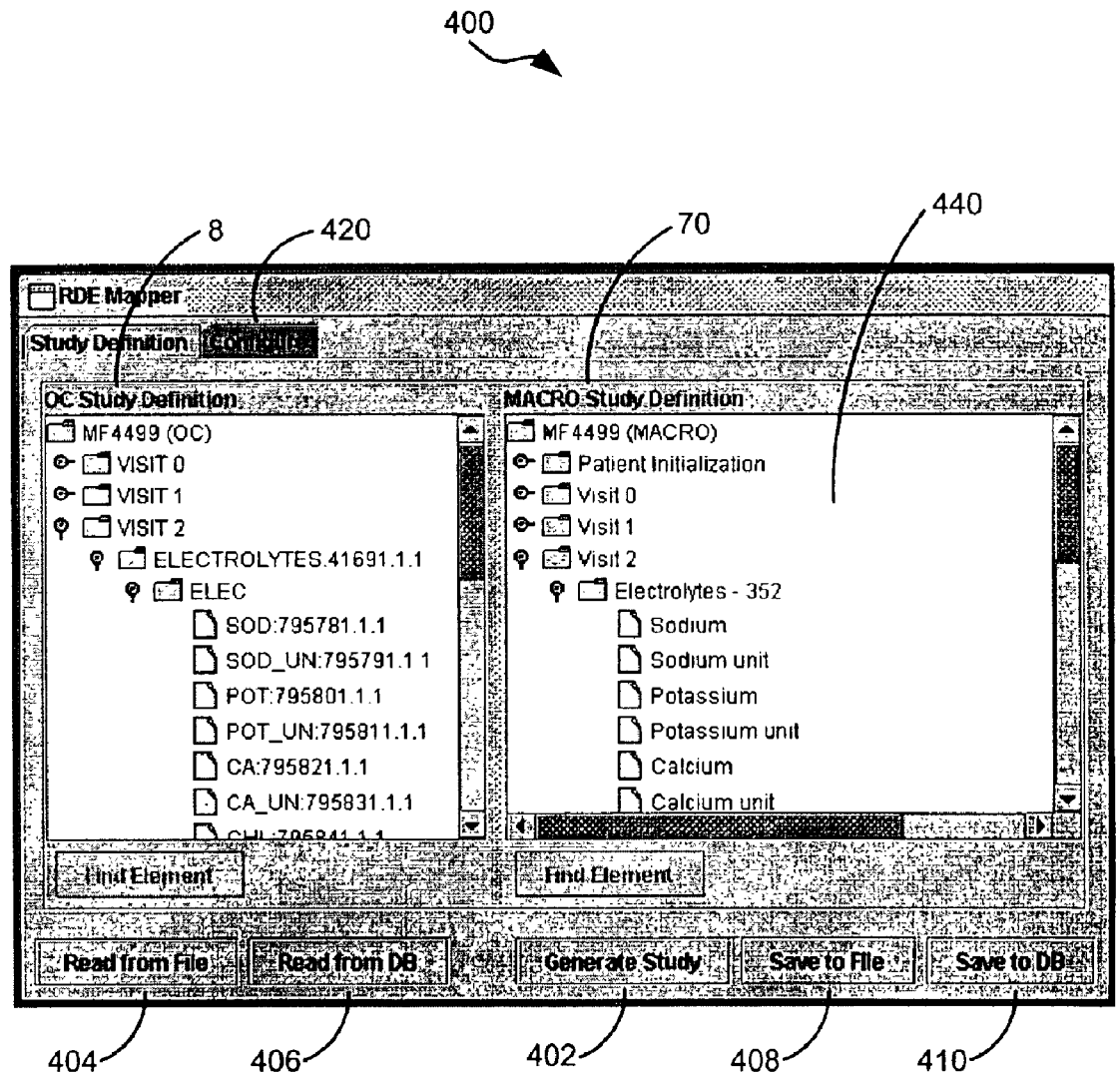
FIG. 4 is an illustration of a Study Definition Panel used to compare an Oracle Clinical definition to a macro study definition in accordance with one embodiment of the present invention.

(ii) Generate a front-end study definition 70. As described in more detail below, a front-end study definition 70, such as a macro study definition, defines a clinical study as a series of metadata tables. These metatables are optimized for Remote Data Entry. Once mapper client module 6 has loaded a back-end clinical definition 8 using panel 300 (FIG. 3) or an external file 9 using a window similar to that of panel 300, a corresponding front-end study definition 70 is generated using the "Generate Study" button 402 of panel 400 (FIG. 4). Once button 402 is pressed, a front-end study definition 70 that matches the loaded back-end clinical definition 8 is displayed in field 440 of panel 400.

In one embodiment of the present invention, when a user uses "Generate Study" button 402 to request that a front-end study definition 70 be generated, the current state of system 1300 is analyzed and the user is notified of the results. In particular, if the front-end study definition 70 or the corresponding conversion map 32 is not present in system 1300, the user is prompted to approve the creation of a new front-end study definition 70 and corresponding conversion map 32. If both a front-end study definition 70 and a conversion map 32 that correspond to the selected back-end clinical definition 8 are present in system 1300 and patient data has not been entered, then the user is prompted to approve the update of the existing front-end study definition 70 and the corresponding conversion map 32. If both the front-end study definition 70 and the corresponding conversion map 32 are present and patient data has been entered, then the user is notified that the current front-end study definition 70 and the conversion map 32 cannot be changed. The user is notified when mapper client module 6 has finished generating front-end study definition 70 and a conversion map 32 that correspond to the selected back-end clinical definition 8. A dialog window displays the results of the study definition process. If any problems occurred, warning or error messages are displayed in the dialog window.

(iii) Inspect and compare study definitions. Once study definitions are loaded and generated, panel 400 (FIG. 4) provides hierarchical tree viewers for simultaneously inspecting the contents of the back-end clinical definition 8 and the corresponding front-end study definition 70. For example, FIG. 4 illustrates the side-by-side placement of a selected Oracle Clinical definition and corresponding macro study definition to facilitate visual comparison. Table 7 explains the purpose of each of the user interface elements in accordance with one embodiment of the present invention.

TABLE 7

Explanation of panel 400 elements

| Element | Type | Purpose |
| --- | --- | --- |
| Back-end clinical definition 8 | Tree | Provides a visual display of the components of a back-end clinical definition 8, such as an Oracle Clinical definition. |
| Front-end study definition 70 | Tree | Provides a visual display of the components of a front-end study definition 70, such as a macro study definition. |
| Read from file button 404 | Button | Loads a back-end clinical definition 8 from a file. |
| Read from DB button 406 | Button | Loads a back-end clinical definition from O/C database 10 (FIG. 1). |
| Generate study button 402 | Button | Generates a front-end study definition 70 from a back-end clinical definition 8. |
| Save to file button 408 | Button | Saves a back-end clinical definition 8 to a file system. |
| Save to DB button 410 | Button | Saves a front-end study definition 70 to a front-end site 104 and saves a corresponding conversion map to a computer 150 (FIG. 1). |

When a user is inspecting a macro study definition using panel 400, the user is able to look at any macro electronic case report form page to determine if it was translated properly from the corresponding Oracle Clinical definition. For example, when the user right-clicks on an electronic case report form node of the macro study definition displayed in panel 400, a dialog window is created and a depiction of how the electronic case report form will be presented to a MACRO user is displayed in the newly created dialog window.

Figure 5:
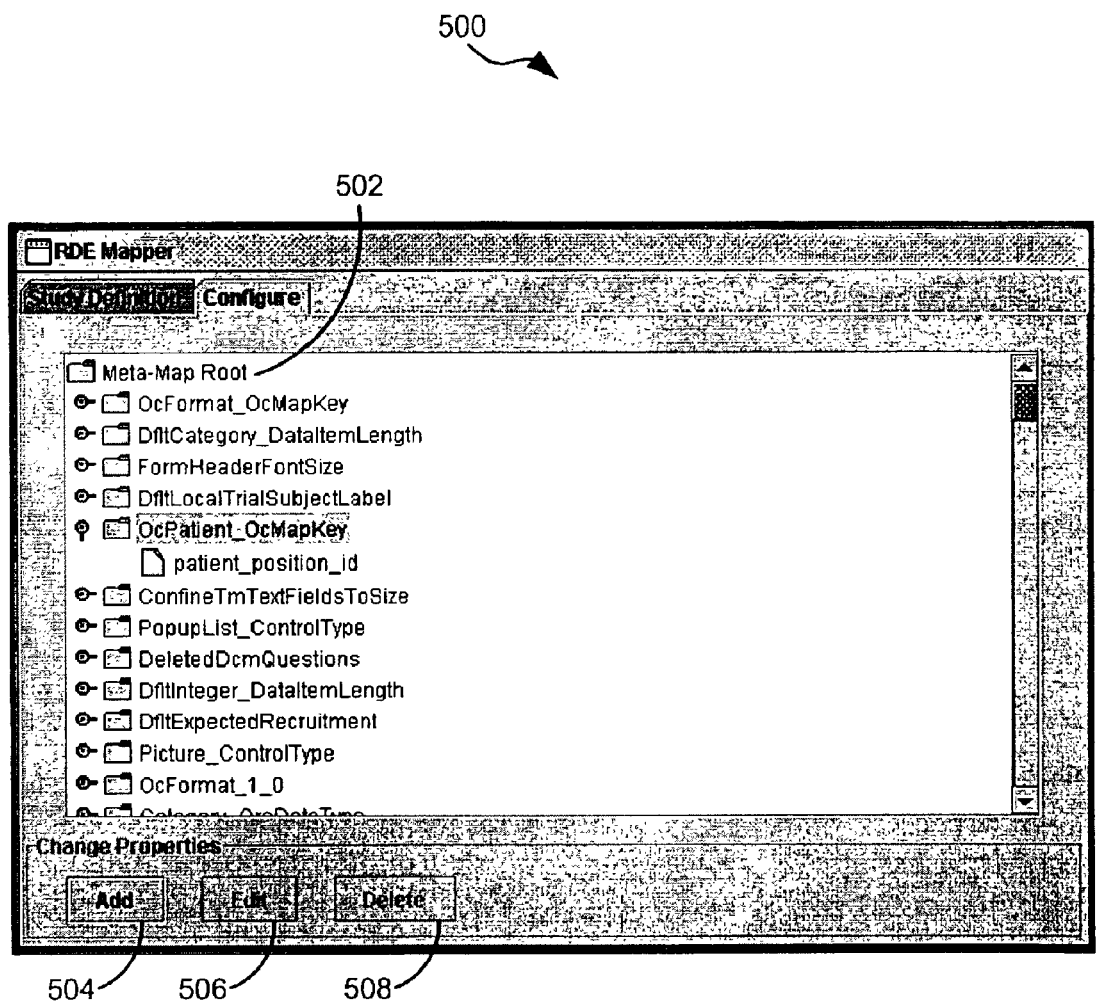
FIG. 5 is an illustration of a configuration tab panel used to edit the electronic appearance of a macro study definition electronic case report form.

(iv) Modifying electronic properties of front-end study definition 70. In FIG. 4, configure tab 420 provides a user interface containing properties that define the layout of an electronic case report form (eCRF). A set of forms is generated when a macro study definition is created/updated by RDE product 68 or by mapper server module 30. When a user selects configure tab 420 of FIG. 4, a configure tab panel 500 is displayed (FIG. 5). Configure tab panel 500 defines the electronic appearance and layout of a front-end study definition 70 electronic case report form. Using panel 500, the user is able to inspect and change the visual properties of the electronic case report form. Table 8 provides a description of the user interface elements for the configure tab panel 500.

In one embodiment of the present invention, properties in configure tab panel 500 are arranged as a hierarchical tree. The nodes displayed as folders are the property keys. Each property key node can be expanded to display one or more property value nodes. In preferred embodiments of the present invention, property key nodes cannot be changed. Within a property key node property, values can be added, edited or deleted. All values can be deleted from a property key, if desired.

TABLE 8

User Interface Elements of Configure Tab Panel 500

| Element | Type | Purpose |
| --- | --- | --- |
| Meta-Map Root 502 | Tree | Displays the contents of the macro study definition metamapper properties file. These properties are used to configure the appearance of the electronic case report form pages used by RDE product 68. Each tree node is a property key. Within each node are the property values for that key. |
| Add button 504 | Button | Adds a new value to a property key. Button 504 is only enabled when a property key node is highlighted. A dialog box is provided for data entry. |
| Edit button 506 | Button | Modifies the value of an existing property key. Button 506 is enabled only when a property value node is highlighted. A dialog box is provided for data entry. |
| Delete button 508 | Button | Removes an existing value of a property key. Button 508 is enabled only when a property value node is highlighted. |

7.2 ALTERNATE SYSTEM TOPOLOGY

Figure 2:
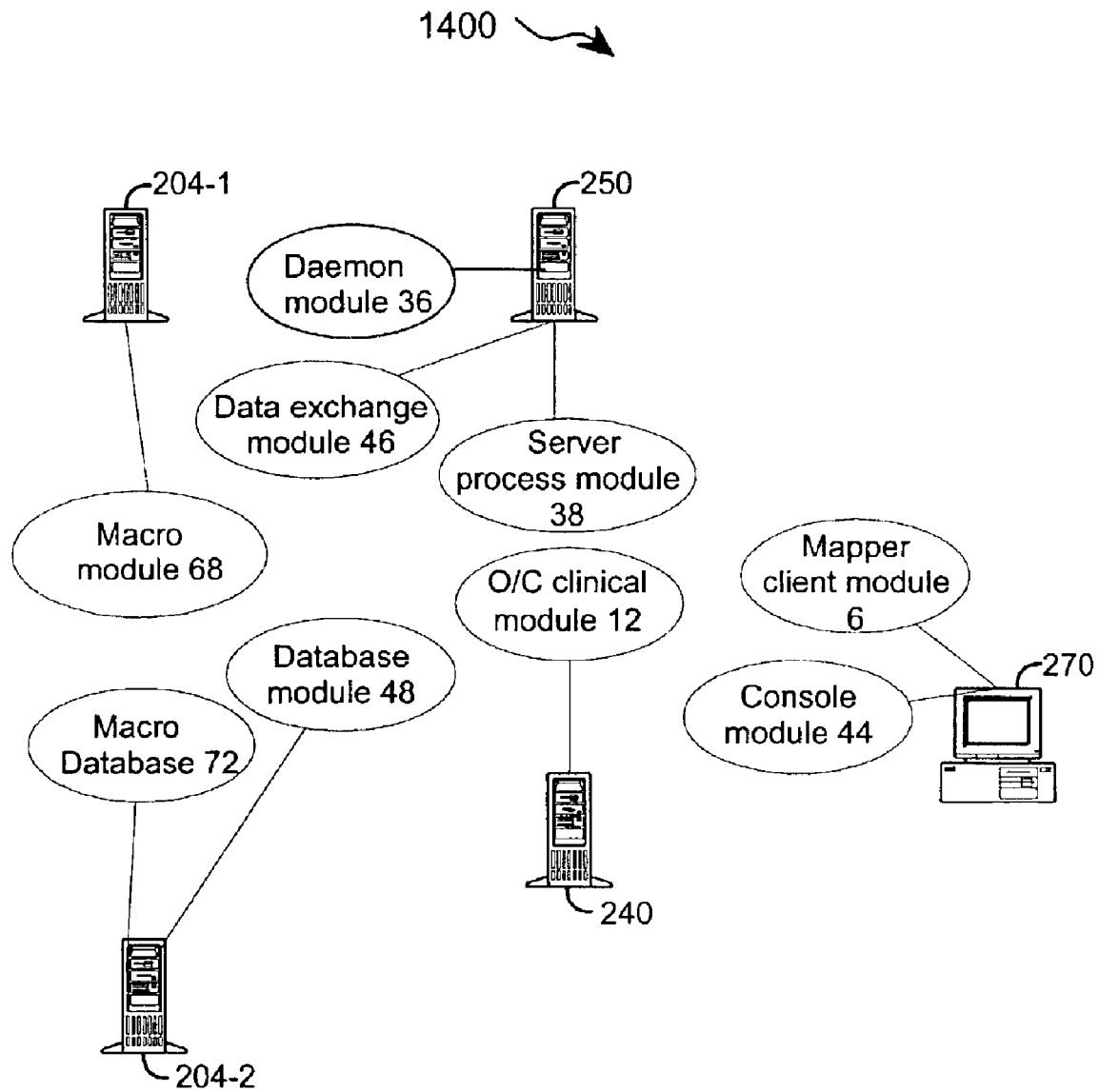
FIG. 2 is a deployment diagram showing components of a system in accordance with one embodiment of the present invention.

FIG. 2 illustrates the topology of an alternate system 1400 in accordance with the present invention. In system 1400, many of the software modules reside on computers different from the computers on which the corresponding software modules are found in system 1300. In system 1400, RDE product 68 is on server 204-1. Daemon module 36, data exchange module 42, and server process module 38 are on server 250. Database 72 and database module 48 are on server 204-2. O/C clinical module 12 is on server 240. Finally, mapper client module 6 and console module 44 are on separate computer 270. Although not shown, each computer in system 1400 is connected to the system by a transmission channel, which may be any wired or wireless transmission channel.

System 1400 illustrates the point that the instant invention provides ample flexibility such that any of the software modules, databases, or files used in the instant invention may reside on any computer within system 1300, system 1400, or a related system, as long as it is addressable within the system. As used herein, addressable means that the software modules, databases, or files residing on one computer in the system are accessible by another computer within the system. Such accessibility includes the ability to execute, query, read to or write from the software component, as warranted.

7.3 USE CASE SCENARIOS

The components of two exemplary systems in accordance with the present invention have been described in FIGS. 1 & 2. Attention now turns to three use case scenarios that illustrate many of the advantages of the present invention. In the first use case scenario, a back-end clinical definition 8 is converted to a front-end study definition 70 by mapper server module 30 (FIG. 1). In the second use case scenario, server process module 38 and/or data exchange module 42 obtains clinical data from front-end sites 104 and, using the appropriate conversion map 32 as a translation key, formats the clinical data in manner that can be stored by O/C clinical module 12 in database 10 in accordance with a back-end clinical definition 8. In the third use case scenario, data validation module 1208 (FIG. 12) detects a discrepancy and works with server process module 38 to send the discrepancy to the correct front-end site 104 for resolution.

7.3.1 USE CASE 1: CONVERTING A BACK-END CLINICAL DEFINITION INTO A FRONT-END STUDY DEFINITION.

Figure 6:
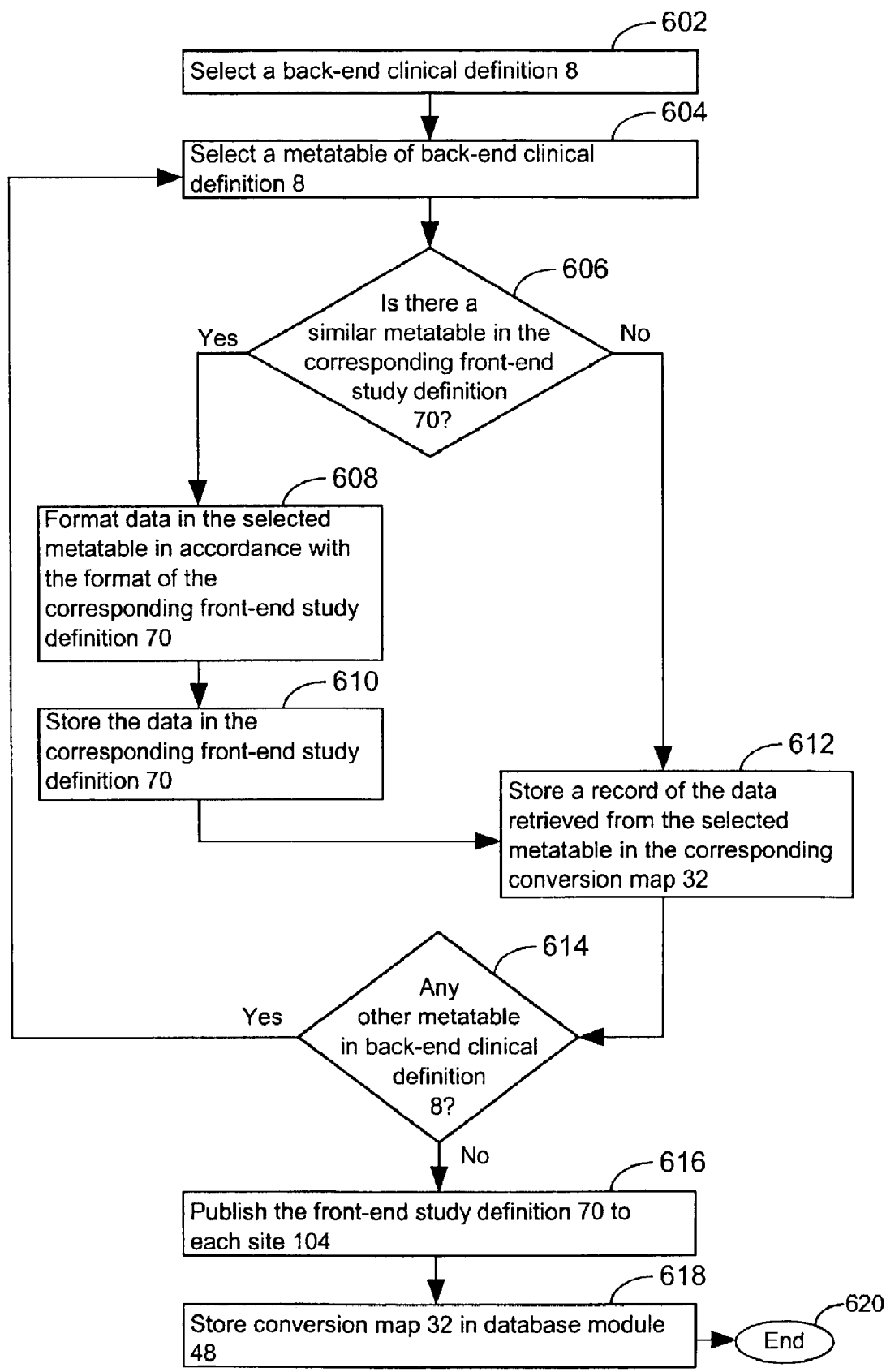
FIG. 6 illustrates processing steps in accordance with one embodiment of the present invention.

FIG. 6 depicts "Use Case 1," in which a back-end clinical definition 8 is converted to a corresponding front-end study definition 70. In processing step 602, a back-end clinical definition 8 is selected from O/C database 10. In one embodiment, the back-end clinical definition 8 is an Oracle Clinical definition that is selected and loaded from O/C database 10 using O/C clinical module 12. The methods of the present invention may be used to convert any back-end clinical definition into a front-end study definition. For example, the exemplary processing methods disclosed in FIG. 6 can be adapted for conversion of back-end clinical definitions created using Clintrial 4.3 (Clinsoft Corporation, Lexington, Mass.) or Oracle Clinical definitions (Oracle, Redwood Shores, Calif.).

In processing step 604, a metatable of the back-end clinical definition 8 is selected. For example, consider the case in which the back-end clinical definition 8 is an Oracle Clinical definition having metatables described in Table 3. The goal of the processing steps depicted in FIG. 6, then, is to use as much of the information provided in the metatables of the Oracle Clinical definition to construct metatables in a front-end study definition 70 so that RDE product 68 will query for clinical data with data entry forms that resemble data entry forms of the Oracle Clinical definition in accordance with a schedule that resembles the schedule used to present the forms of the Oracle Clinical definition. Thus, in the case where the back-end clinical definition 8 is an Oracle Clinical definition, processing step 604 may select a metatable of the Oracle Clinical definition such as CLINICAL_PLANNED_EVENT, CLINICAL_STUDY, DATA_COLLECTION_INSTRUMENT (DCI), and so forth. Generally speaking, processing steps 606 through 612 will then mine as much information out of the selected metatable to construct a front-end study definition 70 that adheres to the clinical protocol defined in the Oracle Clinical definition.

For each back-end clinical definition 8 selected in processing step 602, a corresponding front-end study definition 70 and conversion map 32 is created. The front-end study definition 70 includes a set of metatables, such as the metatables found in Table 2. The definition and format of the metatables in the front-end study definition 70 are determined by the specific RDE product 68 used by front-end site 104. Representative RDE products that may be used to create a front-end study definition 70 are provided by vendors such as Infermed, Ltd., (London, UK), Phase Forward Inc., (Waltham, Mass.), CB Technology, (Philadelphia, Pa.), TEAMworks, (Hannover, Germany), DataTRAK, (Cleveland, Ohio), and Araccel, (Stockholm Sweden). When the RDE product 68 is MACRO (Infermed, Ltd.), the front-end study definition 70 has the metatables defined in Table 2.

In processing step 606, a determination is made as to whether any of the metatables in the front-end study definition 70 could use information found in the metatable selected in processing step 604. If the information could be used (606-Yes), control passes to processing step 608. If the information could not possibly be used in the front-end study definition 70, (606-No), control passes to processing step 612.

In processing step 608, the data found in the metatable selected in processing step 604 is formatted in accordance with a format required by the corresponding front-end study definition 70. What follows are exemplary actions taken by processing step 608 in the case in which the back-end clinical definition 8 is an Oracle Clinical definition and the front-end study definition 70 is a macro study definition. When the metatable selected in processing step 604 is the CLINICAL_PLANNED_EVENT metatable in an Oracle Clinical definition (Table 3), processing step 608 extracts the name of the clinical trial from the CLINICAL_PLANNED_EVENT metatable and places the name of the clinical trial in the ClinicalTrial metatable of the macro study definition (Table 2). Similarly, clinical trial header information found in the CLINICAL_STUDY metatable of the Oracle Clinical definition (Table 3) is extracted and placed in the StudyDefinition metatable of the macro study definition (Table 2). A more complex case is presented when processing step 604 selects a DCI metatable of the Oracle Clinical definition (Table 3). The DCI metatable is a series of clinical questions presented to a data entrant on an electronic form. The metatable includes not only the questions, but their position on an 80×40 character based display. In this case, processing step 608 extracts the questions from the DCI and uses the extracted questions to construct a DataItem metatable in the macro study definition. In another example, Oracle Clinical definition metatables DISCRETE_VALUE and DISCRETE_VALUE_GROUPSs (Table 3) correspond roughly to macro study definition metatables ValueData (Table 2). Accordingly, the correspondence between Oracle Clinical DISCRETE_VALUE and DISCRETE_VALUE_GROUP metatables, and macro study definition ValueData metatables is used in processing step 608 to populate ValueData metatables in the macro study definition.

In processing step 610, the reformatted data generated during processing step 608 is stored in the appropriate metatable of the front-end study definition 70. Finally, a record of the data is stored in the corresponding conversion map 32 in processing step 612.

If there is no metatable in the front-end study definition 70 that could use data found in the metatable selected during processing step 604, (606-No), a record of the data in the metatable is stored in the corresponding conversion map 32 in processing step 612 or discarded. In one embodiment, the back-end study definition 70 defines the position of clinical questions on an 80×40 character-based display. For example, the back-end clinical definition may have VTI100 codes that designate where a question will appear on a text-based screen. Furthermore, the back-end clinical definition may designate graphic characters to be displayed on an 80×40 character-based legacy display during data entry. Such graphics may be characters for horizontal or vertical lines that are found in the VTI100 extended character set. In the case where the back-end clinical definition 8 is an Oracle Clinical definition, such graphics are stored in the DCM_LAYOUT_GRAPHIC metatable (Table 3). When processing step 604 selects a DCM_LAYOUT_GRAPHIC metatable, the condition 606-No is satisfied (FIG. 6) and, in fact, the contents of DCM_LAYOUT_GRAPHIC are ignored because the eCRF form of the macro study definition uses far more sophisticated graphics. Another example of a situation in which 606-No arises is in the case where an Oracle Clinical definition defines the number of times a question will be repeated. Macro study definitions do not have repeat question functionality, and thus cannot make use of the Oracle Clinical definition attribute.

After processing step 612 has been executed, a determination 614 is made as to whether there are any other metatables in back-end clinical definition 8 that have not been selected by an instance of processing step 604. If so (614-Yes), control returns to processing step 604 where a metatable of back-end clinical definition 8, which has not been selected by a previous instance of processing step 604, is selected. If there are no remaining metatables of back-end clinical definition 8 to process, (614-No), control passes to processing step 616 where the front-end study definition 70 is published on each front-end site 104 used to collect clinical data for the clinical study defined by the back-end clinical definition 8 selected in processing step 602. Then, in processing step 618, the conversion map 32, which is defined by the sequential execution of processing step 612 in the manner shown in FIG. 6, is stored in database module 48 on computer 150. In processing step 620 the process ends.

Reference will now be made to FIGS. 7 through 8B, which disclose selected data segments that are found in conversion maps 32 in embodiments of the invention in which the back-end clinical definition is an Oracle Clinical definition (Table 3) and the front-end study definition 70 is a macro study definition. A conversion map 32 is used during "Use Case 1", "Use Case 2", and "Use Case 3." In "Use Case 1," symbolic links are built for the components of front-end study definition 70 that are equivalent or analogous to the components of the corresponding back-end clinical definition 8. In "Use Case 2," where clinical data is collected from front-end sites 104, the conversion map 32 is used to store data about clinicians, clinical sites 104 enrolled in a clinical trial, and patient data. Then, the symbolic links created in processing step 612 of "Use Case 1" are used to construct a back-end data packet that has the clinician/clinical site 104/patient data obtained during "Use Case 2." The back-end data packet is then imported into O/C database 10. The data segments of conversion map 32 that are appended during "Use Case 2," (FIGS. 8C through 10) will be described in the section entitled "Use Case 2."

For each CLINICAL_PLANNED_EVENT metatable in an Oracle Clinical definition (Table 3), mapper server module 30 creates a corresponding StudyVisit metatable in the macro study definition (Table 2) and adds a record of this correspondence to segment 702 (FIG. 7A). In segment 702, the first column is a single-field look-up key to a component of an eCRF form found in a macro study definition. Column two in segment 702 is a single-field look-up key to a DCI metatable of the corresponding Oracle Clinical definition. Column 3 in segment 702 is the reference identifier for a DCM metatable (Table 3) in the Oracle Clinical definition. Like columns 2, and 3, columns 4–6 identify various components of an Oracle Clinical definition.

Now that the data structure of segment 702 has been defined, the advantages of segment 702 may be described. Referring to the first data row of segment 702, when server process module 38 receives code 365, it knows that an entry has been made to component 365 of an eCRF associated with the front-end study definition. The entry to component 365 of an eCRF could be, for example, the name of a patient. Furthermore, because of the symbolic information found in segment 702, server process module 38 knows that the response to component 365 of the macro eCRF form should be entered into the DCI metatable 17036 of the corresponding back-end Oracle Clinical definition.

As noted in Table 3, an Oracle Clinical definition includes one or more data collection instruments (DCIs). When a DCI metatable is selected in processing step 604, mapper server module 30 places components of the DCI into two segments of conversion map 32, an OcDci segment (FIG. 7B, element 704) and an OcDciMod segment (FIG. 7C, element 706). The OcDci and OcDciMod segments serve the function of collecting information that correlates a DCI metatable (Table 3) of an Oracle Clinical definition with corresponding elements in an eCRF form within a macro study definition. Thus, the first column in segment 704 contains two numbers separated by a period delimiter. The first number represents a particular eCRF form within the macro study definition. The second number represents a particular component, such as a clinical question, in the designated eCRF form. While the first column of segment 704 (FIG. 7B) references a component of the macro study definition, remaining columns in segment 704 reference various aspects associated with a DCI metatable of an Oracle Clinical definition.

Now that the structure of segment 704 has been disclosed, an example of how the segment is used by server process module 38 can be described. When server process module 38 receives data associated with tmMapKey 316.365, it knows that the data is a clinical response to component 365 of eCRF form 316. The exact nature of the data associated with tmMapKey 316.365 is dependent upon the nature of component 316.365 of the macro study definition. For example, component 316.365 could be the question "Gender?" on eCRF form 316 and the data associated with tmMapKey 316.365 could therefore be the answer to this question, i.e. "Male" or "Female." When server process module 38 (FIG. 1) receives the data associated with tmMapKey 316.365, it performs a table lookup in segment 704 and knows that the data associated with tmMapKey 316.365 should be routed to the DCI metatable 35736 of the corresponding Oracle Clinical definition.

In FIG. 7C, exemplary OcDciMod segment 706 is listed with each row converted to a column for clarity. Thus, the first column represents the names of the elements within segment 706 whereas columns 2 and 3 represent two rows of data from a conversion map 32 used in an actual clinical study. OcDciMod segment 706 maps groups of questions found on an eCRF page-in a macro study definition to groups of questions found in an Oracle Clinical definition. For example, the first column of data in segment 706 (FIG. 7C) references the group of questions "317.null." That is, the TmMapKey identifier references any question in the 317 group, such as 317.1 (question 1), 317.2 (question 2), and so forth. Next, segment 706 states that the group of question having the TmMapKey 317 in the macro study definition is equivalent to the DCM (Table 3) having an id of 32936.

Thus, whenever server process module 38 receives data associated with a TmMapKey identifier 317.null, it knows that the data is associated with a group of questions within the macro study definition 317 and that the responses to these questions will need to be placed in the DCM group 32936.

Taken together, segments 704 and 706 show one advantage of the present invention. By independently storing a symbolic link that traces the relationship of an individual clinical question in a back-end clinical definition 8 to a front-end study 70, the question can be modified at a later date without editing the group in which the question belongs.

The DCM metatables of an Oracle Clinical definition (Table 3) are stored in the OcQuestion segment 802 (FIG. 8A) of conversion map 32. As noted above, an Oracle Clinical DCM metatable includes a group of data collection instruments (DCIs), such as clinical questions.

Questions from an Oracle Clinical DCM have attributes that are not found in corresponding macro study definition metatables. For example, a DCM may have attributes that indicate that a clinical question be repeatedly asked until the user no longer provides information. An example of the use of this "repeat" attribute is the case in which the prompt "Please list another medication that is being taken by the patient" is repeated until the data entrant no longer provides another medication taken by the patient. While Oracle Clinical definitions have the "repeat" attribute, macro study definitions do not. Consequently, the "repeat" attribute found in the back-end clinical definition is stored in segment 804 (FIG. 8B). Segment 804 also stores questions or attributes from front-end study definition 70 that are wholly derived from other front-end metatables and therefore do not correspond to back-end metatables.

Laboratory ranges. In some embodiments of the present invention, discrepancies, lab values, coded values, and ranges are translated from a back-end clinical definition 8 to a front-end study definition 70, in addition to the metatable data described above. Such information includes code values for sites and corresponding investigators as well as patients that are participating in a clinical trial. Ranges includes laboratory normal ranges (e.g., upper and lower limits on serum hemoglobin concentration for healthy men and women). In such embodiments, the results of the process described in FIG. 6 is the creation of a front-end study definition 70 that includes question attributes, form layout, form order, and visit scheduling that is defined by a back-end clinical definition 8.

Thesaurus loaded questions. In some embodiments, the generated front-end study definition 70 will include, as not enterable, questions designated as thesaurus-coded questions. In one embodiment, the back-end clinical definition 8 will indicate that a question is a thesaurus-coded question by assigning to it a zero-length discrete value group (e.g., a code list). The corresponding question in the front-end study definition will not be enterable by a clinician.

Centrally loaded question. In some embodiments, the generated front-end study definition 70 will include, as not enterable, questions, question groups, and data collection modules designated as centrally loaded questions. For example, laboratory questions may be designated as centrally loaded questions in the back-end clinical definition 8. Then, in the corresponding front-end study definition 70, the question will be designated as not enterable.

Form format. In some embodiments of the present invention, forms in the front-end study definition 70 will be formatted in a manner that duplicates the layout defined for data-entry screens in back-end clinical definition 8, within the spatial limits imposed RDE product 68 (FIG. 1).

Updating a front-end study definition 70 based on a back-end clinical definition 8. In some embodiments of the present invention, a front-end study definition 8 can be updated based on modification made to a back-end clinical definition. Such updates can be performed either before or after a clinical study has been initiated using the front-end study definition 8. Typically, such updates are in the form of additions. In one example, additions are made to the back-end clinical definition 8 and the additions are propagated to each corresponding front-end study definition 70 using methods such as those disclosed in FIG. 6. When updating a front-end study definition, restriction imposed by O/C clinical module 12 and RDE product 68 on updates to deployed studies are not violated. Furthermore, when allowed by RDE product 68 and O/C clinical module 12, the methods of the present invention can be used to implement question-modification changes, including field-length changes, code-list changes, and data type changes.

Performing study audits. In some embodiments of the present invention, automatic audits of corresponding back-end clinical definitions 8 and front-end study definitions 70 are performed to detect incompatibilities that would prevent successful translation and transferal of any user responses to study questions. In one embodiment, derived questions, questions and forms may be added to front-end study definition 70 and designated as nonclinical. Responses to the derived questions, questions, and forms that are designated as nonclinical are not transferred to the CDMS because the corresponding back-end clinical definition 8 does not include derived questions, questions and forms that are designated as nonclinical. Rather, the answers to these derived questions are audited using, for example, database module 48 and audit trail 112.

7.3.2 USE CASE 2: RETRIEVAL OF CLINICAL DATA FROM REMOTE DATA ENTRY PRODUCTS AND IMPORT OF THIS DATA INTO A LEGACY BACK-END CLINICAL DATA MANAGEMENT SYSTEM.

FIG. 11 depicts exemplary processing steps that collect clinical data from front-end sites 104 and translate it into a form that can be read by O/C clinical module 12. FIG. 11 is best understood in conjunction with exemplary system 1300 of FIG. 1. In processing step 1102, server process module 38 is started and configuration file 40 is opened. Configuration file 40 includes a list of the names of clinical trials that are being tracked by system 1300 (FIG. 1). Configuration file 40 further includes a list of front-end sites 104 that are collecting data for each of the clinical trials listed in configuration file 40.

In processing step 1104, the name of one of the clinical trials 1104 tracked by system 1300 is retrieved from configuration file 40. Then, in processing step 1106, one of the front-end sites 104 presently collecting data for the clinical trial, "active clinical trial X," is obtained. In processing step 1108, the identity of "active clinical trial X" and the front-end site 104 is used to poll a time stamp 76 that corresponds to front-end site 104 in the status account book 114 of persistent state record 110 (FIG. 1). In principle, there exists a stamp 76 that corresponds to each clinical trial that is being conducted at a front-end site 104 in system 1300. The time stamp 76 represents the date and time at which a query for clinical data from front-end site 104 was last made by server process module 38. After a front-end site 104 has been queried for clinical data, the corresponding time stamp 76 is set to the current date and time.

In processing step 1120, database 72 of front-end site 104 is polled to determine whether any clinical data has been acquired since the time stamp 76, corresponding to the clinical trial retrieved in processing step 1104, was last set. If data has been acquired at front-end site 104 since time stamp 76 was set (1120-Yes), then processing steps 1122 through 1141 are performed. If data has not been acquired since time stamp 76 was set (1120-No), control passes to processing step 1142 where configuration file 40 is checked to determine whether there exists any additional front-end sites 104 within system 1300 that are collecting data for the "active clinical trial X" retrieved in processing step 1104.

When new data is available in database 72 at front-end site 104 (1120-Yes), the data is packaged into a front-end data packet and sent to the server hosting server process module 38 (processing step 1122). The front-end data packet is formatted in accordance with the particular front-end study definition 70 that is associated with the "active clinical trial X" retrieved in processing step 1104.

In processing step 1124, the front-end data packet retrieved in processing step 1122 is parsed by obtaining the name of a new patient in the front-end data packet. As used herein, a new patient is defined as one that has not been mapped in the conversion map 32, corresponding to a given front-end study definition 70, to the O/C identifiers 3 (FIG. 1), describing a corresponding O/C site, O/C investigator, and O/C patient code.

In processing step 1126, server process module 38 looks for responses in the front-end data packet to special questions set up in the required identifier form of the front-end study definition 70. In processing step 1130, if these O/C identifier questions are properly filled in the front-end data packet (1126-Yes), then server process module 38 adds the new patient to the conversion map 32 that corresponds to "active clinical study X" and the front-end study definition 70. It will be appreciated that the new patient is added to the conversion map 32 in such a manner that the patient can be tracked in either the front-end study definition 70 or the corresponding back-end clinical definition 8.

When any new patient lacks one or more of the requisite front-end site 104, investigator or patient code designations required by O/C identifiers 3 (1126-No), server process module 38 notes the error and notifies the operator of front-end site 104 in processing step 1128. Furthermore, all clinical data from that front-end site 104 is postponed until appropriate O/C identifiers 3 have been entered for all patients. In other embodiments of the present invention, the new patient data is rejected in processing step 1128. A query is then made for additional new patients in the front-end data packet. When additional patients exist in the front-end data packet (1140-Yes), processing step 1124 is repeated.

When there are no additional patients in the front-end data packet (1140-No), the conversion map 32 corresponding to the clinical trial is used to construct a back-end data packet, one data record at a time in processing step 1141. The resulting O/C sequence of responses may differ in length from the corresponding sequence stored in database 72. For example, in one embodiment of the present invention, repeat defaults in Oracle Clinical definitions are not even questions in macro study definitions, so server process module 38 creates an Oracle Clinical definition defaulted response where no such audit-trail record exists in the corresponding macro study definition. As another example, certain required-identifier questions are special questions created by exemplary server process module 38 for the macro study definition during "Use Case 1." Therefore, they do not exist in Oracle Clinical definitions. For any response to such questions, there will not be corresponding rows in the back-end data packet. However, in a preferred embodiment of the present invention, all responses provided by RDE product 68 appear in the same order in the back-end data packet. Once the back-end data packet has been generated, it is uploaded into O/C database 10 using O/C data capture API 14.

After processing step 1141, control passes to processing step 1142 where configuration file 40 is checked to determine whether there exists any additional front-end sites 104 within system 1300 that are collecting data for the "active clinical trial X" retrieved in processing step 1104. If there are additional front-end sites 104 that are collecting clinical data for "active clinical trial X" (1142-Yes), control returns to processing step 1106, where a different front-end site 104 that is collecting data for "active clinical trial X" is selected. If configuration file 40 reveals that there are no additional front-end sites 104 presently collecting clinical data for "active clinical trial X" (1142-No), then control passes to processing step 1152.

In processing step 1152, a query of configuration file 40 is made to determine whether there are any additional clinical trials presently being tracked by system 1300. If there are (1152-Yes), control returns to processing step 1104, where a different active "clinical trial X" is retrieved from configuration file 40, and processing steps 1108 through 1152 are repeated accordingly. The process ends (1170) if there are no additional clinical trials presently being tracked by system 1300 (1152-No).

In typical embodiments, the exemplary processing steps shown in FIG. 11 are performed in accordance with a schedule. For example, in one embodiment, processing step 1102 is initiated on a daily basis using an automated scheduler.

Now that the processing steps in FIG. 11 have been disclosed, segments of conversion map 32 updated during "Use Case 2" may be described. Generally speaking segment 806 (FIG. 8C) maps clinical sites from the front-end study definition to the corresponding back-end clinical definition, segment 9A (FIG. 9A) maps the identity of investigators collecting clinical data from the front-end study definition to the back-end clinical definition, and segment 904 (FIG. 9B) maps actual patients from the front-end study definition to the back-end clinical definition.

Segment 806 (FIG. 8C) depicts an OcSite segment 806 that is found within some exemplary conversion maps 32. The segment 806 collects information from front-end sites 104. In column 1 of segment 806, the tmMapKey refers to patients enrolled in front-end site "rp101621." Accordingly, the first data row in segment 806 references patient number 1 at front-end site 104 "rp101621," the second row refers to patient 2 at site "rp101621," and the third row references patient 3 at site "rp101621." Columns 2 through 7 list the corresponding Oracle Clinical definition identifier information for the site information found in column 1. Segment 806 is used to route any information associated with a given front-end site 104 to the unique components of the back-end clinical definition that are reserved for that site.

Segment 902 (FIG. 9A) tracks the names of investigators that are collecting data for each patient at front-end sites 104. Column 1 references the site and patient id. For example, in the first data row of segment 902, patient 1 at site "rp101621" is listed. Column 3 discloses the id of the investigator that is collecting data for the patient. Column 2 discloses the Oracle Clinical id of the investigator that is collecting data for the patient disclosed in column 1. Segment 806 is used to route any information associated with a given clinical investigator at a front-end site 104 to the unique components of the back-end clinical definition that are reserved for that clinical investigator.

Segment 904 (FIG. 9B) depicts an exemplary OcPatient segment 904 that is found within some conversion maps 32 in accordance with the present invention. Segment 904 of conversion maps 32 collects patient identifier information available from the front-end study definition 70 required identifiers form, which mapper server module 30 creates for the front-end study definition 70. Segment 806 is used to route any information associated with a given patient at a front-end site 104 to the unique components of the back-end clinical definition that are reserved for that patient.

Segment 906 (FIG. 9C) depicts an exemplary OcKey segment 906 that is found within some conversion maps 32. The OcKey records one-to-one correlations between some metatables of an Oracle Clinical definition and corresponding metatables of the macro study definition that were generated in the processing steps of "Use Case 1." Such correlations include correspondences between DISCRETE VALUE metatables of an Oracle Clinical definition (Table 3) and corresponding ValueData metatables of the macro study definition (Table 2).

Segment 1002 (FIG. 10) depicts an exemplary Special-Values segment 1002 that is found within some conversion maps 32. In particular, segment 1002 shows the values used in a representative clinical trial. The SpecialValues segment records identifies the data items that provide information that data exchange module 42 must use to correlate a front-end site 104 and patient identifiers with O/C clinical module 12, investigator and patient identifiers. Column 2 of segment 1002 provides visit identifiers and data item identifiers for front-end study definition 70.

Error Handling. Because server process module 38 interacts with a number of different modules that are potentially distributed across several different servers and desktop computers throughout system 1300 (FIG. 1), a preferred embodiment of server process module 38 includes a robust error handling feature set. The following is a set of representative error handling features provided in some embodiments of the present invention.

Broken connection/loss of system service: Connection problems to either RDE product 68 via data exchange module 42 or O/C clinical module 12 result in server process module 38 informing the administrator user by E-mail, then retrying the connection until it is restored.

Data errors—disabled sites: In some embodiments of the present invention, when an error is detected with the data retrieved from RDE product 68 (FIG. 11, processing step 1122) or during loading of that data into O/C database 10 (FIG. 11, processing step 1141) the front-end site 104 from which the data came will be marked as "bad" causing further loads of data from that front-end site 104 to be disabled until the problem is corrected. Once the problem is resolved, the front-end site 104 is reenabled using the console module 44 and processing is enabled for front-end site 104.

Front-end sites 104 postponed for incomplete O/C identifiers: For any translation or data-loading error, server process module 38 marks the originating front-end site 104 as problematic in some embodiments of the present invention. Once marked as problematic, exemplary server process module 38 will not translate or load data from the front-end site 104 until the problem is rectified. In cases of translation or loading error, the fix will depend on the administrator. Once exemplary server process module 38 finds O/C identifiers 3 to fix the original patient-mapping problem, module 38 requests all data from RDE product 68 resident on front-end site 104 since before the original problem arose. Accordingly, in one embodiment of the present invention, status account book 114 in database module 48 keeps two time stamps per site: one for the last successfully loaded macro response, and one for the most recent time stamp for the front-end site 104 at which time O/C identifiers 3 were still missing for a patient. In some embodiments, data from a front-end site is not postponed when there is a problem with data from an individual patient. Rather, server process module 38 refuses to process data for that patient until the problem with the patient data is resolved.

Internal errors: Exemplary server process module 38 records a persistent log of all events that occur in persistent state record 110 (FIG. 1). Events considered as fatal errors, such as those that cause system malfunction, are trapped where possible and cause an alarm E-mail to be sent to the administration user.

Incremental transfer of response data: In some embodiments of the present invention, database module 48 will maintain status account information for clinical data, tracking what data and discrepancies are new. Further, status-account information will be maintained on a per-patient basis for each patient in a clinical trial. In one embodiment of the present invention, the audit trail for RDE product 68 will be polled for visit-date changes and will apply these visit-date changes to applicable data collection instruments and data collection modules in the corresponding back-end clinical definition 8.

Transfer of laboratory data and coded thesaurus terms: In some embodiments of the present invention, laboratory data and coded thesaurus terms are translated from O/C database 10 to RDE product 68. Laboratory data is typically obtained in a manner that is independent of front-end sites 104. For example, in some embodiments, laboratory results are loaded into O/C database 10 from a laboratory using a generic loader 1204. In one embodiment, data that is designated laboratory data or as a code thesaurus term is not reloaded from the front-end 104 to O/C database 10.

7.3.3 DATA PACKETS FORMATTED IN A FRONT-END AND BACK-END INDEPENDENT FORMAT IN ACCORDANCE WITH ONE EMBODIMENT OF THE PRESENT INVENTION.

1. Introduction. The present invention provides a novel form of packet structure that is used to exchange data between RDE product 68 and O/C database 10 using conversion map 32 in accordance with one embodiment of the present invention (FIG. 1). In one embodiment, back-end clinical definition 8 is an Oracle clinical definition and front-end study definition 70 is a macro study definition. However, those of skill in the art will appreciate that the packets of the present invention may be used for types of back-end clinical definitions 8 other than the Oracle clinical definition as well as for types of front-end study definitions other than a Macro study definition. Such packets would be similar to those disclosed herein.

The data packets are suitable for system 1300 where data exchange that is insulated from the data structure requirements of a back-end CDMS and a front-end RDE is desired.

An exemplary case is the situation in which the back-end CDMS uses a clinical definition 8 that is an Oracle clinical definition and the front-end RDE uses a study definition 70 that is a macro study definition. Clinical definition 8 and study definition 70 are not identical in format although they encompass the same clinical trial data. The data packets of the present invention can be used to exchange data between these two formats.

Data packets in accordance with one embodiment of the present invention provide a generic "packet" data structure that encapsulates data that is in either Oracle Clinical or MACRO format. In one embodiment of the present invention, back-end packets and front-end packets described in "Use Case 1" and "Use Case 2" have a similar data structure. In addition to site, clinician, and patient data, such packets include support for collections of data that are used for accounting purposes and for the mapping relationship between the front-end study definition 70 and the corresponding back-end clinical definition 8.

The advantage of using a "packet" that is formatted in a back-end and front-end independent data structure is that code mechanisms that handle the packets at a generic level can be re-used rather than having to code for each specific back-end or front-end product. For example, in one embodiment, the packets of the instant invention provide a mechanism that allows for storage of any "packet" in a persistent data store.

Another advantage of data packets in accordance with this embodiment of the present invention is that the contents of the packet are easily modified without having to re-compile source code because the packet definition is held in a file that is independent of the front-end or back-end. This definition in itself is useful as it allows for standardization of the contents of a packet as well as the management of different versions of the system.

2. General packet data structure. The data structure of a packet in accordance with one embodiment of the present invention is illustrated in FIG. 14. Packet 1400, which is formatted in a back-end or front-end independent data structure, has the following basic structure:

A single packet header 1402 followed by one or more data segments 1408

Each data segment 1408 has a single data segment header 1410 describing the data layout (i) Packet header 1402. The packet header portion of the packet allows for the recordation of the type of data contained in the packet (e.g., data type 1404) along with audit trail information 1406, such as the system version and who created or modified the packet. The header values are stored as a series of properties so that they can be extended without the need to recompile the existing code base. An exemplary header 1402 from a Study Mapping Relationship Packet (StudyMap) is provided in Table 9.

TABLE 9

Exemplary header for packets in accordance with one embodiment of the invention

%% com.roche.rde.wip.metamapper.StudyMap: {build.number=0, StudyName=RS1,CreatedBy=SAYERR, GgbVersion=1.1, OcStudyVersion=2001-03-26, StudyVersion=1, CreatedDate=2001-05-25@13:17:15, ModifiedBy=SAYERR, ModifiedDate=2001-05-25@13:16:51, OcSystemVersion=3.1.1}

The first part of the header line indicates the name of the packet, in this case "com.roche.rdc.wip.metamapper-.StudyMap." The next part of the header line is a bracketed block that can hold any number of key and value pairs. For example, in the line shown the first key "build.number" has a value of 0. The next key, "StudyName", has the value "RS1" and so on.

(ii) Data segment header 1410. Each data segment 1408 includes a data segment header 1410. The data segment header 1410 describes the layout of the data found in the following rows of the associated data segment 1408. The data segment header 1410 also indicates how many data rows are to be found in the data segment body 1412. Use of this value ensures that the data contained in the packet is intact. An example header for the "DataItemResponse" segment from a Macro Patient Data Response Packet (TMDataPacket) is disclosed in Table 10.

TABLE 10

Exemplary Data Segment Header 1410

%% DataItemResponse
%% 38 records
%% ClinicalTrialId          LockStatus
   TrialSite                Reviewstatus
   PersonId                 SDVStatus
   ResponseTaskId           ImportTimeStamp
   VisitId                  ValidationId
   CRFPageId                ValidationMessage
   CRFElementId             OverruleReason
   DataItemId
   VisitCycleNumber
   CRFPageCycleNumber
   CRFPageTaskId
   ResponseValue
   ResponseTimestamp
   ValueCode
   UserId
   UnitOfMeasurement
   Comments
   ReviewComment
   ResponseStatus
   Changed
   SoftwareVersion
   ReasonForChange It is noted that the data segment header 1410 described in Table 10 uses the same "%%" prefix convention as the packet header to distinguish it from a data row. The first line in Table 10 names the data segment 1408. In this case, the data segment 1408 is called "DataItemResponse." The second line in Table 10 records the number of data rows to be found in the data segment body 1412 that corresponds to the data segment header 1410. The remaining lines in Table 10 names each of the fields to be found in the data segment body 1412.

(iii) Data segment body 1412. Immediately following a data segment header 1410 is a data segment body 1412. The data segment body 1412 contains the actual data that the packet encapsulates. In one embodiment, the data is stored in a series of rows that in turn hold a set of tab delimited (the delimiter is configurable) fields. The fields hold the actual data values. The number of rows in the data segment body 1412 and the individual field names are shown in the corresponding data segment header 1410. Table 11 discloses a row from the corresponding data segment for the "DataItemResponse" data segment header 1410 shown described in Table 10.

TABLE 11

An Exemplary Data Segment Body 1412

| 757 | rsl | 1 | 100050115 | | 11 | 10 | 115 | 20001 | 1 | 1 |
|---|---|---|---|---|---|---|---|---|---|---|
| 10005 | BLOOD TYPE B | | 2001-05-10 10:55:28 | | | B | rde | | | |
| 0 | 1 | 2.0.42 | 0 | | 0 | 0 | | 0 | | |

In Table 11, each data value is separated from the next by a Tab' character. Furthermore, data values are represented in simple "string" representation so that a human can read them.

(iv) Packet Definition. Packets in accordance with this embodiment of the invention are defined using an associated ASCII text file that is termed a Java properties file. An example of the definition file for the "Status Account Packet" is provided in Table 12.

TABLE 12

An exemplary packet definition file

Segments_1_0=SystemInfo,StudyInfo,StudySiteInfo,Statistics
SystemInfo_1_0=site_rota;study_rota;sites_updated;studies_
updated;patients_updated;rde_system_enabled;oc_system_enabled;
process_id;process_start_timestamp
StudyInfo_1_0=study_name;study_loading;oc_test_mode
StudySiteInfo_1_0=study_site_key;site_loading; import_
timestamp_good;import_timestamp_bad;response_timestamp_good;
response_timestamp_bad;last_load;number_of_patients;last_
process_timestamp;last_tm_packet_size;last_oc_packet_size
Statistics_1_0=process_id;studies_processed;sites_processed;
patients_processed;new_patients_processed;tm_packet_size;oc_
packet_size;timestamp Each part of the file shown in Table 12 defines a key and value pair. For example, the first line indicates that the packet will have four segments named "SystemInfo," "StudyInfo," "StudySiteInfo," and "Statistics." The remaining lines describe the layout of each of the segments. For example the "SystemInfo" segment is divided into nine different fields and they are named: "site_rota," "study rota," "sites_updated," "studies_updated," "patients_updated," "rde_system_enabled," "oc_system_enabled," "process_id," and "process_start_timestamp." Notice also that each key (the part before the '=' sign) has a suffix version code (in this case 1.0). Using this method, different versions of a packet can be defined using the same definition file. In this way, the invention supports packets that are created using earlier versions of the system.

3. Transfer of clinical definition from back-end to front-end. FIG. 15 illustrates how the packets of the present invention are used to communicate a back-end clinical definition from a back-end CDMS to a front-end RDE. The exemplary processing steps illustrated in FIG. 15 are performed using system 1300 (FIG. 1). In step 1502 O/C clinical module 12 obtains a back-end clinical definition 8 and formats the definition into an O/C Meta Packet. An O/C Meta Packet is a form of packet having the data structure illustrated in FIG. 14. In one example, the back-end clinical definition selected in processing step 1502 is "BA15428.". In this example, step 1502 produces O/C Meta Packet that has the following packet header 1402 (see also FIG. 14):

TABLE 13

Packet Header 1402 for Exemplary O/C Meta Packet

%% com.roche.rde.wip.ocmeta.OCMetaPacket:
{build.number=latest, StudyName=BA15428,
CreatedBy=sayerr, GgbVersion=1.2, OcStudyVersion=2001-06-
05, StudyVersion=1, CreatedDate=2002-05-02@16:08:42,
ModifiedBy=sayerr, ModifiedDate=2002-05-02@16:08:15,
OcSystemVersion=3.1.1}

The packet header 1400 illustrated in Table 13 identifies the packet as an O/C Meta Packet. Further, the exemplary O/C Meta Packet includes sixteen data segments 1408. Each data segment provides the details of a specific portion of the back-end clinical definition 8 selected in processing step 1502. The sixteen data segments found in the exemplary O/C Meta Packet corresponding to the back-end clinical definition 8 for the clinical trial "BA15428" are illustrated in Table 14:

TABLE 14

Data segments 1408 present in the exemplary O/C Meta Packet for "BA15428"

Clinical_planned_events
Clinical_studies
DCI_books
DCI_book_pages
DCI_modules
DCMS
DCM_layout_abs_pages
DCM_layout_graphics
DCM_layout_pages
DCM_layout_text
DCM_quest_repeat_defaults
DCM_questions
DCM_question_groups
DCM_schedules
Discrete_values
Dicrete_value_groups The name of each data segment 1408 in Table 14 corresponds to the similarly named metatable in Table 3, above. Table 3 describes the metatables that are found in a back-end clinical definition 8, in accordance with one embodiment of the present invention. To illustrate the relationship between Table 14 and Table 3, the data segment 1408 in Table 14 named "Clinical_planned_events" is used to hold the data for the metatable named "Clinical_planned_events", as described in Table 3, and so forth.

Referring to FIG. 15, in processing step 1504, the O/C Meta Packet is transferred to computer 150 (i.e, computer 150 receives the O/C Meta Packet). In step 1506, mapper server module 30 converts the O/C Meta Packet into a front-end study map that is packetized in the form of a TM Meta Packet. In addition, conversion map 32 is built so that data can be transferred to O/C database 10 from the front-end RDE in the future. The TM Meta Packet has the same data structure illustrated in FIG. 14. That is, TM Meta Packet is a packet 1400 (FIG. 14).

In the case of the exemplary clinical trial "BA15428", the TM Meta Packet created in step 1506 has the following packet header 1402:

TABLE 15

Packet Header 1400 for the Exemplary TM Meta Packet

%% com.roche.rde.wip.tmmeta.TMMetaPacket:
{StudyName=BA15428, TmSystemVersion=2.2,
build.number=latest, ModifiedDate=2002-05-02@16:27:22,
GgbVersion=1.2, CreatedDate=2002-05-02@16:27:30,
CreatedBy=sayerr, ModifiedBy=sayerr}

The packet header 1400 illustrated in Table 15 identifies the packet as a T M Meta Packet. The exemplary TM Meta Packet further includes nine data segments 1408. The nine data segments 1408 in the exemplary TM Meta Packet include the various components that are found in a front-end study definition 72, in accordance with one embodiment of the present invention. The titles of the nine data segments 1408 that are found in the exemplary TM Meta Packet for the clinical trial "BA15428" are found in Table 16:

TABLE 16

Data Segments 1408 for the Exemplary TM Meta Packet

ClinicalTrial
StudyDefinition
TrialStatusHistory
ValueData
DataItem
CaseReportFormPage
CaseReportFormElement
StudyVisit
StudyVisitCaseReportFormPage The name of each data segment 1408 in Table 16 corresponds to the similarly named metatable in Table 2, above. Table 2 describes the metatables that are found in a front-end study definition 70, in accordance with one embodiment of the present invention. The data segment 1408 in Table 14 named "Clinical_planned_events" is used to hold the data for the metatable "Clinical_planned_events" as described in Table 3, and so forth.

In processing step 1508, the TM Meta packet is delivered to RDE product 68. In processing step 1510, the RDE product is instructed to convert the TM Meta Packet into a front-end study definition. In some embodiments, processing step 1510 is facilitated using an application programming interface 193 that is provided by the RDE product 68. The use of an application programming interface ("API") 193 is advantageous because it allows for the upload of a front-end study definition 70 into an RDE product 68 without any knowledge of the specific architecture of RDE product 68. Products such as MACRO 3.0 include an API 193.

Once the TM Meta packet corresponding to the clinical trial "BA15428" is delivered to RDE product 68 at a site 104, the site 104 can commence collecting clinical data for trial "BA15428." At a later date, therefore, the clinical data collected at site 104 is collected from front-end site 104 and transferred to back-end site 140. In one embodiment of the present invention, packets 1400 are used to perform this task, using the processing steps illustrated in FIG. 16.

In step 1602, RDE product 68 is instructed to poll database 72 for new data for a given clinical trial that is managed by the front-end study definition 70 that corresponds to the clinical trial "BA15428." In some embodiments, API 193 facilitates step 1602. When data is found, process control passes to step 1604. In step 1604, RDE product 68 is instructed to format available clinical data for clinical trial "BA15428" into a "TM Data Packet." The TM Data Packet has the data structure illustrated in FIG. 14, including a packet header 1402 and data segments 1408. For example, the packet header 1402 for the clinical trial "BA15428" in one instance of processing step 1604 is disclosed in Table 17:

TABLE 17

Packet Header 1402 for Exemplary TM Data Packet

%% com.roche.rde.wip.tmdata.TMDataPacket:
{GgbVersion=1.2, CreatedBy=sayerr, ModifiedDate=2002-05-02@16:18:34, build.number=latest, TmSystemVersion=2.2,
ModifiedBy=sayerr, StudyName=BA15428, CreatedDate=2002-05-02@16:19:10}

The packet header 1400 illustrated in Table 17 identifies the packet as a TM Data Packet. In addition to the packet header, the TM Data Packet for the clinical trial "BA15428" includes five data segments 1408. They are "TrialSubject", "VisitInstance", "CaseReportFormPageInstance", "DataItemResponse", and "DataItemResponseHistory." Each of these data segments corresponds to various responses to metatables found in the front-end study definition for the clinical trial "BA15428."

In processing step 1606, the TM Data Packet is transferred to computer 150 (FIG. 1). In step 1608, mapper server module 30 reads the TM Data Packet header to determine which clinical trial the packet relates to and the site 104 from which the packet originated. In step 1610, data exchange module 42, in conjunction with mapper server module 30 and the appropriate conversion map 32, converts the TM Data Packet into an "O/C Data Packet." The O/C Data Packet created in step 1610 has the data structure disclosed in FIG. 14. In particular, the O/C Data Packet created in step 1610 includes a packet header 1402 and a single data segment 1408 entitled "BatchLoad." In the case of the BA15428 clinical trail, the O/C Data Packet has the following packet header 1402:

TABLE 18

Packet Header 1402 for Exemplary O/C Data Packet

%% com.roche.rde.wip.ocdata.OCDataPacket:
{ModifiedDate=2002-05-02@16:27:55, CreatedBy=sayerr,
OcSystemVersion=3.1.1, StudyName=BA15428, GgbVersion=1.2,
CreatedDate=2002-05-02@16:27:55, build.number=latest,
StudyVersion=1, ModifiedBy=sayerr}

The packet header 1402 of Table 18 identifies the packet as an O/C Data Packet. In step 1612, the O/C Data Packet is delivered to CDMS 140 and read into O/C database 10. In some embodiments, O/C data capture API 14 is used to load the data in the O/C Data Packet.

Taken together, FIGS. 15 and 16 describe how packets having the novel data structure disclosed in FIG. 14 can be used to export back-end clinical definitions from a CDMS to a front-end RDE as well as to send data from the RDE to a back-end CDMS in accordance with "Use Case 1" and "Use Case 2."

7.3.4 USE CASE 3: AUTOMATED PAPERLESS DISCREPANCY MANAGEMENT

One advantage of the present invention is the manner in which discrepancies are resolved. Discrepancies arise in a number of different situations. For example, a discrepancy arises when clinical data has been entered that is not consistent with allowed data types and/or data ranges. In some embodiments of the present invention, a discrepancy is identified by data validation module 1208 (FIG. 12). The steps in which a discrepancy is discovered and resolved in accordance with one embodiment are illustrated in FIG. 13 in conjunction with system 1300 (FIG. 1).

In step 1302 (FIG. 13), data validation module 1208 detects a discrepancy in O/C database 10. Data validation module 1208 (FIG. 12) is a component of O/C clinical module 12 in accordance with some embodiments of the present invention. It will be appreciated that a discrepancy may be discovered in O/C database 10 using other modules, such as modules that are not shown in FIG. 1 or FIG. 12. A discrepancy is any form of data entry that is inconsistent with the clinical design. For example, a discrepancy is a data value that exceeds an allowed data range. In the case of a blood pressure measurement, a discrepancy is a nonsensical measurement, such as "10" over "20." Because data validation module 1208 has access to the data collected for every subject in a clinical trial, discovery of more complex discrepancies is possible. For example, data validation module 1208 may determine that the estrogen levels in a particular male subject, or group of male subjects, is higher than any other male subjects surveyed. Therefore, although the measured estrogen levels are within allowed ranges, data validation module 1208 may flag the systematic high estrogen level as a discrepancy.

Referring to step 1304, server process module 38 is notified of the discrepancy. In response, server process module 38 retrieves the clinical trial X in which the discrepancy arose from configuration file 40 (FIG. 1). One of skill in the art will appreciate that there is a substantial number of different ways in which step 1304 may be performed. For example, in some embodiments, server process module 38 is always running and the data for clinical trial X is already loaded. In step 1306, the front-end site 104 where the discrepancy arose is identified using configuration file 40 (FIG. 1). An important aspect of "Use Case 3" is that the discrepancy resolution is performed in a manner that is fully audited in accordance with regulatory agency guidelines. Accordingly, in step 1308, audit trail 12 (FIG. 1) is updated to note the discrepancy that was discovered by data validation module 1208 in O/C database 10. In some embodiments, step 1308 comprises updating an audit trail (not shown) for the back-end CDMS 140 (FIG. 1) and an audit trail (not shown) for the front-end RDE system 104 (FIG. 1). In some embodiments of the present invention, step 1308 is performed in conjunction with audit trail module 1210 (FIG. 12) and/or database module 48.

An advantage of the present invention is that data that is stored in accordance with a back-end clinical definition may be communicated to a front-end site 104 Furthermore, data collected at a front-end site 104 may be communicated to a back-end CDMS, such as computer 140. Because the back-end and front-end sites use very different data formats, a conversion step is used. Accordingly, in process step 1310, the discrepancy is converted from the back-end format used to store the clinical value or values associated with the discrepancy into a form that is compatible with the appropriate front-end study definition 70. Conversion step 1310 takes advantage of the novel conversion map 32 described above. Conversion map 32 includes a record of matching first and second components in the back-end clinical definition 8 and the corresponding front-end study definition 70 (FIG. 1).

In processing step 1312, the discrepancy is sent to the front-end site 104 where the discrepancy was entered. Typically, step 1312 involves sending the discrepancy to RDE product 68 where it is interpreted in conjunction with the front-end study definition 70 that corresponds to the clinical study in which the discrepancy arose. In one embodiment of the present invention, the discrepancy is sent to RDE product 68 with a message generated by data validation module 1208. For example, the data validation module 1208 may state the nature of the discrepancy and any appropriate responses. In one instance, the observed clinical event in which a discrepancy arose may be a query that asks whether the subject has a cough. In response, the clinician responded "not determined." Data validation module 1208 notes a discrepancy and sends, along with the discrepancy (e.g., the data value that must be reentered correctly) a message stating "Yes/No answer required."

In processing step 1314, server process module 38 and/or data exchange module 42 receives the discrepancy response from RDE product 68. In step 1316, the discrepancy response is then stored in audit trail 112 and in step 1318 the discrepancy response is converted into the appropriate back-end clinical definition format 8 using the appropriate conversion map 32. Then, the discrepancy response is transferred to back-end computer 140 (FIG. 1). It will be appreciated that the temporal sequence of many of the steps disclosed above, including steps 1314 and 1316 is not important. In step 1320, data validation module 1208 determines whether the response received from RDE 68 resolves the discrepancy. If so (FIG. 13; 1320-Yes), then the discrepancy response is stored as a discrepancy resolution in O/C database 10. Further, the back-end discrepancy is closed. In the example where a "Yes" or "No" answer was required, the discrepancy response may be the answer "Yes." Because the answer "Yes" is an allowed answer to the query, data validation module 1208 accepts the answer and replaces the previous value (e.g., "not determined") with the value "Yes" in step 1324. In instances where the response does not resolve the discrepancy (FIG. 13; 1320-No), this failure is noted in audit trail 112 in step 1322. Then, process control returns to step 1312, in which the discrepancy is sent to the front-end site 104 where the discrepancy was entered for further resolution.

The process disclosed in FIG. 13 is advantageous for a number of reasons. Rather than sending a FAX, letter or report when a data validation module 1208 discovers a discrepancy, the present invention makes use of the novel conversion map 32 to query a front-end site directly about the discrepancy. Then, the conversion map 32 is again utilized to convert the discrepancy response and, if acceptable, store the response in the CDMS (e.g., back-end site 140). Furthermore, the process disclosed in FIG. 13 is advantageous because the electronic audit measures found in system 1300 (FIG. 1) may automatically be used without manual input. Yet another advantage of the process disclosed in FIG. 13 is that it is performed in a paperless fashion. Thus, the process disclosed in FIG. 13 resolves discrepancies in a fully automated, audited fashion, with minimal reliance on manual input.

Using Packets to resolve discrepancies. In one embodiment of the present invention, "Use Case 3" is facilitated by the use of packets having the data structure disclosed in FIG. 14. This embodiment is illustrated in FIG. 17. The steps illustrated in FIG. 17 may be used to execute the embodiment shown in FIG. 13. In step 1702, O/C clinical module 12 discovers a discrepancy in O/C database 10 and packetizes (formats) the discrepancy into an O/C Discrepancy Packet that has the data structure disclosed in FIG. 14. In processing step 1704, the O/C Discrepancy Packet is transferred to computer 150. In processing step 1706, mapper server module 30 (FIG. 1), working in conjunction with data exchange module 42 and mapper server module 30, converts the O/C Discrepancy Packet into a front-end TM Discrepancy Packet. The front-end TM Discrepancy Packet has the data structure disclosed in FIG. 14. In step 1608, the TM Discrepancy Packet is transferred to RDE product 68 on site 104. In step 1610, an investigator corrects the discrepancy. Subsequently, the resolved discrepancy may be transferred back to O/C database in a manner that reverses the steps illustrated in FIG. 16. Alteratively, the resolved discrepancy can be transferred to O/C database 10 using the processing steps illustrated in FIG. 16.

8. ADDITIONAL EMBODIMENTS

Patient Registration. When allowed by RDE product 68, and for those studies that allow site-initiated patient enrollment, one embodiment of the present invention will allow a front-end study definition 70 to be configured to avoid reliance on manually-entered patient, investigator, and site codes. In studies where automatic assignment of patient codes is not feasible, one embodiment of the present invention will require identifier-code responses (derived or manually entered) prior to loading data for that subject using O/C clinical module 12. Where the identifier-code response is missing or inappropriate (e.g., wrong patient code for the designated site and investigator), one embodiment of the present invention will not load that patient's data until the code is corrected. However, other patient data from that site will continue loading. If an OC database 10 patient code is already associated with a subject of front-end study definition 70, one embodiment of the present invention will reject that patient code as an assignment for a different patient at the same site 104.

Compatibility. Some embodiments of the present invention operate with Oracle Clinical version 4.0 and MACRO version 3. Some embodiments of the present invention operate with Oracle Clinical version 4.0 and MACRO version 2 installations. Some embodiments of the present invention operate with Oracle Clinical version 3.1.1.1 and MACRO version 3. Some embodiments of the present invention operate with Oracle Clinical version 3.1.1.1 and MACRO version 2 installations. Some embodiments of the present invention work with MACRO v2.2.

Activity and Error Logs. Some embodiments of the present invention include activity and error logs at different levels of granularity. The events that are recorded by such error logs include, for example, user actions, such as metadata mapping, re-configuration, study audits, and administrative pausing and restarting of activity for individual sites or studies. In some embodiments, such logs will record successful and unsuccessful executions of data-translation and data-loading steps.

Security. In some embodiments of the present invention, all remote users (e.g., user of console module 44, users of mapper server module 30, and users of server process module 38) have access to an external, corporate user directory (e.g., via lightweight directory access protocol). Furthermore, in some embodiments of the present invention, the system administrator is permitted to either store database-account passwords or to require that users enter them manually whenever system 1300 is initiated.

HadValue. Some embodiments of the present invention work with MACRO version 2.2. In particular, some embodiments use the MACRO 2.2 HadValue field to detect that deletion of a value with a skip-condition has occurred. In such instances, such deletions (e.g., the start and end dates of a deleted medication) will be transferred to O/C database 10 from RDE 68.

Repeating groups. Some embodiments of the present invention allow back-end clinical definition 8 designers to update a repeating group to have a new, higher maximum number of repeats.

Study audits. In some embodiments, mandatory questions that are not in any data collection instrument book page (Table 3) in a back-end clinical definition 8 are ignored. That is, such question are not placed in the corresponding front-end study definition 72 that is created using the conversion algorithms of the present invention.

9. REFERENCES CITED

All references cited herein are incorporated by reference in their entirety and for all purposes to the same extent as if each individual publication or patent or patent application was specifically and individually indicated to be incorporated by reference in its entirety for all purposes.

10. ALTERNATE EMBODIMENTS

The present invention can be implemented as a computer program product that comprises a computer program mechanism embedded in a computer readable storage medium. For instance, the computer program product could contain the program modules illustrated in FIGS. 1 and 2 and related figures. These program modules may be stored on a CD-ROM, magnetic storage product, or any other computer readable data or program storage product. The software modules in the computer program product may also be distributed electronically, via the Internet or otherwise, by transmission of a computer data signal (in which the software modules are embedded) on a carrier wave.

While certain exemplary embodiments have been described in detail and shown in the accompanying drawings, it will be appreciated that such embodiments merely illustrate, rather than restrict, the broad invention. It will further be appreciated that this invention is not to be limited to the specific arrangements and constructions shown and described, since various other modifications may occur to those with ordinary skill in the art.

We claim:

1. A method for resolving a discrepancy arising in a clinical data management system (CDMS), the method comprising:

converting the discrepancy from a back-end format, used to store a clinical value corresponding to said discrepancy, into a front-end format that is compatible with a front-end study definition;

transferring said discrepancy, in said front-end format, to a front-end site where the clinical value associated with said discrepancy was entered;

receiving a discrepancy response from said front-end site; and when said discrepancy response resolves said discrepancy, storing said discrepancy response.

2. The method of claim 1, the method further comprising determining whether said discrepancy response resolves said discrepancy by:

(i) converting the discrepancy response from said front-end format to said back-end format; and (ii) verifying that said discrepancy response satisfies a data entry criterion associated with said clinical value.

3. The method of claim 2, wherein said data entry criterion is a data type or a data range.

4. The method of claim 1 wherein, when said discrepancy response does not resolve said discrepancy, the method further comprises repeating said transferring, receiving, and storing.

5. The method of claim 1, the method further comprising updating an audit trail for the CDMS and an audit trail for the front-end site with an account of said discrepancy.

6. The method of claim 1, the method further comprising storing said discrepancy response in an audit trail.

7. The method of claim 1, wherein said CDMS includes: (1) a database to store said clinical value, (2) a SAS module to analyze said clinical value using statistics, (3) a generic loader to load data not found in a case report form, (4) a thesaurus module to access a thesaurus that harmonizes adverse reaction terminology, and (5) an audit trail module to access an audit trail.

8. The method of claim 1, wherein a conversion map is used in said converting step, said conversion map storing a one-to-one correspondence between respective questions and events in said back-end format and respective questions and events in said front-end study definition.

9. A computer readable memory used to direct a client/server system to function in a specified manner, comprising:
   a back-end CDMS, said back-end CDMS capable of saving data in accordance with a back-end clinical definition;
   a remote data entry module for collecting clinical data in accordance with a front-end study definition; and
   a mapper server module for resolving a discrepancy arising in said back-end CDMS, said mapper server module including executable instructions stored in said computer readable memory, said executable instructions including:
   instructions for converting the discrepancy from said back-end clinical definition format used to store a clinical value corresponding to said discrepancy into said front-end study definition format;
   instructions for transferring said discrepancy, in said front-end study definition format, to a front-end site where the clinical value associated with said discrepancy was entered;
   instructions for receiving a discrepancy response from said front-end site; and
   instructions for storing said discrepancy response in said back-end CDMS when said discrepancy response resolves said discrepancy.

10. The computer readable memory of claim 9, the mapper server module further comprising instructions for determining whether said discrepancy response resolves said discrepancy by:
   (i) converting the discrepancy response from said front-end study definition format to said back-end clinical definition format; and
   (ii) verifying that said discrepancy response satisfies a data entry criterion associated with said clinical value.

11. The computer readable memory of claim 10, wherein said data entry criterion is a data type or a data range.

12. The computer readable memory of claim 9, wherein the mapper server module further includes instructions for repeating said instructions for transferring, receiving, and storing when said discrepancy response does not resolve said discrepancy.

13. The computer readable memory of claim 9, wherein said mapper server module further includes instructions for updating an audit trail for the CDMS and an audit trail for the front-end site with an account of said discrepancy.

14. The computer readable memory of claim 13, wherein said memory further includes a database module that includes instructions for updating an audit trail in response to the execution of said instructions for updating said audit trail with an account of said discrepancy.

15. The computer readable memory of claim 9, wherein said mapper server module further includes instructions for updating an audit trail with said discrepancy response.

16. The computer readable memory of claim 15, wherein said memory further includes a database module that includes instructions for updating said audit trail in response to the execution of said instructions for updating said audit trail with said discrepancy response.

17. The computer readable memory of claim 9, wherein said back-end CDMS includes: (1) a database to store said clinical value, (2) a SAS module to analyze said clinical value using statistics, (3) a generic loader to load data not found in a case report form, (4) a thesaurus module to access a thesaurus that harmonizes adverse reaction terminology, and (5) an audit trail module to access an audit trail.

18. The computer readable memory of claim 9, wherein a conversion map is used by said instructions for converting, said conversion map storing a one-to-one correspondence between respective questions and events in said back-end clinical definition and respective questions and events in said front-end study definition.

19. A computer program product for use in conjunction with a computer having a processor,
   said computer program product comprising a computer readable storage medium and a computer program mechanism embedded therein, the computer program mechanism for resolving a discrepancy arising in a CDMS, the computer program mechanism causing the processor to execute the steps of:
   converting the discrepancy from a back-end format used to store a clinical value corresponding to said discrepancy into a front-end format, wherein the front-end format is compatible with a front-end study definition;
   transferring said discrepancy, in said front-end format, to a front-end site where the clinical value associated with said discrepancy was entered;
   receiving a discrepancy response from said front-end site; and
   when said discrepancy response resolves said discrepancy, storing said discrepancy response.

20. The computer program product of claim 19, wherein the computer program mechanism determines whether said discrepancy response resolves said discrepancy by:
   (i) converting the discrepancy response from said front-end format to said back-end format; and
   (ii) verifying that said discrepancy response satisfies a data entry criterion associated with said clinical value.

21. The computer program product of claim 19, wherein said data entry criterion is a data type or a data range.

22. The computer program product of claim 19 wherein, when said discrepancy response does not resolve the discrepancy, the transferring, receiving, and storing are repeated.

23. The computer program product of claim 19, the computer program mechanism further causing the processor to execute the step of updating an audit trail with an account of the discrepancy.

24. The computer program product of claim 19, the computer program mechanism further causing the processor to execute the step of storing said discrepancy response in an audit trail.

25. The computer program product of claim 19, wherein said CDMS includes (1) a database to store said clinical value, (2) a SAS module to analyze said clinical value using statistics, (3) a generic loader to load data not found in a case report form, (4) a thesaurus module to access a thesaurus that harmonizes adverse reaction terminology, and (5) an audit trail module to access an audit trail.

26. The computer program product of claim 19, wherein said converting uses a conversion map, the conversion map storing a one-to-one correspondence between respective questions and events in said back-end format and respective questions and events in said front-end study definition.

27. A method for converting a back-end clinical definition into a front-end study definition, the method comprising:

formatting said back-end clinical definition into a back-end data packet, wherein said back-end data packet includes a first packet header and a first plurality of data segments;

receiving said first data packet;

converting said first data packet into a front-end data packet, wherein said front-end data packet includes a second packet header and a second plurality of data segments; and delivering said front-end data packet, thereby converting said back-end clinical definition into said front-end study definition.

28. The method of claim 27 wherein said converting further comprises building a conversion map that allows for conversion of clinical data formatted in accordance with said front-end study definition into clinical data formatted in accordance with said back-end clinical definition.

29. A method for storing clinical data, comprising:

formatting said clinical data into a front-end data packet, wherein said front-end data packet includes a first packet header and a first plurality of data segments;

receiving said first data packet;

converting said first data packet into a back-end data packet, wherein said back-end data packet includes a second packet header and a second plurality of data segments; and delivering said back-end data packet, thereby storing said clinical data.

30. A conversion map comprising a key that matches respective components in a back-end clinical definition with corresponding components in a corresponding front-end study definition.

31. The method of claim 30, wherein a respective component includes a listing of visits, a form, or a question.

\* \* \* \* \*